US009185913B2

(12) United States Patent
Maisch et al.

(10) Patent No.: US 9,185,913 B2
(45) Date of Patent: *Nov. 17, 2015

(54) 10H-BENZO[G]PTERIDINE-2,4-DIONE DERIVATIVES, METHOD FOR THE PRODUCTION THEREOF, AND USE THEREOF

(75) Inventors: Tim Maisch, Nürnberg (DE); Andreas Späth, Regensburg (DE)

(73) Assignee: TRIOPTOTEC GMBH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/127,472

(22) PCT Filed: Jun. 22, 2012

(86) PCT No.: PCT/EP2012/062173
§ 371 (c)(1),
(2), (4) Date: Feb. 21, 2014

(87) PCT Pub. No.: WO2012/175730
PCT Pub. Date: Dec. 27, 2012

(65) Prior Publication Data
US 2014/0200220 A1 Jul. 17, 2014

(30) Foreign Application Priority Data

Jun. 22, 2011 (DE) .......................... 10 2011 105 653

(51) Int. Cl.
*A61K 41/00* (2006.01)
*C07D 475/14* (2006.01)
*A01N 43/90* (2006.01)

(52) U.S. Cl.
CPC ............ *A01N 43/90* (2013.01); *A61K 41/0057* (2013.01); *C07D 475/14* (2013.01)

(58) Field of Classification Search
CPC .......................... A61K 41/0057; C07D 475/14
See application file for complete search history.

(56) References Cited

U.S. PATENT DOCUMENTS

| 3,822,133 A | 7/1974 | Short et al. | |
|---|---|---|---|
| 2014/0212459 A1* | 7/2014 | Maisch et al. ................. | 424/400 |

FOREIGN PATENT DOCUMENTS

| DE | 22 24 371 A1 | 1/1973 | |
|---|---|---|---|
| WO | WO 00/04930 A2 | 2/2000 | |
| WO | WO 2010/019208 A1 | 2/2010 | |
| WO | WO 2010/119208 * | 2/2010 | ............ A01N 43/60 |
| WO | WO 2011/008247 A1 | 1/2011 | |

OTHER PUBLICATIONS

International Search Report and Written Opinion in German dated Aug. 13, 2012 issued in corresponding International patent application No. PCT/EP2012/062173.

DIN EN 14885:2007-01 "Chemische Desinfektionsmittel und Antiseptika—Anwendung Europäischer Normen für chemische Desinfektionsmittel and Antiseptika;" Deutsche Fassung EN 14885:2006—"Chemical disinfectants and antiseptics—Application of European Standards for chemical disinfectants and antiseptics" (an index in German and English is attached).
Seiji Shinkai, et al. "Coenzyme Models. Part 23. Formation and Reactivity of the Stable 'Quinone Form' of Flavin in Cationic Polymer Matrices," Journal of the Chemical Society, Perkin Transactions 1, Jan. 1, 1980, pp. 1622-1625, XP55034011.
Ron Blonder, et al., "Application of a Nitrospiropyran-FAD-Reconstituted Glucose Oxidase and Charged Electron Mediators as Optobioelectronic Assemblies for the Amperometric Transduction of Recorded Optical Signals: Control of the "On"—"Off" Direction of the Photoswitch," Journal of the American Chemical Society, Dec. 1, 1997, vol. 119, No. 49, pp. 11747-11757, XP55034326.
R.B. Barlow, et al., "144. A Series of 9-Dialkylaminoalkylisoalloxazines," Journal of the Chemical Society (Resumed), Jan. 1, 1950, pp. 713-717, XP55034329.
Donald B. McCormick, et al., "Syntheses of 8-Bromo-5'-adenylate-Containing Nucleotides," Journal of Medicinal Chemistry, vol. 12, No. 2, Mar. 1, 1969, pp. 333-334, XP55034331.
Suk-Wah Tam-Chang, et al., "Synthesis of Symmetrical and Unsymmetrical Alkyl Disulfides with Attached Flavin Analog for Formation of Self-Assembled Monolayers of Gold," Tetrahedron, Elsevier Science Publishers, Amsterdam, NL, vol. 55, No. 47, Nov. 19, 1999, pp. 13333-13344, XP004188297.
Takashi Harayama, et al., "Reaction of 6-Ethylamino-3-methyluracil with Nitrobenzenes," Journal of Heterocyclic Chemistry, vol. 23, No. 5, Sep. 1, 1986, pp. 1507-1509, XP55034208.
Christina K. Remucal, et al., "Photosensitized Amino Acid Degradation in the Presence of Riboflavin and Its Derivatives," Environmental Science & Technology, vol. 45, No. 12, Jun. 15, 2011, pp. 5230-5237, XP55034035.
Christopher Cox, "Strong Hydrogen Bonding to the Amide Nitrogen Atom in an "Amide Proton Sponge": Consequences for Structure and Reactivity," Angewandte Chemie. International Edition, Wiley VCH Verlag, Weinheim, vol. 38, No. 6, Jan. 1, 1999, pp. 798-800, XP008154136.
Alexander Barthel, et al., "Synthesis of Dimeric Quinazolin-2-one, 1,4-Benzodiazepin-2-one, and Isoalloxazine Compounds as Inhibitors of Amyloid Peptides Association," Arch. Pharm. Chem. Life Sci., vol. 342, 2009, pp. 445-452.
Michael C. Falk, et al., "Synthetic Flavinyl Peptides Related to the Active Site of Mitochondrial Monoamine Oxidase. I. Chemical and Spectral Properties," Biochemistry, vol. 15, No. 3, 1976, pp. 639-645.
Jens Butenandt, et al., "A Comparative Repair Study of Thymine- and Uracil-Photodimers With Model Compounds and a Photolyase Repair Enzyme," Chem. Eur. J., vol. 6, No. 1, 2000, pp. 62-72.
Carolina Moura, et al., "Rhenium(v) Oxocomplexes With Novel Pyrazolyl-Based $N_4$- and $N_3S$-Donor Chelators," Dalton Transactions, 2006, pp. 5630-5640.
Marcin Jasiński, "Synthesis of New Bis-imidazole Derivatives," Helvetica Chimica Acta, vol. 90, 2007, pp. 1765-1780.
A. A. Miles, et al., "The Estimation of the Bactericidal Power of the Blood," The Journal of Hygiene, vol. 38, No. 6, Nov. 1938, pp. 732-749.

(Continued)

*Primary Examiner* — Erich A Leeser
(74) *Attorney, Agent, or Firm* — Ostrolenk Faber LLP

(57) ABSTRACT

The present disclosure relates to 10H-benzo[g]pteridine-2,4-dione derivatives, to the production thereof, and to the use thereof.

23 Claims, 16 Drawing Sheets

(56) References Cited

OTHER PUBLICATIONS

Richard R. Holmes, et al., "A Simple Method for the Direct Oxidation of Aromatic Amines to Nitroso Compounds," vol. 82, 1960, pp. 3454-3456.

Robert Epple, et al., "Investigation of Flavin-Containing DNA-Repair Model Compounds," J. Am. Chem. Soc., vol. 119, 1997, pp. 7440-7451.

Naomi Sakai, et al., "Electrostatics of Cell Membrane Recognition: Structure and Activity of Neutral and Cationic Rigid Push-Pull Rods in Isoelectric, Anionic, and Polarized Lipid Bilayer Membranes," J. Am. Chem. Soc., vol. 123, 2001, pp. 2517-2524.

Sathya Srinivasachari, et al., "Polycationic β-Cyclodextrin 'Click Clusters': Monodisperse and Versatile Scaffolds for Nucleic Acid Delivery," J. Am. Chem. Soc., vol. 130, pp. 4618-4627.

Youli Xiao, et al., "Revisiting the IspH Catalytic System in the Deoxyxylulose Phosphate Pathway: Achieving High Activity," J. Am. Chem. Soc., vol. 131, 2009, pp. 9931-9933.

Antonio Monge, et al., "Hypoxia-Selective Agents Derived From Quinoxaline 1,4-Di-N-Oxides," J. Med. Chem., vol. 38, 1995, pp. 1786-1792.

Olaf Wiest, et al., "Design, Synthesis, and Evaluation of a Biomimetic Artificial Photolyase Model," J. Org. Chem., vol. 69, 2004, pp. 8183-8185.

Toru Sugaya, et al., "Improved Synthesis of Thromboxane $A_2$ Receptor Antagonists With a Dibenzoxepin Ring System," Synthesis, Oct. 1995, pp. 1257-1262.

Donald B. McCormick, "Flavin Derivatives via Bromination of the 8-Methyl Substituent (1)," Apr. 1970, pp. 447-450.

John M. Boyce, et al. "Guideline for Hand Hygiene in Health-Care Settings. Recommendations of the Healthcare Infection Control Practices Advisory Committee and the HICPAC/SHEA/APIC/IDSA Hand Hygiene Task Force", Am. J. Infect. Control, vol. 30, No. 8, 2002, pp. S1-S46.

John M. Boyce, et al. "Guideline for Hand Hygiene in Health-Care Settings: Recommendations of Healthcare Infection Control Practices Advisory Committee and the HICPAC/SHEA/APIC/IDSA Hand Hygiene Task Force," Infection Control and Hospital. Epidemiology, vol. 23, No. S12, Dec. 2002, pp. S3-S40.

Didier Pittet, MD, et al., "The World Health Organization Guidelines on Hand Hygiene in Health Care and Their Consensus Recommendations," Infection Control and Hospital Epidemiology, vol. 30, No. 7, update from Jul. 2009.

Dr. H. F. Rabenau, et al., ("Leitlinie der Deutschen Vereinigung zur Bekämpfung der Viruskrankheiten (DVV) e.V. und des Robert Koch-Instituts (RKI) zur Prüfung von chemischen Desinfektionsmitteln auf Wirksamkeit gegen Viren in der Humanmedizin" Bundesgesundheitsblatt, Gesundheitsforschung, Gesundheitschutz 51(8), (2008), pp. 937-945) (with English translation)—Guideline of "Deutsche Vereinigung zur Bekämpfung der Viruskrankheiten (DVV; German Association for the Control of Virus Diseases) and Robert Koch Institute (RKI; German Federal Health Authority) for Testing the Virucidal Efficacy of Chemical Disinfectants in the Human Medical Area."

\* cited by examiner

Flavin FI-09:

Flavin Fl-11:

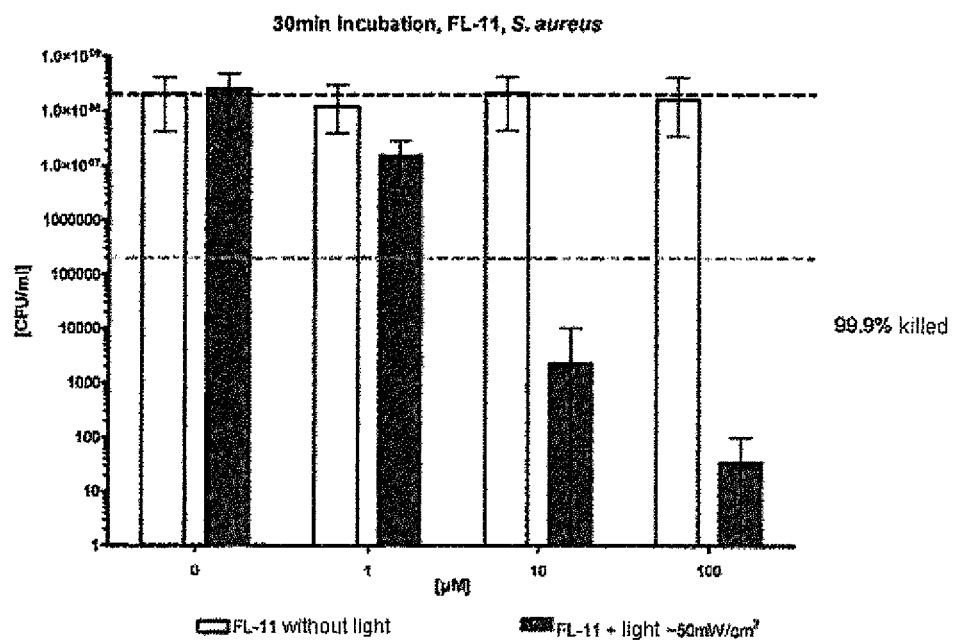

Flavin Fl-12

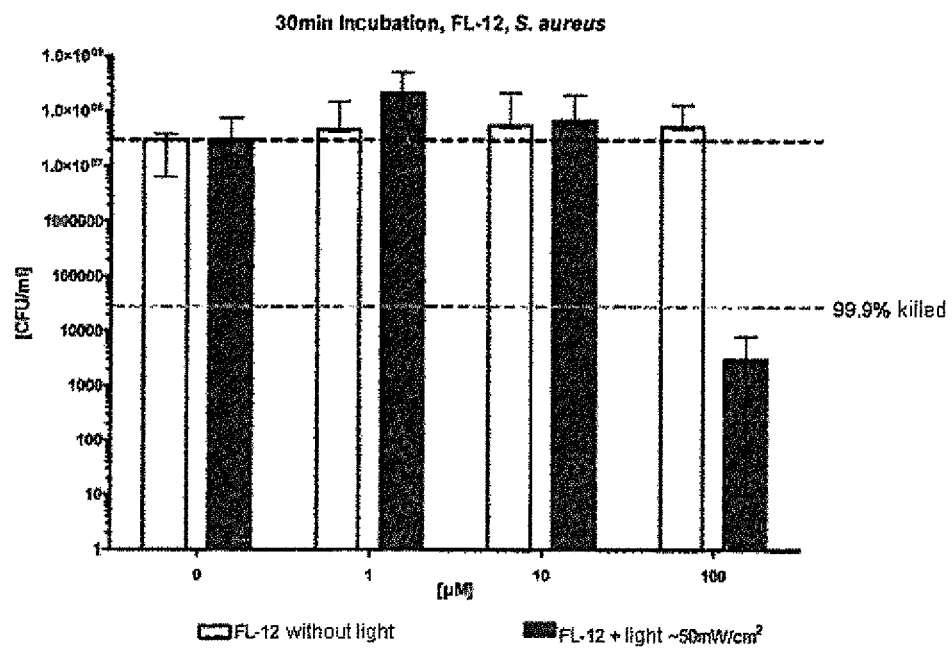

Flavin FL-14

Flavin FL-16

Flavin Fl-18

Flavin Fl-25

Flavin FL-09b

10H-BENZO[G]PTERIDINE-2,4-DIONE DERIVATIVES, METHOD FOR THE PRODUCTION THEREOF, AND USE THEREOF

CROSS REFERENCE TO RELATED APPLICATIONS

The present application is a 35 U.S.C. §371 National Phase conversion of PCT/EP2012/062173, filed Jun. 22, 2012, which claims benefit of German Application No. 10 2011 105 653.3, filed Jun. 22, 2011, the disclosure of which is incorporated herein by reference. The PCT International Application was published in the German language.

TECHNICAL FIELD OF THE INVENTION

The present invention relates to 10H-benzo[g]pteridine-2,4-dione derivatives, and to the preparation and use thereof.

BACKGROUND OF THE INVENTION

The active or passive penetration of pathogens into a host, the inherent presence of these therein and the propagation thereof is referred to as infection. Sources of infectious particles occur everywhere. For example, the human body is colonized by a large number of microorganisms which are generally kept under control by the normal metabolism and an intact immune system. However, a weakened immune system, for example, may result in significant propagation of the pathogens and, according to the type of pathogen, in different disease symptoms. For many pathogen-induced diseases, medicine has specific antidotes at its disposal, for example antibiotics against bacteria or antimycotics against fungi or virustatics against viruses. However, increasing occurrence of resistant pathogens is observed when these antidotes are used, and some of these pathogens have resistances against several antidotes at the same time. The occurrence of these resistant or multiresistant pathogens has made the treatment of infection disorders increasingly difficult. The clinical consequence of resistance is manifested by a failure of the treatment, particularly in the case of immunosuppressed patients.

New starting points for control of resistant or multiresistant disease pathogens are therefore firstly the search for new antidotes, for example antibiotics or antimycotics, and secondly the search for alternative means of inactivation.

An alternative method which has been found to be useful is the photodynamic inactivation of microorganisms. Two different photooxidative processes play a crucial role in the photodynamic inactivation of microorganisms. Prerequisites for the running of a photooxidative inactivation are firstly the presence of a sufficient amount of oxygen and secondly the localization of a so-called photosensitizer, which is excited by light of an appropriate wavelength. The excited photosensitizer can bring about the formation of reactive oxygen species (ROS), which can form firstly free radicals, for example superoxide anions, hydrogen peroxide or hydroxyl radicals, and/or secondly excited molecular oxygen, for example singlet oxygen.

For both reactions, the photooxidation of specific biomolecules directly adjacent to the reactive oxygen species (ROS) is of primary importance. This involves particularly oxidation of lipids and proteins which occur, for example, as constituents of the cell membrane of microorganisms. The destruction of the cell membrane in turn results in inactivation of the microorganisms in question. For viruses and fungi, a similar elimination process is assumed.

For example, singlet oxygen attacks all molecules. However, unsaturated fatty acids in the membranes of bacteria are particularly prone to damage. Healthy endogenous cells have a cellular defense against attacks by free radicals, called catalases or superoxide dismutases. Therefore, healthy endogenous cells can counteract damage by reactive oxygen species (ROS), for example free radicals or singlet oxygen.

The prior art discloses numerous photosensitizers which come, for example, from the group of the porphyrins and derivatives thereof or phthalocyanines and derivatives thereof or fullerenes and derivatives thereof or derivatives of the phenothiazinium structure, for example methylene blue or toluidine blue, or representatives of the phenoxazinium series, for example Nile blue. The photodynamics of methylene blue or toluidine blue with respect to bacteria have already been used, for example, in dentistry.

The photosensitizers known from the prior art are usually substances having a relatively complex molecular structure and therefore complex preparation processes.

It is known that 10-methyl-10H-benzo[g]pteridine-2,4-dione derivatives riboflavin and tetraacetylriboflavin have high yields of singlet oxygen, although their affinity for microorganisms is low. It is additionally known that singlet oxygen can diffuse only over a short distance before it reacts or is degraded. Therefore, the inactivation of microorganisms by 10-methyl-10H-benzo[g]pteridine-2,4-dione derivatives riboflavin and tetraacetylriboflavin is inadequate.

Moreover, WO 2010/019208 A1 and WO 2011/008247 A1 disclose numerous flavin, roseoflavin and riboflavin derivatives which can bind to flavin mononucleotide (FMN) riboswitches. Riboswitches are RNA elements in untranslated regions of the mRNA of prokaryotes, fungi and plants, which bind low molecular weight metabolites, for example FMN, and then regulate gene expression. For example, after binding of FMN to FMN riboswitches of prokaryotes, the expression of enzymes responsible for riboflavin and FMN biosynthesis is repressed, as a result of which riboflavin and FMN biosynthesis stops. Riboflavin assumes a central role in the metabolism, since it serves as a precursor for flavin coenzymes. Therefore, suppressed riboflavin and FMN biosynthesis leads to reduced viability.

However, this form of control of pathogenic microorganisms can likewise result in occurrence of resistances, which can arise, for example, as a result of mutations in the RNA elements in question.

It is therefore an object of the present invention to provide novel photosensitizers which more efficiently inactivate microorganisms.

SUMMARY OF THE INVENTION

The object of the present invention is achieved by the provision of a compound having the formula (1):

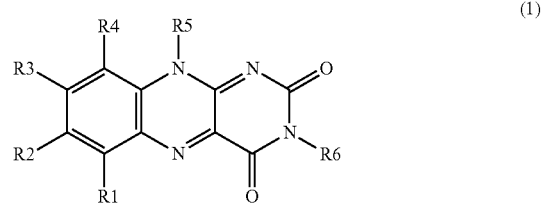

where A) only 1 R1, R2, R3 or R4 radical is an organic radical of the general formula -(C(D)(E))$_n$-X or -(C(D)

(E))$_k$-aryl-(C(D)(E))$_l$-X, where h is an integer from 1 to 20 and k, l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having only one quaternary nitrogen atom and aryl is a substituted or unsubstituted aromatic system or a substituted or unsubstituted heteroaromatic system which does not contain any nitrogen atom, and where the R1, R2, R3 or R4 radicals which are not -(C(D)(E))$_h$-X or -(C(D)(E))$_k$-aryl-(C(D)(E))$_l$-X may be the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals is the same or different and is independently hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or where B) only 1 R5 or R6 radical is an organic radical of the general formula -(C(D)(E))$_h$-X or -(C(D)(E))$_k$-aryl-(C(D)(E))$_l$-X, where h is an integer from 1 to 20 and k, l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having only one quaternary nitrogen atom and aryl is a substituted or unsubstituted aromatic system or a substituted or unsubstituted heteroaromatic system which does not contain any nitrogen atom, and where the R5 or R6 radical which is not -(C(D)(E))$_h$-X or -(C(D)(E))$_k$-aryl-(C(D)(E))$_l$-X is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where the R1 to R4 radicals may each independently be the same or different and are hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms.

The inventive compound having the formula (1) is a 10H-benzo[g]pteridine-2,4-dione or flavin derivative, which is also referred to as such hereinafter.

The counterion used for the positively charged, quaternary nitrogen atom may be any suitable anion. Preferably, the counterions used for the positively charged, quaternary nitrogen atom are anions which enable the provision of a pharmacologically acceptable salt.

BRIEF DESCRIPTION OF THE DRAWINGS

FIG. 2b) shows the results of incubation of *Staphylococcus aureus* samples with FL-11 for 30 minutes;
FIG. 3b) shows the results of incubation of *Staphylococcus aureus* samples with FL-12 for 30 minutes.

DESCRIPTION OF PREFERRED EMBODIMENTS

Figure 1:
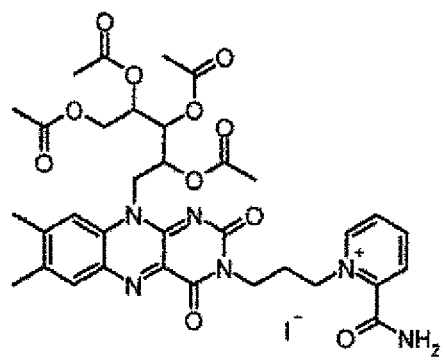
FIG. 1 shows the structural formula of Flavin FL-09.

In a preferred embodiment of the present invention, X in the compound having the formula (1) is an organic radical which has only one quaternary nitrogen atom which has, as counterion, fluoride, chloride, bromide, iodide, sulfate, hydrogensulfate, phosphate, dihydrogenphosphate, hydrogenphosphate, tosylate, mesylate, formate, acetate, oxalate, benzoate, citrate and/or mixtures thereof.

The object of the present invention is likewise achieved by the provision of a process for preparing a compound as claimed in claim 1, wherein the process comprises the following steps:

(A) reducing a substituted nitroaniline of the formula (22) to a substituted o-phenylenediamine of the formula (23)

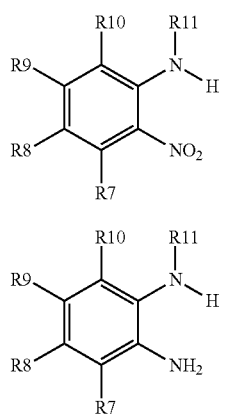

where each of the R7 to R10 radicals, which may be the same or different, is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula $-(C(D)(E))_h$-OH, $-(C(D)(E))_k$-aryl-$(C(D)(E))_l$-OH, $-(C(D)(E))_h$-X or $-(C(D)(E))_k$-aryl-$(C(D)(E))_l$-X, and where the R11 radical is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula $-(C(D)(E))_h$-OH or $-(C(D)(E))_k$-aryl-$(C(D)(E))_l$-OH, $-(C(D)(E))_h$-X or $-(C(D)(E))_k$-aryl-$(C(D)(E))_l$-X, (B) condensing the substituted o-phenylenediamine of the formula (23) obtained in step (A) with alloxane or the hydrate thereof to obtain a compound having the formula (24):

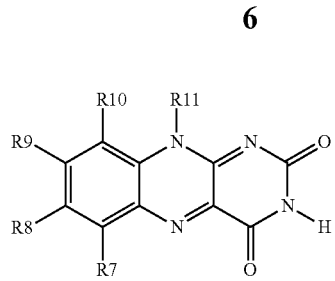

(C) optionally reacting the compound of the formula (24) obtained in step (B) with an alkylating agent of the general formula T-alkyl, T-alkenyl, T-cycloalkyl, T-cycloalkenyl, T-$(C(D)(E))_h$-OH, T-$(C(D)(E))_k$-aryl-$(C(D)(E))_l$-OH, T-aryl, T-$(C(D)(E))_h$-X or T-$(C(D)(E))_k$-aryl-$(C(D)(E))_l$-X, where the T radical is hydrogen, chlorine, bromine, iodine, p-toluenesulfonyl (OTs), methanesulfonyl (OMs), OH or $R_2S^+$, where R may be the same or different and is independently preferably methyl, ethyl, propyl or butyl, to obtain a compound having the formula (25):

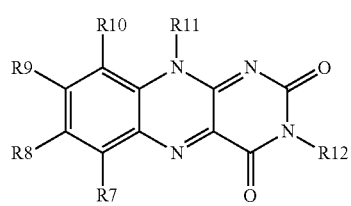

(D) optionally reacting the compound of the formula (24) obtained in step (B) or the compound of the formula (25) obtained in step (C) with tosyl chloride, mesyl chloride or iodine, optionally in the presence of a catalyst, and subsequently with an organic compound containing at least one tertiary nitrogen atom, when none of the R7 to R12 radicals is an organic radical of the general formula $-(C(D)(E))_h$-X or $-(C(D)(E))_k$-aryl-$(C(D)(E))_l$-X and when 1 R7 to R12 radical is an organic radical of the general formula $-(C(D)(E))_h$-OH or $-(C(D)(E))_k$-aryl-$(C(D)(E))_l$-OH, to obtain the inventive 10H-benzo[g]pteridine-2,4-dione derivative of the formula (1), with the proviso that only 1 R7 to R12 radical is an organic radical of the general formula $-(C(D)(E))_h$-X or $-(C(D)(E))_k$-aryl-$(C(D)(E))_l$-X, and where h is an integer from 1 to 20 and k, l are each independently an integer from 0 to 6, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having only one quaternary nitrogen atom and aryl is a substituted or unsubstituted aromatic system or a substituted or unsubstituted heteroaromatic system which does not contain any nitrogen atom.

The object of the present invention is likewise achieved by the provision of a process for preparing a compound as claimed in claim 1, wherein the process comprises the following steps:

(A) condensing an amine having the formula R11-$NH_2$ with a chlorouracil derivative of the formula (26), optionally in the presence of a catalyst, preferably Lewis acid or Brønsted acid, to obtain a compound having the formula (27):

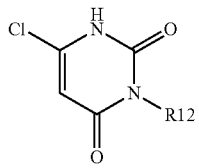
(26)

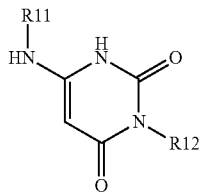
(27)

where each of the R11 or R12 radicals may be the same or different and is independently hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula -(C(D)(E))$_h$-OH or -(C(D)(E))$_k$-aryl-(C(D)(E))$_l$-OH, -(C(D)(E))$_h$-X or -(C(D)(E))$_k$-aryl-(C(D)(E))$_l$-X, (B) reacting the compound of the formula (27) obtained in step (A) with a nitroso compound of the formula (28) to obtain a compound of the formula (25):

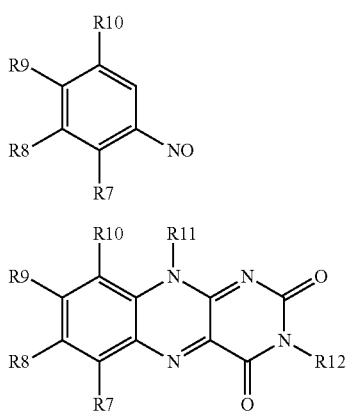
(28)

(25)

where each of the R7 to R10 radicals may be the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula -(C(D)(E))$_h$-OH, -(C(D)(E))$_k$-aryl-(C(D)(E))$_l$-OH, -(C(D)(E))$_h$-X or -(C(D)(E))$_k$-aryl-(C(D)(E))$_l$-X, and (C) optionally reacting the compound of the formula (23) obtained in step (B) with tosyl chloride, mesyl chloride or iodine, optionally in the presence of a catalyst, and subsequently with an organic compound containing at least one tertiary nitrogen atom, when none of the R7 to R12 radicals is an organic radical of the general formula -(C(D)(E))$_h$-X or -(C(D)(E))$_k$-aryl-(C(D)(E))$_l$-X and when 1 R7 to R12 radical is an organic radical of the general formula -(C(D)(E))$_h$-OH or -(C(D)(E))$_k$-aryl-(C(D)(E))$_l$-OH, to obtain the inventive 10H-benzo[g]pteridine-2,4-dione derivative of the formula (1), with the proviso that only 1 R7 to R12 radical is an organic radical of the general formula -(C(D)(E))$_h$-X or -(C(D)(E))$_k$-aryl-(C(D)(E))$_l$-X, and where h is an integer from 1 to 20 and k, l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having only one quaternary nitrogen atom and aryl is a substituted or unsubstituted aromatic system or a substituted or unsubstituted heteroaromatic system which does not contain any nitrogen atom.

Further preferred embodiments of the present invention are described in the dependent claims.

In a further-preferred embodiment, the inventive 10H-benzo[g]pteridine-2,4-dione derivative of the formula (1) does not contain any basic, preferably uncharged, protonatable and/or positively charged, nitrogen atoms or any further quaternary nitrogen atoms.

According to the invention, "photosensitizer" is understood to mean compounds which absorb electromagnetic radiation, preferably visible light, UV light and/or infrared light, and then generate reactive oxygen species (ROS), preferably free radicals and/or singlet oxygen, from triplet oxygen.

According to the invention, the term "photodynamic therapy" is understood to mean the light-induced inactivation of cells or microorganisms.

According to the invention, the term "inactivation" is understood to mean the reduction of the viability or the destruction of a microorganism, preferably the destruction thereof. A light-induced inactivation can be determined, for example, via reduction in the number of microorganisms after irradiation of a defined starting amount of these microorganisms in the presence of at least one inventive compound having the formula (1).

According to the invention, a reduction in viability is understood to mean that the number of microorganisms is reduced by at least 99.0%, preferably by at least 99.9%, further preferably by at least 99.99%, further preferably by at least 99.999%, even further preferably by at least 99.9999%. Exceptionally preferably, the number of microorganisms is reduced by more than 99.9 to 100%, preferably by more than 99.99 to 100%.

Preferably, the reduction in the number of microorganisms is reported as the log$_{10}$ reduction factor according to Boyce, J. M. and Pittet, D. ("Guidelines for hand hygiene in healthcare settings. Recommendations of the Healthcare Infection Control Practices Advisory Committee and the HIPAC/SHEA/APIC/IDSA Hand Hygiene Task Force", Am. J. Infect. Control 30 (8), 2002, pages 1-46).

According to the invention, the term "$\log_{10}$ reduction factor" is understood to mean the difference between the decadic logarithm of the number of microorganisms before and the decadic logarithm of the number of microorganisms after an irradiation of these microorganisms with electromagnetic radiation in the presence of at least one inventive compound having the formula (1).

Suitable methods for determining the $\log_{10}$ reduction factor are described, for example, in DIN EN 14885:2007-01 "Chemical disinfectants and antiseptics—Application of European Standards for chemical disinfectants and antiseptics" or in Rabenau, H. F. and Schwebke, I. ("Leitlinie der Deutschen Vereinigung zur Bekämpfung der Viruskrankheiten (DVV) e.V. und des Robert Koch-Instituts (RKI) zur Prüfung von chemischen Desinfektionsmitteln auf Wirksamkeit gegen Viren in der Humanmedizin" Bundesgesundheitsblatt, Gesundheitsforschung, Gesundheitschutz 51(8), (2008), pages 937-945).

Preferably, the $\log_{10}$ reduction factor after irradiation of microorganisms with electromagnetic radiation in the presence of at least one inventive compound having the formula (1) is at least 2 $\log_{10}$, preferably at least 3 $\log_{10}$, further preferably at least 4 $\log_{10}$, further preferably at least 4.5 $\log_{10}$, further preferably at least 5 $\log_{10}$, further preferably at least 6 $\log_{10}$, even further preferably at least 7 $\log_{10}$, even further preferably at least 7.5 $\log_{10}$.

For example, a reduction in the number of microorganisms after irradiation of these microorganisms with electromagnetic radiation in the presence of at least one inventive compound having the formula (1) by 2 orders of magnitude, based on the starting amount of these microorganisms, means a $\log_{10}$ reduction factor of 2 $\log_{10}$.

Further preferably, the number of microorganisms after irradiation of these microorganisms with electromagnetic radiation in the presence of at least one inventive compound having the formula (1) is reduced by at least 1 order of magnitude, further preferably by at least 2 orders of magnitude, preferably by at least 4 orders of magnitude, further preferably by at least 5 orders of magnitude, further preferably by at least 6 orders of magnitude, even further preferably by at least 7 orders of magnitude, based in each case on the starting amount of these microorganisms.

The term "microorganisms" in the context of the invention is understood to mean especially viruses, archaea, prokaryotic microorganisms such as bacteria and bacterial spores, and eukaryotic microorganisms such as fungi, protozoa, fungal spores, monocellular algae. The microorganisms may occur in monocellular or polycellular form, for example as a fungal mycelium.

An inventive 10H-benzo[g]pteridine-2,4-dione derivative has the formula (1)

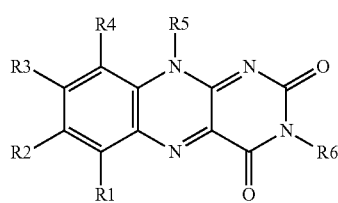

(1)

where either R10
A) only 1 R1, R2, R3 or R4 radical is an organic radical of the general formula -(C(D)(E))$_h$-X or -(C(D)(E))$_k$-aryl-(C(D)(E))$_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, where aryl is a substituted or unsubstituted aromatic system having 5 to 20 carbon atoms or a substituted or unsubstituted heteroaromatic system which does not contain any nitrogen atom and has 4 to 20 carbon atoms, and where X is an organic radical having only one quaternary nitrogen atom,
or
B) only 1 R5 or R6 radical is an organic radical of the general formula -(C(D)(E))$_h$-X or -(C(D)(E))$_k$-aryl-(C(D)(E))$_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, where aryl is a substituted or unsubstituted aromatic system having 5 to 20 carbon atoms or a substituted or unsubstituted heteroaromatic system which does not contain any nitrogen atom and has 4 to 20 carbon atoms, and where X is an organic radical having only one quaternary nitrogen atom.

In a preferred embodiment, the inventive 10H-benzo[g]pteridine-2,4-dione derivative of the formula (1) does not have any uncharged, protonatable nitrogen atom bonded directly to the isoalloxazine ring, for example in the form of an amino radical, methylamino radical or dimethylamino radical, or any positively charged nitrogen atom bonded directly to the isoalloxazine ring, for example in the form of a pyridin-1-ium-1-yl radical or trimethylammonio radical.

Further preferably, the organic radical X does not contain any basic nitrogen atoms, preferably no uncharged protonatable nitrogen atom and/or no protonatable, positively charged nitrogen atom.

In variant A) of the inventive 10H-benzo[g]pteridine-2,4-dione derivative of the formula (1), only 1 R1, R2, R3 or R4 radical is an organic radical of the general formula -(C(D)(E))$_h$-X or -(C(D)(E))$_k$-aryl-(C(D)(E))$_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, where aryl is a substituted or unsubstituted aromatic system having 5 to 20 carbon atoms or a substituted or unsubstituted heteroaromatic system which does not contain any nitrogen atom and has 4 to 20 carbon atoms, and where X is an organic radical having only one quaternary nitrogen atom, where the R1, R2, R3 or R4 radicals which are not -(C(D)(E))$_h$-X or -(C(D)(E))$_k$-aryl-(C(D)(E))$_l$-X may each independently be the same or different and are hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals is the same or different and is independently hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms.

In variant B) of the inventive 10H-benzo[g]pteridine-2,4-dione derivative of the formula (1), only 1 R5 or R6 radical is an organic radical of the general formula -(C(D)(E))$_h$-X or -(C(D)(E))$_k$-aryl-(C(D)(E))$_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, where aryl is a substituted or unsubstituted aromatic system having 5 to 20 carbon atoms or a substituted or unsubstituted heteroaromatic system which does not contain any nitrogen atom and has 4 to 20 carbon atoms, and where X is an organic radical having only one quaternary nitrogen atom, where the R5 or R6 radical which is not -(C(D)(E))$_h$-X or -(C(D)(E))$_k$-aryl-(C(D)(E))$_l$-X is hydrogen, alkyl having 1 to 20 carbon atoms, alkenyl having 2 to 20 carbon atoms, cycloalkyl having 3 to 20 carbon atoms, cycloalkenyl having 3 to 20 carbon atoms, ether having 2 to 20 carbon atoms, thioether having 2 to 20 carbon atoms, aryl having 5 to 20 carbon atoms or heteroaryl having 4 to 20 carbon atoms, which does not contain any nitrogen atoms, and where the R1 to R4 radicals may be the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms.

In a further preferred embodiment of the inventive 10H-benzo[g]pteridine-2,4-dione derivative of the formula (1), either A) only 1 R1, R$^2$, R$^3$ or R$^4$ radical is an organic radical of the general formula -(C(D)(E))$_h$-X or -(C(D)(E))$_k$-aryl-(C(D)(E))$_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, where X is an organic radical containing only one quaternary nitrogen atom and aryl is a substituted or unsubstituted aromatic system having 5 to 20 carbon atoms or a substituted or unsubstituted heteroaromatic system which does not contain any nitrogen atom and has 4 to 20 carbon atoms, and where the R1, R2, R3 or R4 radicals which are not an organic radical of the general formula -(C(D)(E))$_h$-X or -(C(D)(E))$_k$-aryl-(C(D)(E))$_l$-X are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms, and where the R5 radical is an acyclic polyol radical of the general formula —CH$_2$(CH(OH))$_g$CH$_2$OH or an ether, ester or acetal thereof, where g is an integer from 1 to 10, preferably 1 to 4, and where R6 is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or B) only the R6 radical is an organic radical of the general formula -(C(D)(E))$_h$-X or -(C(D)(E))$_k$-aryl-(C(D)(E))$_l$-X, where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, where X is an organic radical containing only one quaternary nitrogen atom and aryl is a substituted or unsubstituted aromatic system having 5 to 20 carbon atoms or a substituted or unsubstituted heteroaromatic system which does not contain any nitrogen atom and has 4 to 20 carbon atoms, where the R5 radical is an acyclic polyol radical of the general formula —CH$_2$(CH(OH))$_g$CH$_2$OH or an ether, ester or acetal thereof, where g is an integer from 1 to 10, preferably 1 to 4, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms.

Further preferably, the R5 radical is an acyclic polyol radical selected from the group consisting of arabityl, ribityl, xylityl, erythrityl, threityl, lactityl, mannityl and sorbityl, further preferably D-ribityl and D-arabityl, or an ether, ester or acetal thereof.

In a further preferred embodiment of the inventive 10H-benzo[g]pteridine-2,4-dione derivative of the formula (1), only the R5 radical is an acyclic polyol radical of the general formula —CH$_2$(CH(OZ))$_f$CH$_{(3-e)}$(OZ)$_e$ where e is 0, 1 or 2 and f is an integer from 1 to 10, preferably 1 to 4, and where Z is hydrogen, alkyl having 1 to 20 carbon atoms, carboxylic ester having 1 to 20 carbon atoms or an X radical, where X is an organic radical having only one quaternary nitrogen atom, with the proviso that only 1 Z radical is an organic X radical having only one quaternary nitrogen atom, where R6 is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms.

In a preferred embodiment of the 10H-benzo[g]pteridine-2,4-dione derivative of the formula (1), the organic X radical having only one quaternary nitrogen atom is a radical of the general formula (2):

where A is an oxygen or sulfur atom and where n is an integer from 1 to 8 and m is an integer from 0 to 100, preferably 0-59, preferably 0-10, and where B is a radical of the formula (3), (4a), (4b), (5a) or (5b):

and where each of the R$^{(I)}$, R$^{(II)}$, R$^{(III)}$, R$^{(IV)}$ and R$^{(V)}$ radicals is independently an aryl radical having 5 to 20 carbon atoms, an alkyl radical which may be straight-chain or branched and has 1 to 20 carbon atoms, an alkenyl radical which may be straight-chain or branched and has 2 to 20 carbon atoms, a hydroxyalkyl radical which may be straight-chain or branched and has 1 to 20 carbon atoms, an ether radical which may be straight-chain or branched and has 2 to 20 carbon atoms, or a thioether radical which may be straight-chain or branched and has 2 to 20 carbon atoms, and where the R$^{(VI)}$ radical is hydrogen, an aryl radical having 5 to 20 carbon atoms, an alkyl radical which may be straight-chain or branched and has 1 to 20 carbon atoms, an alkenyl radical which may be straight-chain or branched and has 2 to 20 carbon atoms, a hydroxyalkyl radical which may be straight-chain or branched and has 1 to 20 carbon atoms, an ether radical which may be straight-chain or branched and has 2 to 20 carbon atoms, or a thioether radical which may be straight-chain or branched and has 2 to 20 carbon atoms, and where the radical having the formula (4a) and the radical having the formula (5a):

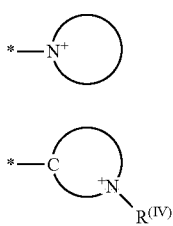

(4a)

(5a)

is a substituted or unsubstituted heterocyclic radical having 5 to 7 ring atoms including 1 nitrogen atom and at least 1 carbon atom and optionally 1 or 2 oxygen or sulfur atoms, where 1 nitrogen atom forms a double bond, and where the radical having the formula (4b) and the radical having the formula (5b):

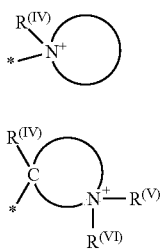

(4b)

(5b)

is a substituted or unsubstituted heterocyclic radical having 5 to 7 ring atoms including 1 nitrogen atom and at least 1 carbon atom and optionally 1 or 2 oxygen or sulfur atoms.

In a further preferred embodiment, the radical of the formula (5a) is selected from the group consisting of radicals of the formulae (7a), (7b) and (7c):

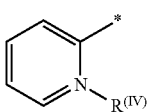

(7a)

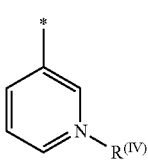

(7b)

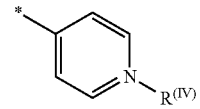

(7c)

where each $R^{(IV)}$ is an aryl radical having 5 to 20 carbon atoms, for example phenyl or benzyl, alkyl radical which may be straight-chain or branched and has 1 to 20 carbon atoms, for example methyl, ethyl, n-propyl, i-propyl, n-butyl or t-butyl, alkenyl radical which may be straight-chain or branched and has 2 to 20 carbon atoms, hydroxyalkyl radical which may be straight-chain or branched and has 1 to 20 carbon atoms, for example hydroxymethyl, 2-hydroxyethyl, 3-hydroxypropyl or 1-hydroxy-1-methylethyl, ether radical which may be straight-chain or branched and has 2 to 20 carbon atoms, for example methoxymethyl, methoxyethyl, methoxypropyl, ethoxymethyl, ethoxyethyl, ethoxypropyl, propoxymethyl, propoxyethyl or propoxypropyl, or thioether radical which may be straight-chain or branched and has 2 to 20 carbon atoms, for example methylsulfanylmethyl, ethylsulfanylmethyl, 2-ethylsulfanylethyl or 3-methylsulfanylpropyl.

In a further preferred embodiment, the radical of the formula (4a) is selected from the group consisting of radicals of the formulae (8a), (8b) and (8c):

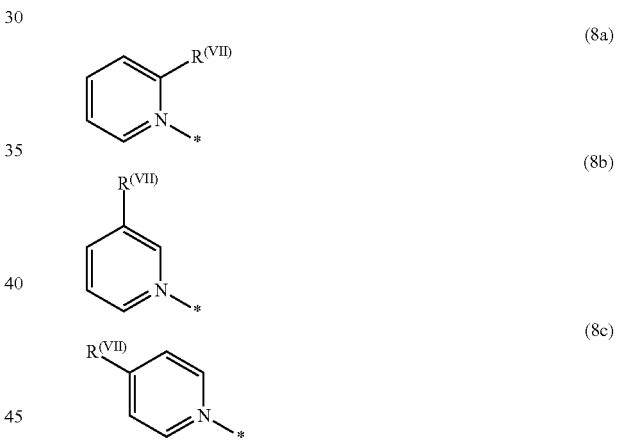

where each $R^{(VII)}$ is hydrogen, an aryl radical having 5 to 20 carbon atoms, for example phenyl or benzyl, an alkyl radical which may be straight-chain or branched and has 1 to 20 carbon atoms, for example methyl, ethyl, n-propyl, i-propyl, n-butyl or t-butyl, an alkenyl radical which may be straight-chain or branched and has 2 to 20 carbon atoms, a hydroxyalkyl radical which may be straight-chain or branched and has 1 to 20 carbon atoms, for example hydroxymethyl, 2-hydroxyethyl, 3-hydroxypropyl or 1-hydroxy-1-methylethyl, an ether radical which may be straight-chain or branched and has 2 to 20 carbon atoms, for example methoxymethyl, methoxyethyl, methoxypropyl, ethoxymethyl, ethoxyethyl, ethoxypropyl, propoxymethyl, propoxyethyl or propoxypropyl, or a thioether radical which may be straight-chain or branched and has 2 to 20 carbon atoms, for example methylsulfanylmethyl, ethylsulfanylmethyl, 2-ethylsulfanylethyl or 3-methylsulfanylpropyl.

In a further preferred embodiment, the radical of the formula (4b) is 1-methylpyrrolidin-1-ium-1-yl, 1-methylpiperazin-1-ium-1-yl or 4-methylmorpholin-4-ium-4-yl.

In a further preferred embodiment, the $R^{(I)}$, $R^{(II)}$, $R^{(III)}$, $R^{(IV)}$ and $R^{(V)}$ radicals are each independently selected from the group consisting of hydrogen and alkyl groups of the general formula —$(CH_2)_n$—$CH_3$ where n is an integer from 0 to 19, preferably from 1 to 17.

In a further preferred embodiment, the $R^{(I)}$, $R^{(II)}$, $R^{(III)}$, $R^{(IV)}$ and $R^{(V)}$ radicals are each independently selected from the group consisting of hydrogen, methyl, ethyl, prop-1-yl, prop-2-yl, but-1-yl, but-2-yl, 2-methylprop-1-yl, 2-methylprop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl and 2,3-dimethylbut-2-yl.

In a particularly preferred embodiment, the $R^{(I)}$, $R^{(II)}$, $R^{(III)}$, $R^{(IV)}$ and $R^{(V)}$ radicals are each independently selected from the group consisting of methyl, ethyl, prop-1-yl, but-1-yl, pent-1-yl, hex-1-yl, hept-1- and oct-1-yl.

In a further preferred embodiment, the $R^{(I)}$, $R^{(II)}$, $R^{(III)}$, $R^{(IV)}$ and $R^{(V)}$ radicals are each independently hydrogen or the radical having the formula (10):

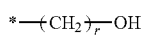

(10)

where each r is an integer from 1 to 20, preferably from 1 to 8, further preferably from 1 to 4.

In a further preferred embodiment of the inventive 10H-benzo[g]pteridine-2,4-dione derivative of the formula (1), the organic radical of the general formula -(C(D)(E))$_h$-X is selected from the group consisting of the radicals of the formulae (12a) to (15b)

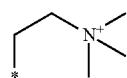

(12a)

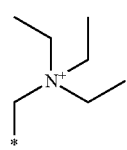

(12b)

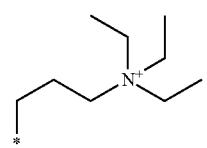

(12c)

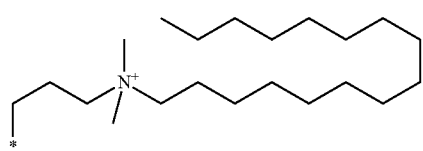

(12d)

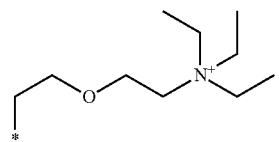

(13)

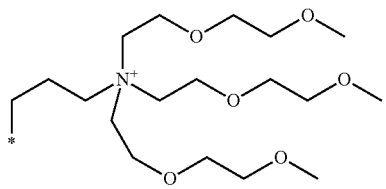

(14)

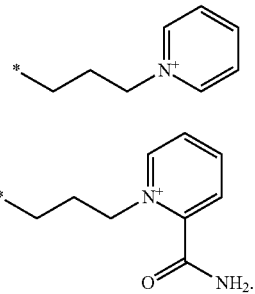

(15a)

(15b)

In a further-preferred embodiment, the R1 and R4 radicals, which may be the same or different, are each independently hydrogen or methyl, and only 1 R2, R3, R5 or R6 radical is an organic radical of the general formula -(C(D)(E))$_h$-X or -(C(D)(E))$_k$-aryl-(C(D)(E))$_l$-X, where h is an integer from 1 to 20 and k, l are each independently an integer from 0 to 6, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having only one quaternary nitrogen atom and aryl is a substituted or unsubstituted aromatic system or a substituted or unsubstituted heteroaromatic system which does not contain any nitrogen atom.

In a further preferred embodiment, the inventive 10H-benzo[g]pteridine-2,4-dione derivative of the formula (1) is selected from the group consisting of the compounds having the formulae (30) to (43):

(30)

-continued
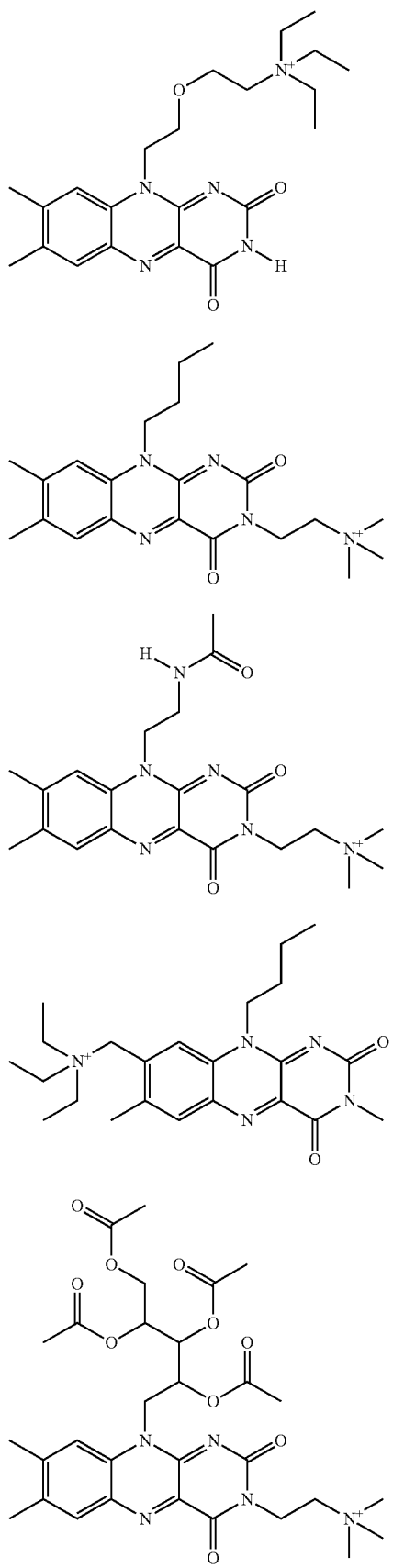
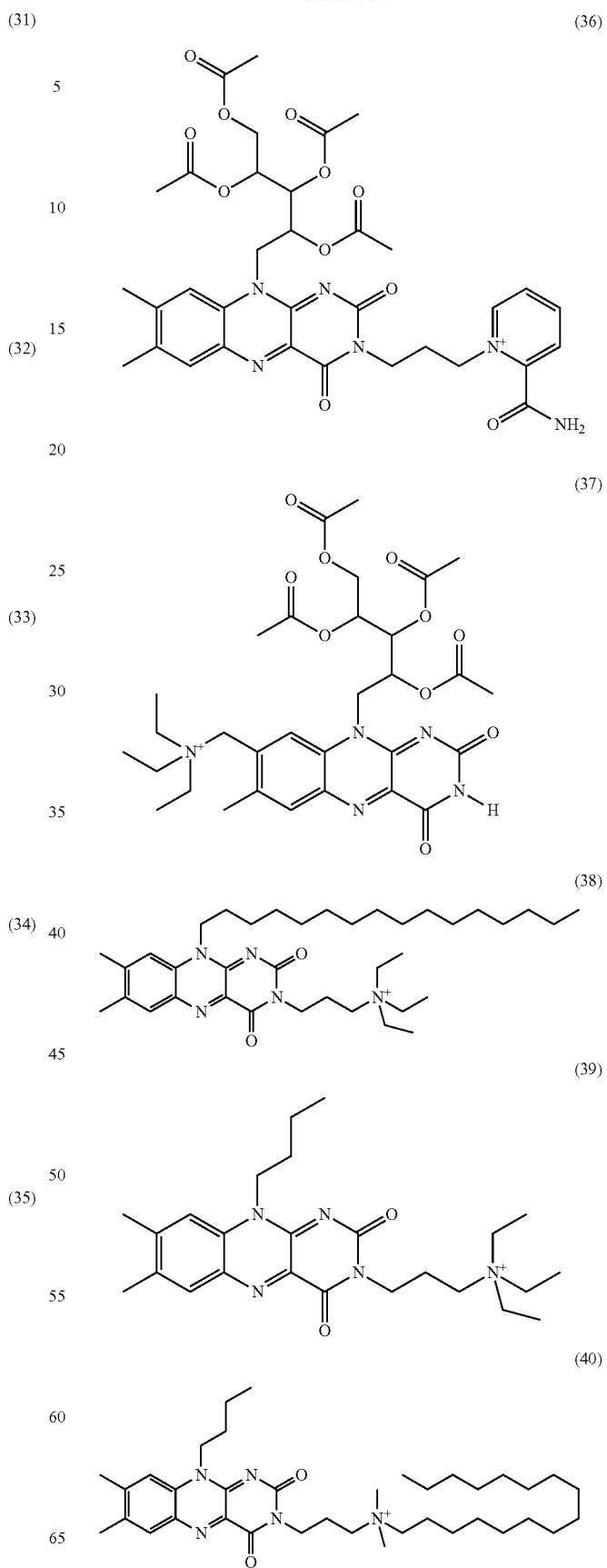

(41)

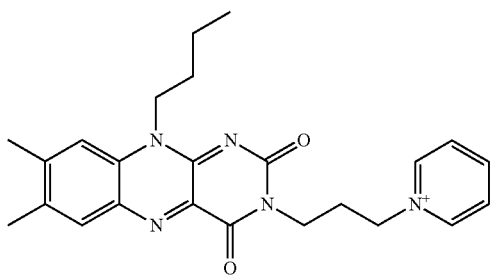

(42)

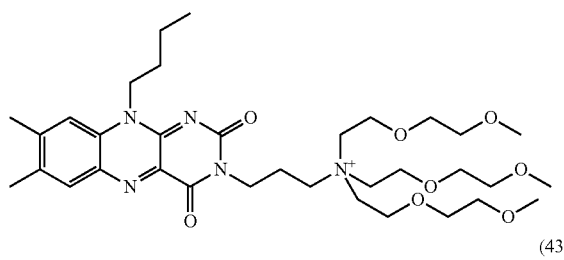

(43)

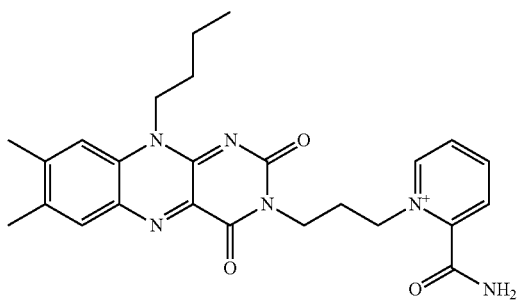

In the inventive 10H-benzo[g]pteridine-2,4-dione derivative of the formula (1), the aforementioned aldehyde radicals, ketone radicals, carboxylic acid radicals, carboxamide radicals, thioester radicals, cycloalkyl radicals, cycloalkenyl radicals, alkyl radicals and alkenyl radicals may be straight-chain or branched, preferably straight-chain, and either be unsubstituted or substituted by at least one radical which is halogen, preferably chlorine, bromine, iodine or fluorine, thiol, nitro, hydroxyl, sulfanyl, alkyloxy, preferably methoxy, ethoxy, n-propyloxy, i-propyloxy, n-butyloxy or n-pentyloxy, alkylsulfanyl, preferably methylsulfanyl, ethylsulfanyl, n-propylsulfanyl, i-propylsulfanyl, n-butylsulfanyl or n-pentylsulfanyl or alkanoyloxy, preferably formyloxy, acetoxy or n-propanoyloxy.

In a further-preferred embodiment, the aforementioned alkyl radicals are each selected from the group consisting of methyl, ethyl, n-propyl, n-butyl, n-pentyl, n-hexyl, n-heptyl and n-octyl.

In a further-preferred embodiment, the aforementioned alkyl radicals may be acyclic polyol radicals of the general formula —$CH_2(CH(OH))CH_2OH$ where g is an integer from 1 to 10, preferably 1 to 4. Further preferably, the acyclic polyol radicals are selected from the group consisting of arabityl, ribityl, xylityl, erythrityl, threityl, lactityl, mannityl and sorbityl, further preferably D-ribityl and D-arabityl.

In the inventive 10H-benzo[g]pteridine-2,4-dione derivative of the formula (1), the aforementioned cycloalkyl radicals and cycloalkenyl radicals may have oxygen and/or sulfur atoms as ring atoms and either be unsubstituted or substituted by at least one radical which is from hydroxyl, sulfanyl, alkyloxy, preferably methoxy, ethoxy, n-propyloxy, i-propyloxy, n-butyloxy or n-pentyloxy, alkylsulfanyl, preferably methylsulfanyl, ethylsulfanyl, n-propylsulfanyl, i-propylsulfanyl, n-butylsulfanyl or n-pentylsulfanyl or alkanoyloxy, preferably formyloxy, acetoxy or n-propanoyloxy.

In a further-preferred embodiment, the aforementioned cycloalkyl radicals and cycloalkenyl radicals having oxygen and/or sulfur atoms as ring atoms are each selected from the group consisting of tetrahydrofuranyl, tetrahydrothiophenyl, tetrahydropyranyl, tetrahydrothiopyranyl, dioxolanyl and dioxanyl.

In a preferred embodiment of the inventive 10H-benzo[g]pteridine-2,4-dione derivative of the formula (1), the aryl radicals each have not more than 4, further preferably not more than 3, further preferably not more than 2, fused rings. Even further preferably, the aryl radicals each have 1 ring.

In a preferred embodiment of the inventive 10H-benzo[g]pteridine-2,4-dione derivative of the formula (1), the aforementioned aryl radicals are selected from the group consisting of phenyl, benzyl, naphthyl, anthracenyl, phenanthenyl and pyrenyl.

In a preferred embodiment of the inventive 10H-benzo[g]pteridine-2,4-dione derivative of the formula (1), the aforementioned alkenyl radicals have 2 to 17 carbon atoms, further preferably 2 to 13 carbon atoms, further preferably 2 to 9 carbon atoms, further preferably 2 to 5 carbon atoms. In a further-preferred embodiment, the aforementioned alkenyl radicals are selected from the group consisting of ethenyl, n-propenyl and n-butenyl.

In a further preferred embodiment of the inventive 10H-benzo[g]pteridine-2,4-dione derivative of the formula (1), the aforementioned aldehydes have 1 to 17 carbon atoms, further preferably 1 to 13 carbon atoms, further preferably 1 to 9 carbon atoms, further preferably 1 to 5 carbon atoms. In a further-preferred embodiment, the aforementioned aldehydes are selected from the group consisting of methanal-1-yl (formyl), ethanal-1-yl (2-oxoethyl), n-propanal-1-yl (3-oxopropyl) and n-butanal-1-yl (4-oxobutyl).

In a further preferred embodiment of the inventive 10H-benzo[g]pteridine-2,4-dione derivative of the formula (1), the aforementioned ketones have 2 to 17 carbon atoms, further preferably 3 to 14 carbon atoms, further preferably 3 to 9 carbon atoms. In a further-preferred embodiment, the aforementioned ketones are selected from the group consisting of dimethyl ketyl, methyl ethyl ketyl, ethyl methyl ketyl, diethyl ketyl, methyl propyl ketyl, ethyl propyl ketyl, propyl methyl ketyl, propyl ethyl ketyl and dipropyl ketyl, which may be straight-chain or branched.

In a further-preferred embodiment, the aforementioned aldehyde radicals and/or ketone radicals may be monosaccharide radicals, preferably pentose or ketose radicals.

Preferably, suitable monosaccharide radicals have 3 to 7 carbon atoms, preferably 5 to 6 carbon atoms, and have one carbonyl group, preferably aldehyde group or keto group, and at least one hydroxyl group and may be open-chain or cyclic, preferably in the form of furanose or pyranose.

Preferably, suitable monosaccharide radicals derive from monosaccharides selected from the group consisting of D-glyceraldehyde, L-glyceraldehyde, D-erythrose, L-erythrose, D-threose, L-threose, D-ribose, L-ribose, D-arabinose, L-arabinose, D-xylose, L-xylose, D-lyxose, L-lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, dihydroxyacetone, D-erythrulose, L-erythrulose, D-ribulose, L-ribulose, D-xylulose, L-xylulose, D-psicose, L-psicose, D-fructose, L-fructose, D-sorbose, L-sorbose, D-tagatose and L-tagatose. Further preferably, suitable monosaccharides are selected from the group consisting of D-ribose, L-ribose, D-arabinose, L-arabinose, D-xylose, L-xylose, D-lyxose, L-lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, D-ribulose, L-ribulose, D-xylulose, L-xylulose, D-psicose, L-psicose, D-fructose, L-fructose, D-sorbose, L-sorbose, D-tagatose and L-tagatose.

In a further preferred embodiment of the inventive 10H-benzo[g]pteridine-2,4-dione derivative of the formula (1), the aforementioned carboxylic esters have 1 to 17 carbon atoms, further preferably 1 to 15 carbon atoms, further preferably 1 to 12 carbon atoms. In a further-preferred embodiment, the aforementioned carboxylic esters are selected from the group consisting of ethyl esters, n-propyl esters, i-propyl esters, n-butyl esters, sec-butyl esters, tert-butyl esters and benzyl esters.

In a further preferred embodiment of the inventive 10H-benzo[g]pteridine-2,4-dione derivative of the formula (1), the aforementioned carboxamides have 1 to 17 carbon atoms, further preferably 1 to 15 carbon atoms, further preferably 1 to 12 carbon atoms. In a further-preferred embodiment, the aforementioned carboxamides are selected from the group consisting of amide, N-methylamide, N-ethylamide, N-(n-propyl)amide, N-(i-propyl)amide, N-(n-butyl)amide, N-(sec-butyl)amide, N-(tert-butyl)amide, N-phenylamide, N-benzylamide, N,N-dimethylamide, N-methyl-N-ethylamide, N,N-diethylamide, N-methyl-N-(n-propyl)amide, N-methyl-N-(i-propyl)amide, N-methyl-N-(n-butyl)amide, N-methyl-N-(sec-butyl)amide, N-methyl-N-(tert-butyl)amide, N-ethyl-N-(n-propyl)amide, N-ethyl-N-(i-propyl)amide, N-ethyl-N-(n-butyl)amide, N-ethyl-N-(sec-butyl)amide, N-ethyl-N-(tert-butyl)amide, N-(n-propyl)-N-(n-propyl)amide, N-(n-propyl)-N-(i-propyl)amide, N-(n-propyl)-N-(n-butyl)amide, N-(n-propyl)-N-(sec-butyl)amide, N-(n-propyl)-N-(tert-butyl)amide, N-(i-propyl)-N-(n-propyl)amide, N-(i-propyl)-N-(i-propyl)amide, N-(i-propyl)-N-(n-butyl)amide, N-(i-propyl)-N-(sec-butyl)amide, N-(i-propyl)-N-(tert-butyl)amide, N-(n-butyl)-N-(n-propyl)amide, N-(n-butyl)-N-(i-propyl)amide, N-(n-butyl)-N-(n-butyl)amide, N-(n-butyl)-N-(sec-butyl)amide, N-(n-butyl)-N-(tert-butyl)amide, N-(sec-butyl)-N-(n-propyl)amide, N-(sec-butyl)-N-(i-propyl)amide, N-(sec-butyl)-N-(n-butyl)amide, N-(sec-butyl)-N-(sec-butyl)amide, N-(sec-butyl)-N-(tert-butyl)amide, N-(tert-butyl)-N-(n-propyl)amide, N-(tert-butyl)-N-(i-propyl)amide, N-(tert-butyl)-N-(n-butyl)amide, N-(tert-butyl)-N-(sec-butyl)amide, N-(tert-butyl)-N-(tert-butyl)amide, N,N-diphenylamide, N,N-dibenzylamide, N-phenyl-N-benzylamide, N-methyl-N-phenylamide, N-methyl-N-benzylamide, N-ethyl-N-phenylamide, N-ethyl-N-benzylamide, N-phenyl-N-(n-propyl)amide, N-phenyl-N-(i-propyl)amide, N-phenyl-N-(n-butyl)amide, N-phenyl-N-(sec-butyl)amide, N-phenyl-N-(tert-butyl)amide, N-benzyl-N-(n-propyl) amide, N-benzyl-N-(i-propyl)amide, N-benzyl-N-(n-butyl) amide, N-benzyl-N-(sec-butyl)amide and N-benzyl-N-(tert-butyl)amide.

In a further preferred embodiment of the inventive 10H-benzo[g]pteridine-2,4-dione derivative of the formula (1), the aforementioned heteroaryl radical which does not contain any nitrogen atom and has 4 to 20 carbon atoms is selected from the group consisting of thiophenyl, furanyl, benzothiofuranyl and benzofuranyl.

In a further preferred embodiment of the inventive 10H-benzo[g]pteridine-2,4-dione derivative of the formula (1), the aforementioned ether radicals have 2 to 17 carbon atoms, further preferably 2 to 13 carbon atoms, further preferably 2 to 9 carbon atoms. In a further-preferred embodiment, the aforementioned ether radicals are selected, for example, from the group consisting of methoxymethyl, methoxyethyl, methoxy-n-propyl, ethoxymethyl, n-propoxymethyl, 2-ethoxyethoxymethyl, 2-(2-ethoxyethoxy)ethyl, i-propoxymethyl, tert-butyloxymethyl, dioxa-3,6-heptyl and benzyloxymethyl. In a further-preferred embodiment, the aforementioned ether radicals may be simple ether radicals, oligoether radicals, polyether radicals or mixtures thereof.

In a further preferred embodiment of the inventive 10H-benzo[g]pteridine-2,4-dione derivative of the formula (1), the aforementioned thioether radicals have 2 to 17 carbon atoms, further preferably 2 to 13 carbon atoms, further preferably 2 to 9 carbon atoms. In a further-preferred embodiment, the aforementioned thioether radicals are selected, for example, from the group methylsulfanylmethyl, methylsulfanylethyl, 3-methylsulfanyl-n-propyl, ethylsulfanylmethyl, n-propylsulfanylmethyl, 2-ethylsulfanylethylsulfanylmethyl, 2-(2-ethylsulfanylethylsulfanyl)ethyl, 2-methylsulfanylpropyl, tert-butylsulfanylmethyl and benzylsulfanylmethyl consists.

In a further preferred embodiment, the inventive 10H-benzo[g]pteridine-2,4-dione derivative of the formula (1) has a molecular weight of less than 1300 g/mol, preferably less than 990 g/mol, further preferably less than 810 g/mol, further preferably less than 690 g/mol, even further preferably less than 610 g/mol, even further preferably less than 600 g/mol, even further preferably less than 570 g/mol.

Chiral centers, unless stated otherwise, may be in the R or S configuration. The invention relates both to the optically pure compounds and to stereoisomer mixtures, such as enantiomer mixtures and diastereomer mixtures, in any ratio.

The invention preferably also relates to mesomers and/or tautomers of the compound having the formula (1), both the pure compounds and the isomer mixtures in any ratio.

In a further preferred embodiment, the inventive 10H-benzo[g]pteridine-2,4-dione derivative of the formula (1) is selected from the group consisting of the compounds having the formulae (30) to (43):

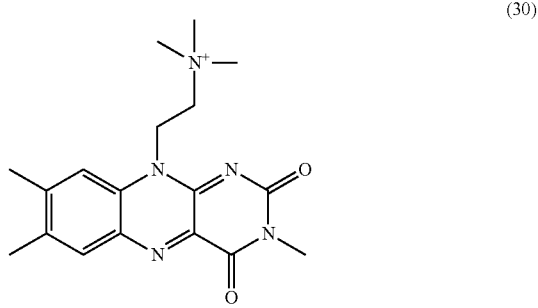

(30)

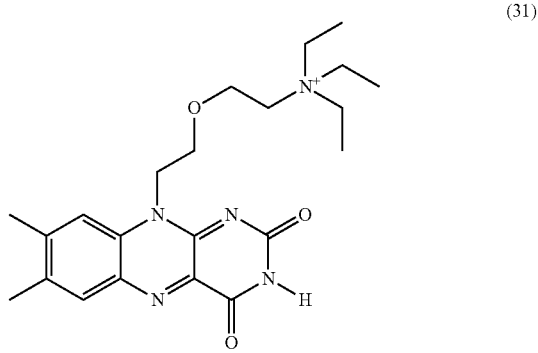

(31)

-continued
(32)
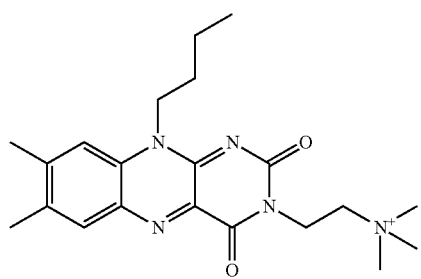
(34)
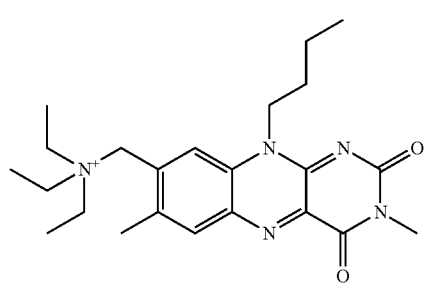
(35)
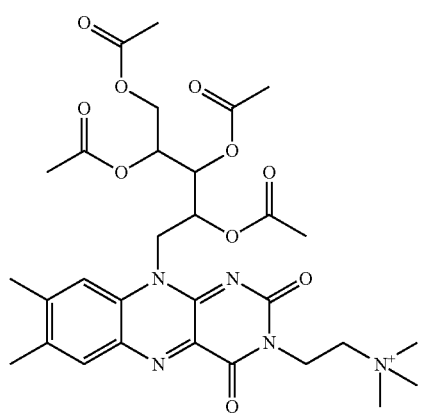
(36)
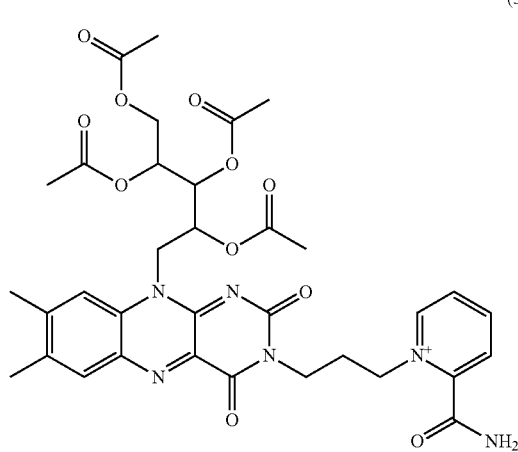
-continued
(37)
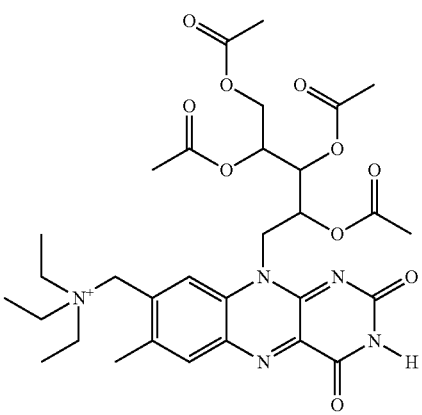
(38)
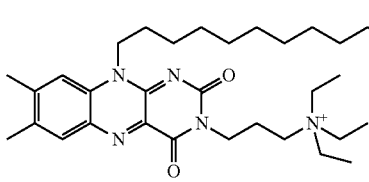
(39)
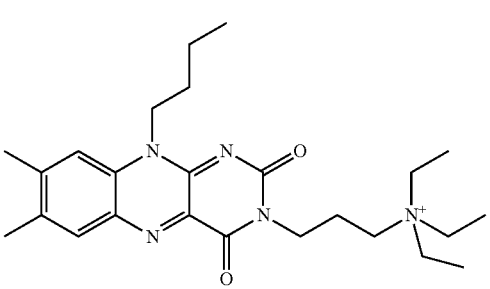
(40)
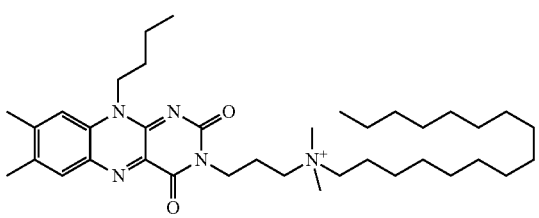
(41)
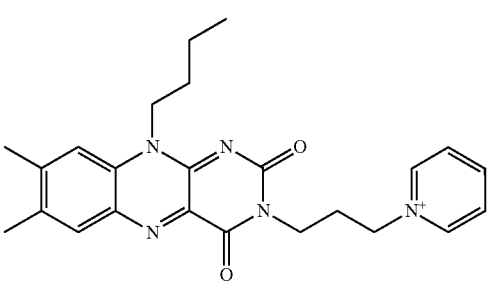

-continued (42)

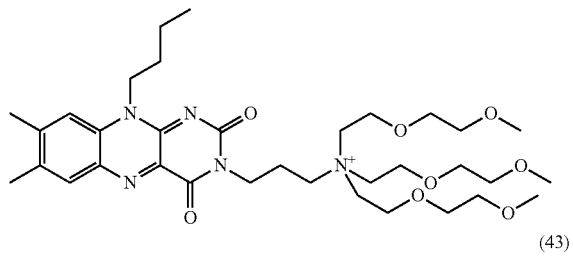

(43)

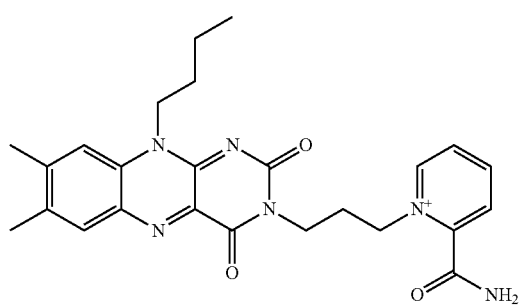

One variant of the process according to the invention for preparing a 10H-benzo[g]pteridine-2,4-dione derivative of the formula (1) comprises the following steps:

(A) reducing a substituted nitroaniline of the formula (22) to a substituted o-phenylenediamine of the formula (23), preferably by means of hydrogen and palladium on activated carbon or with tin(II) chloride, (22)

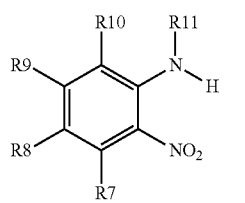

(23)

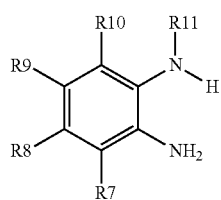

where each of the R7 to R10 radicals, which may be the same or different, is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula -(C(D)(E))$_h$-OH, -(C(D)(E))$_k$-aryl-(C(D)(E))$_l$-OH, -(C(D)(E))$_h$-X or -(C(D)(E))$_k$-aryl-(C(D)(E))$_l$-X, and where the R11 radical is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atom, or an organic radical of the general formula -(C(D)(E))$_h$-OH or -(C(D)(E))$_k$-aryl-(C(D)(E))$_l$-OH, -(C(D)(E))$_h$-X or -(C(D)(E))$_k$-aryl-(C(D)(E))$_l$-X, (B) condensing the substituted o-phenylenediamine of the formula (23) obtained in step (A) with alloxane or the hydrate thereof to obtain a compound having the formula (24), optionally in the presence of a catalyst, preferably Lewis acid or Brønsted acid, further preferably acetic acid in the presence of boric acid (24)

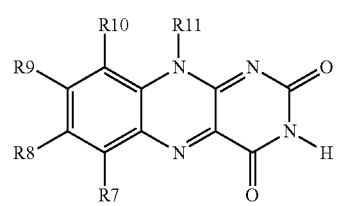

(C) optionally reacting the compound of the formula (24) obtained in step (B) with an alkylating agent of the general formula T-alkyl, T-alkenyl, T-cycloalkyl, T-cycloalkenyl, T-(C(D)(E))$_h$-OH, T-(C(D)(E))$_k$-aryl-(C(D)(E))$_l$-OH, T-aryl, T-(C(D)(E))$_h$-X or T-(C(D)(E))$_k$-aryl-(C(D)(E))$_l$-X, where the T radical is hydrogen, chlorine, bromine, iodine, p-toluenesulfonyl (OTs), methanesulfonyl (OMs), OH or R$_2$S$^+$, where each R may be the same or different and is independently preferably methyl, ethyl, propyl or butyl, to obtain a compound having the formula (25):

(25)

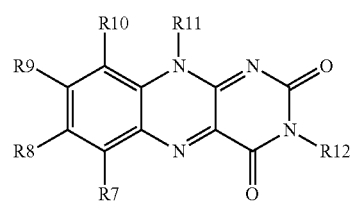

(D) optionally reacting the compound of the formula (24) obtained in step (B) or the compound of the formula (25) obtained in step (C) with tosyl chloride, mesyl chloride or iodine, optionally in the presence of a catalyst, and subsequently with an organic compound containing at least one tertiary nitrogen atom, when none of the R7 to R12 radicals is an organic radical of the general formula -(C(D)(E))$_h$-X or -(C(D)(E))$_k$-aryl-(C(D)(E))$_l$-X and when 1 R7 to R12 radical is an organic radical of the general formula -(C(D)(E))$_h$-OH or -(C(D)(E))$_k$-aryl-(C(D)(E))$_l$-OH, to obtain the inventive 10H-benzo[g]pteridine-2,4-dione derivative of the formula (1), with the proviso that only 1 R1 to R6 radical is an organic radical of the general formula -(C(D)(E))$_h$-X or -(C(D)(E))$_k$-aryl-(C(D)(E))$_l$-X, and where each h is an integer from 1 to 20 and k, l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where each X is an organic radical having only one quaternary nitrogen atom and each aryl is a substituted or unsubstituted aromatic system having 5 to 20 carbon atoms or a substituted or unsubstituted heteroaromatic system which does not contain any nitrogen atom and has 4 to 20 carbon atoms.

A further variant of the process according to the invention for preparing a 10H-benzo[g]pteridine-2,4-dione derivative of the formula (1) comprises the following steps:

(A) preparing a substituted aniline having the formula (102a) or (102b) by (a) peptide coupling/reduction to an aniline having the formula (101) or (b) reductive amination of an aniline having the formula (101) with aldehydes or (c) Pd-catalyzed coupling of a halide of the formula (104) to an amines of the formula R11-NH$_2$ or (d) Pd-catalyzed coupling of an amine of the formula (100) to a halide of the formula R11-NH$_2$

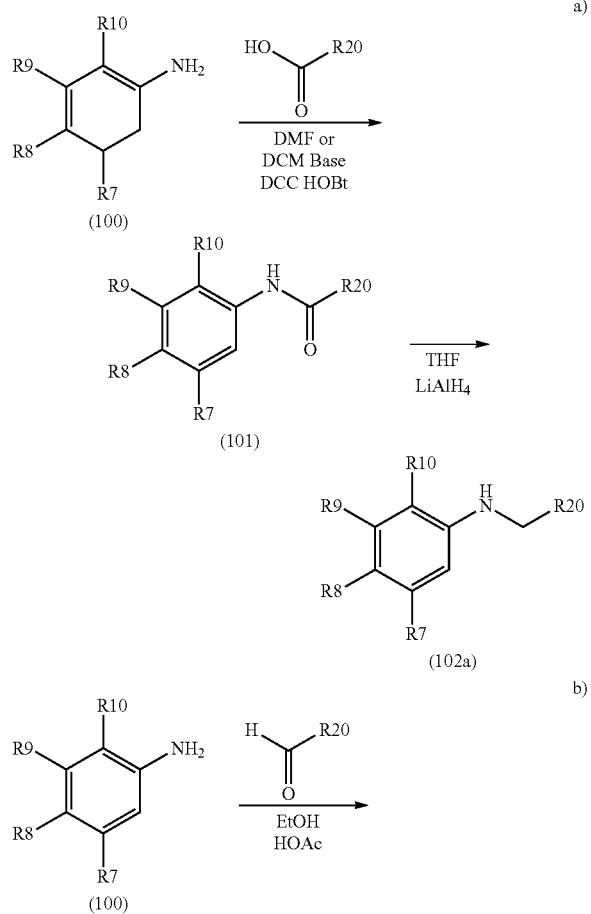
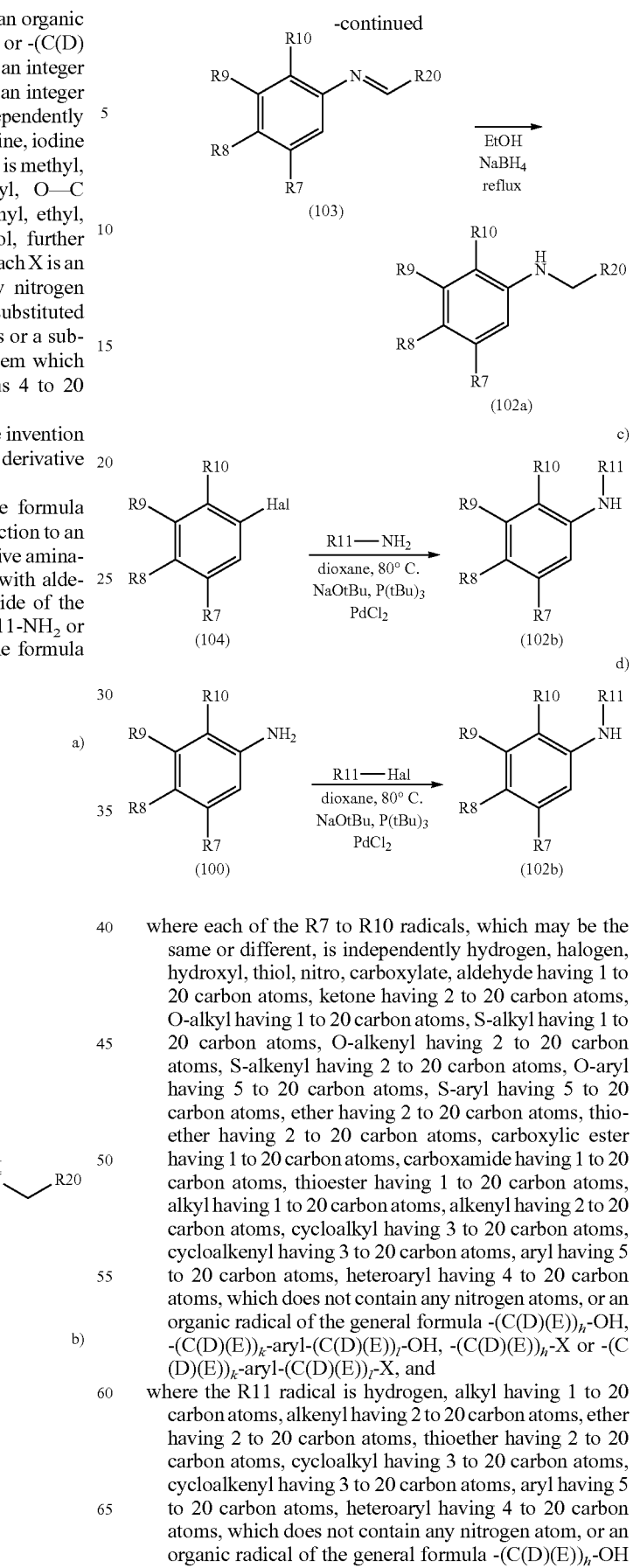

where each of the R7 to R10 radicals, which may be the same or different, is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula -(C(D)(E))$_h$-OH, -(C(D)(E))$_k$-aryl-(C(D)(E))$_l$-OH, -(C(D)(E))$_h$-X or -(C(D)(E))$_k$-aryl-(C(D)(E))$_l$-X, and where the R11 radical is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atom, or an organic radical of the general formula -(C(D)(E))$_h$-OH or -(C(D)(E))$_k$-aryl-(C(D)(E))$_l$-OH, -(C(D)(E))$_h$-X or -(C(D)(E))$_k$-aryl-(C(D)(E))$_l$-X, and where the R20 radical is hydrogen, alkyl having 1 to 19 carbon atoms, alkenyl having 2 to 19 carbon atoms, ether having 1 to 19 carbon atoms, thioether having 1 to 19 carbon atoms, cycloalkyl having 3 to 19 carbon atoms, cycloalkenyl having 3 to 19 carbon atoms, aryl having 5 to 19 carbon atoms, heteroaryl having 4 to 19 carbon atoms, which does not contain any nitrogen atom, or an organic radical of the general formula -(C(D)(E))$_{h-1}$-OH or -(C(D)(E))$_{k-1}$-aryl-(C(D)(E))$_{l-1}$-OH, -(C(D)(E))$_{h-1}$-X or -(C(D)(E))$_{k-1}$-aryl-(C(D)(E))$_{l-1}$-X, and where the Hal radical is fluorine, chlorine, bromine or iodine, (B) reacting the substituted aniline having the formula (102a) obtained in step (A) with violuric acid to obtain a compound of the formula (24z):

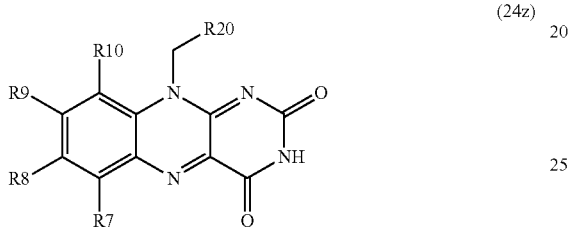

(24z)

or reacting the substituted aniline having the formula (102b) obtained in step (A) with violuric acid to obtain a compound of the formula (24):

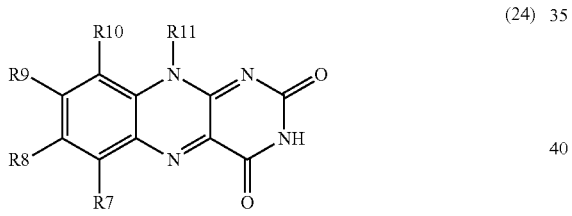

(24)

(C) optionally reacting the compound of the formula (24z) obtained in step (B) with an alkylating agent of the general formula T-alkyl, T-alkenyl, T-cycloalkyl, T-cycloalkenyl, T-(C(D)(E))$_h$-OH, T-(C(D)(E))$_k$-aryl-(C(D)(E))$_l$-OH, T-aryl, T-(C(D)(E))$_h$-X or T-(C(D)(E))$_k$-aryl-(C(D)(E))$_l$-X, where the T radical is hydrogen, chlorine, bromine, iodine, p-toluenesulfonyl (OTs), methanesulfonyl (OMs), OH or R$_2$S$^+$, where each R may be the same or different and is independently preferably methyl, ethyl, propyl or butyl, to obtain a compound having the formula (25z):

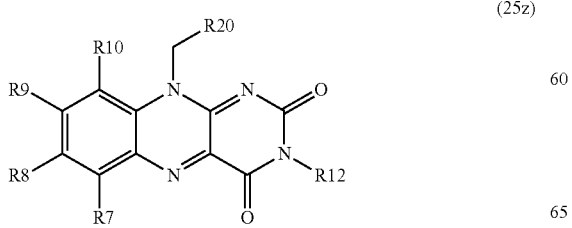

(25z)

or reacting the compound of the formula (24) obtained in step (B) with an alkylating agent of the general formula T-alkyl, T-alkenyl, T-cycloalkyl, T-cycloalkenyl, T-(C(D)(E))$_h$-OH, T-(C(D)(E))$_k$-aryl-(C(D)(E))$_l$-OH, T-aryl, T-(C(D)(E))$_h$-X or T-(C(D)(E))$_k$-aryl-(C(D)(E))$_l$-X, where the T radical is hydrogen, chlorine, bromine, iodine, p-toluenesulfonyl (OTs), methanesulfonyl (OMs), OH or R$_2$S$^+$, where each R may be the same or different and is independently preferably methyl, ethyl, propyl or butyl, to obtain a compound having the formula (25):

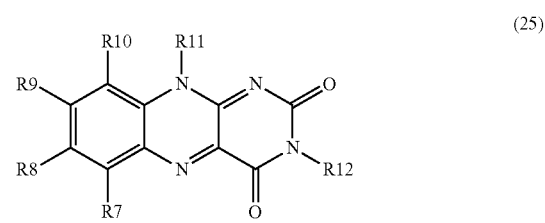

(25)

(D) optionally reacting the compound of the formula (24z) or (24) obtained in step (B) or the compound of the formula (25z) or (25) obtained in step (C) with tosyl chloride, mesyl chloride or iodine, optionally in the presence of a catalyst, and subsequently with an organic compound containing at least one tertiary nitrogen atom, when none of the R7 to R12 or R7 to R11 and R20 radicals is an organic radical of the general formula -(C(D)(E))$_h$-X or -(C(D)(E))$_k$-aryl-(C(D)(E))$_l$-X and when 1 R7 to R12 or R7 to R11 or R20 radical is an organic radical of the general formula -(C(D)(E))$_h$-OH or -(C(D)(E))$_k$-aryl-(C(D)(E))$_l$-OH, to obtain the inventive 10H-benzo[g]pteridine-2,4-dione derivative of the formula (1), with the proviso that only 1 R1 to R6 radical is an organic radical of the general formula -(C(D)(E))$_h$-X or -(C(D)(E))$_k$-aryl-(C(D)(E))$_l$-X and where each h is an integer from 1 to 20 and k, l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where each X is an organic radical having only one quaternary nitrogen atom and each aryl is a substituted or unsubstituted aromatic system having 5 to 20 carbon atoms or a substituted or unsubstituted heteroaromatic system which does not contain any nitrogen atom and has 4 to 20 carbon atoms.

A further variant of the process according to the invention for preparing a 10H-benzo[g]pteridine-2,4-dione derivative of the formula (1) comprises the following steps:

(A) condensing an amine having the formula R11-NH$_2$ with a chlorouracil derivative of the formula (26), optionally in the presence of a catalyst, preferably Lewis acid or Brønsted acid, to obtain a compound having the formula (27):

(26)

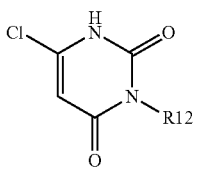

(27)

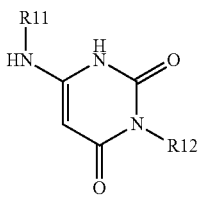

where each of the R11 or R12 radicals may be the same or different and is independently hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula -(C(D)(E))$_h$-OH or -(C(D)(E))$_k$-aryl-(C(D) (E))$_l$-OH, -(C(D)(E))$_h$-X or -(C(D)(E))$_k$-aryl-(C(D)(E))$_l$-X, (B) reacting the compound of the formula (27) obtained in step (A) with a nitroso compound of the formula (28) to obtain a compound of the formula (25):

(28)

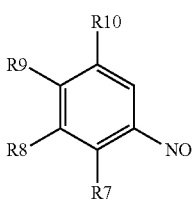

(25)

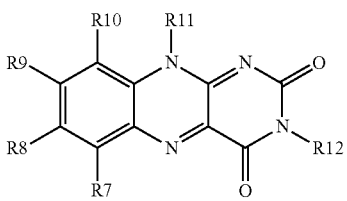

where each of the R7 to R10 radicals may be the same or different and is independently hydrogen, halogen, hydroxyl, thiol, nitro, carboxyl, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula -(C(D)(E))$_h$-OH, -(C(D)(E))$_k$-aryl-(C(D)(E))$_l$-OH, -(C(D)(E))$_h$-X or -(C(D)(E))$_k$-aryl-(C(D)(E))$_l$-X, and (C) optionally reacting the compound of the formula (25) obtained in step (B) with tosyl chloride, mesyl chloride or iodine, optionally in the presence of a catalyst, and subsequently with an organic compound containing at least one tertiary nitrogen atom, when none of the R7 to R12 radicals is an organic radical of the general formula -(C(D)(E))$_h$-X or -(C(D)(E))$_k$-aryl-(C(D)(E))$_l$-X and when 1 R7 to R12 radical is an organic radical of the general formula -(C(D)(E))$_h$-OH or -(C(D)(E))$_k$-aryl-(C(D)(E))$_l$-OH, to obtain the inventive 10H-benzo[g]pteridine-2,4-dione derivative of the formula (1), with the proviso that only 1 R7 to R12 radical is an organic radical of the general formula -(C(D)(E))$_h$-X or -(C(D)(E))$_k$-aryl-(C(D)(E))$_l$-X, and where h is an integer from 1 to 20 and k, l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having only one quaternary nitrogen atom and aryl is a substituted or unsubstituted aromatic system or a substituted or unsubstituted heteroaromatic system which does not contain any nitrogen atom.

In a preferred embodiment of the two process variants, none of the R7 to R12 or R7 to R11 and R20 radicals is an organic radical of the general formula -(C(D)(E))$_h$-X or -(C(D)(E))$_k$-aryl-(C(D)(E))$_l$-X and 1 R7 to R10 radical is methyl, in which case the process may comprise the following steps:

(A) free-radically halogenating the compound (24) or (25) in the presence of a free-radical initiator, preferably of a peroxide or of an azo compound, to obtain a compound having the formula (24a-d) or (25a-d):

(24a)

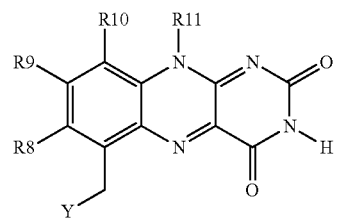

(24b)

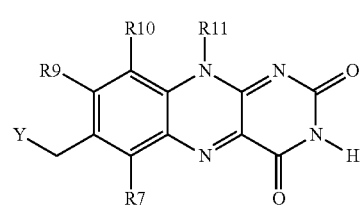

(24c)

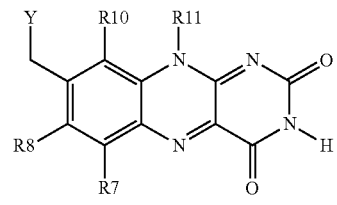

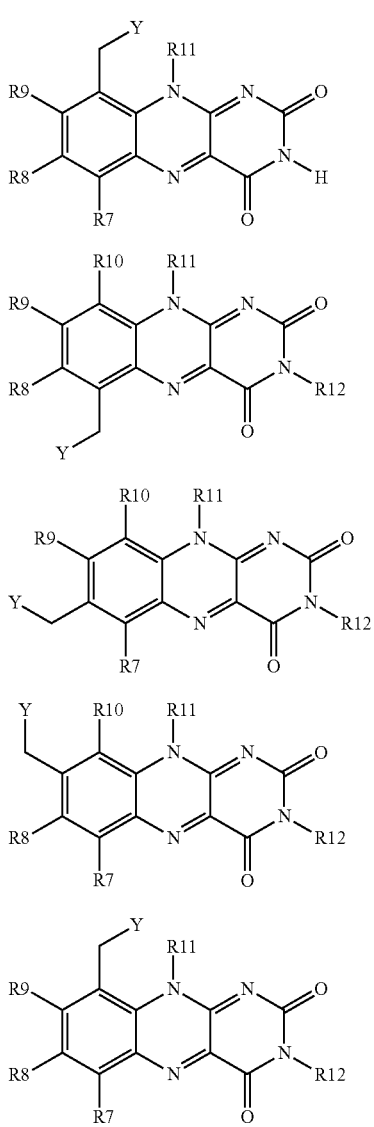

where the Y radical is Cl, Br or I, and

B) reacting the compound obtained in step (A) and having the formula (24a-d) or (25a-d) with an organic compound containing at least one tertiary nitrogen atom to obtain the inventive 10H-benzo[g]pteridine-2,4-dione derivative of the formula (1).

When different amino protecting groups PG are used in a synthesis, there is the option of an orthogonal protecting group strategy, in which case different amino functions in one molecule can be selectively released and are reacted in succession.

Suitable methods for removing the amino protecting group PG are known from the prior art. For example, benzyloxycarbonyl (Cbz) can be removed again by catalytic hydrogenation with hydrogenolytic scission of the benzyl-heteroatom bond with subsequent decarboxylation of the unstable carbamic acid thus formed or treatment with acids. Di-tert-butyloxycarbonyl (Boc) can be removed, for example, by acidic hydrolysis.

Allyloxycarbonyl (Alloc) can be removed, for example, by the action of tetrakis(triphenylphosphine)palladium(0) and a nucleophile.

In a further preferred embodiment, steps (B) and/or (C) take place in the presence of one or more solvents. Step (B) can be performed, for example, in the presence of dichloromethane (DCM) or tetrahydrofuran (THF), preferably in the presence of a base, for example potassium carbonate. Alternatively, step (B) can be performed, for example, in the presence of dimethylformamide (DMF) and triphenylphosphine (PPh3) and/or potassium iodide.

Step (C) can be performed, for example, in the presence of water/dichloromethane or toluene/tetrabutylammonium iodide (TBAI).

Unicellular or multicellular microorganisms may be triggers for infectious diseases. Administration of at least one pathogen-specific antidote, for example antibiotic, antimycotic or virustatic can reduce the number of pathogens and/or inactivate the pathogen. A pathogen-specific antidote can be administered systemically and/or topically.

In the case of systemic administration, the pathogen-specific antidote is transferred to the blood system and/or lymph system of the body to be treated and is distributed over the entire body in this way. In the case of systemic administration of the pathogen-specific antidote, there may be degradation of the antidote and/or side effects, for example as a result of a biochemical transformation (metabolization) of the antidote.

In the case of topical administration of pathogen-specific antidote, the antidote is applied where it is to act therapeutically, for example on an infected part of the skin, while the healthy skin is not stressed. Thus, systemic side effects can be substantially avoided.

Superficial skin or soft tissue infections need not necessarily be treated by a systemic administration of pathogen-specific antidote, since the antidote can be applied directly to the infected parts of the skin.

The pathogen-specific antidotes known to date, both in the case of systemic and topical administration, have side effects and interactions, some of them severe. Furthermore, in the case of topical administration too, unreliable taking of medicaments (compliance) on the part of the patient, especially in the case of use of antibiotics, can result in development of resistance.

An alternative here is the photodynamic inactivation of microorganisms, where resistances to photodynamic inactivation are unknown. Irrespective of the nature of the microorganisms to be controlled and the associated infectious diseases, the number of pathogens is reduced and/or the pathogens are killed. For example, mixtures of various microorganisms, for example fungi and bacteria or different bacterial strains, can be controlled.

In a preferred embodiment, at least one 10H-benzo[g]pteridine-2,4-dione derivative of the formula (1) or a pharmacologically compatible salt and/or ester and/or complex thereof is used as a photosensitizer in the photodynamic inactivation of microorganisms, preferably in photodynamic therapy.

The inventive 10H-benzo[g]pteridine-2,4-dione derivative of the formula (1), after irradiation with electromagnetic radiation of suitable wavelength and energy density, has a high yield of singlet oxygen.

The electromagnetic radiation is preferably in the visible spectral region, ultraviolet region and/or infrared region. Further preferably, the electromagnetic radiation has a wavelength from a range from 280 to 1000 nm, further preferably from 380 to 1000 nm.

Further preferably, the electromagnetic radiation has an energy density from a range from 1 µW/cm² to 1 MW/cm², further preferably from 1 mW/cm² to 1 kW/cm².

The irradiation time can be varied as a function of the nature of the microorganisms and/or the severity of the infection. The irradiation time is preferably within a range from 1 µs to 1 h, further preferably from 1 ms to 1000 s.

Preferably, the electromagnetic radiation is generated by a radiation source selected from the group consisting of the sun and artificial radiation sources, for example UV lamp, IR lamp, phosphor lamps, light-emitting diodes, lasers or chemical light. Furthermore, the inventors have found that, surprisingly, the inventive 10H-benzo[g]pteridine-2,4-dione derivative of the formula (1) or pharmacologically acceptable salts and/or esters and/or complexes thereof preferably has a high affinity for microorganisms.

On account of the affinity, the inventive 10H-benzo[g]pteridine-2,4-dione derivative of the formula (1) can bind effectively to microorganisms and produce sufficient singlet oxygen locally to inactivate, preferably kill, the microorganisms.

In this preferred use as a photosensitizer, at least one inventive 10H-benzo[g]pteridine-2,4-dione derivative of the formula (1) is bound by microorganisms. After irradiation with electromagnetic radiation of suitable wavelength and energy density, the microorganisms are inactivated, preferably killed, by the reactive oxygen species (ROS) formed, preferably oxygen radicals and/or singlet oxygen.

Preferably, the binding of at least one inventive 10H-benzo[g]pteridine-2,4-dione derivative of the formula (1) to microorganisms likewise allows staining or localization of microorganisms. In this way, it is preferably also possible to monitor the progress of the inactivation of microorganisms or of the decolonization.

According to the invention, the term "decolonization" is understood to mean the removal, preferably complete removal, of microorganisms.

In a further preferred embodiment, at least one inventive 10H-benzo[g]pteridine-2,4-dione derivative of the formula (1) or a pharmacologically acceptable salt and/or ester and/or complex thereof is used in the inactivation of unicellular or multicellular microorganisms preferably selected from the group consisting of viruses, archaea, bacteria, bacterial spores, fungi, for example mycelium fungi and yeasts, fungal spores, protozoa, algae and blood-transmissible parasites.

It is possible with preference to treat surfaces of the body, for example the skin or mucous membrane, of humans and animals, preferably mammals. In this preferred embodiment, at least one inventive 10H-benzo[g]pteridine-2,4-dione derivative of the formula (1) or a pharmacologically acceptable salt and/or ester and/or complex thereof, preferably in a pharmaceutical formulation, is used in the disinfection and/or decolonization of surfaces of skin or soft tissue, preferably with preservation of skin integrity.

In a further preferred embodiment, at least one inventive 10H-benzo[g]pteridine-2,4-dione derivative of the formula (1) or a pharmacologically acceptable salt and/or ester and/or complex thereof is present in a pharmaceutical formulation for topical, preferably nasal, oral, anal, vaginal or dermal, administration.

Topical administration is also understood to mean application on or in the ear, preferably the outer ear. The outer ear comprises the ear cartilage, the pinna, the earlobe and the outer auditory canal or else ear canal, and the outside of the eardrum.

In a further preferred embodiment, at least one inventive 10H-benzo[g]pteridine-2,4-dione derivative of the formula (1) or a pharmacologically acceptable salt and/or ester and/or complex thereof is used for production of a pharmaceutical formulation in the prophylaxis and/or treatment of an infectious, preferably viral, bacterial and/or mycotic, skin disease which is preferably selected from the group consisting of staphylococcal scalded skin syndrome, impetigo, skin abscess, furuncle, carbuncle, phlegmon, cellulitis, acute lymphadenitis, pilonidal cysts, pyoderma, purulent dermatitis, septic dermatitis, suppurative dermatitis, erythrasma, erysipelas, acne vulgaris and fungal infection.

In a further preferred embodiment, at least one inventive 10H-benzo[g]pteridine-2,4-dione derivative of the formula (1) or a pharmacologically acceptable salt and/or ester and/or complex thereof is used for production of a pharmaceutical formulation in wound healing, for example in the event of disrupted healing after surgical interventions.

Preferably, at least one inventive 10H-benzo[g]pteridine-2,4-dione derivative of the formula (1) or a pharmacologically acceptable salt and/or ester and/or complex thereof, or a pharmaceutical formulation comprising at least one inventive 10H-benzo[g]pteridine-2,4-dione derivative of the formula (1) or a pharmacologically acceptable salt and/or ester and/or complex thereof is used in the disinfection and/or reduction of the microbe count in infected wounds.

In a further preferred embodiment, at least one inventive 10H-benzo[g]pteridine-2,4-dione derivative of the formula (1) or a pharmacologically acceptable salt and/or ester and/or complex thereof is used for production of a pharmaceutical formulation in the prophylaxis and/or treatment of infectious, preferably viral, bacterial and/or mycotic, disorders of the ear, of the upper respiratory pathway, of the oral cavity, of the throat, of the larynx, of the lower respiratory pathway and/or of the esophagus.

The prevalence of pathogenic microorganisms is, for example, the main cause of infections in the oral cavity. The problem occurs that the microorganisms are organized synergetically in biofilms of extremely complex structure. These biofilms, for example plaque or dental deposits, consist of several layers of complex structure and contain proteins, carbohydrates, phosphates and microorganisms. Dental deposits arise particularly where tooth surfaces cannot be kept free of deposits by natural or artificial cleaning. This fact makes it difficult to find access to the microorganisms incorporated within the biofilm.

Conventional treatments, for example antibiotics and rinse solutions or mechanical tooth cleaning, can be used only to a limited degree, since they do not directly affect the bacteria, for example in the case of tooth cleaving, can be dosed and applied only with difficulty, for example in the case of antibiotics and rinse solutions, or general application is unjustified because of adverse accompanying phenomena.

In a preferred embodiment, at least one inventive 10H-benzo[g]pteridine-2,4-dione derivative of the formula (1) or a pharmacologically compatible salt and/or ester and/or complex thereof is used as a photosensitizer in the photodynamic inactivation of microorganisms in the oral cavity.

In a further preferred embodiment, at least one inventive 10H-benzo[g]pteridine-2,4-dione derivative of the formula (1) or a pharmacologically acceptable salt and/or ester and/or complex thereof is used for production of a pharmaceutical formulation in the treatment and/or prophylaxis of an infectious, preferably viral, bacterial and/or mycotic, disorder of the dental tissue, preferably plaque, caries or pulpitis, and/or infectious, preferably viral, bacterial and/or mycotic, disorder of the periodontium, preferably gingivitis, paradontitis, endodontitis or periimplantitis.

In a further preferred embodiment, at least one inventive 10H-benzo[g]pteridine-2,4-dione derivative of the formula (1) or a pharmacologically acceptable salt and/or ester and/or complex thereof, or a pharmaceutical formulation comprising at least one inventive 10H-benzo[g]pteridine-2,4-dione derivative of the formula (1) or a pharmacologically acceptable salt and/or ester and/or complex thereof, is used in the cleaning of teeth, dentures and/or dental braces.

In a further preferred embodiment, at least one inventive 10H-benzo[g]pteridine-2,4-dione derivative of the formula (1) or a pharmacologically acceptable salt and/or ester and/or complex thereof, or a pharmaceutical formulation comprising at least one inventive 10H-benzo[g]pteridine-2,4-dione derivative of the formula (1) or a pharmacologically acceptable salt and/or ester and/or complex thereof, is used in the nasal decolonization of microorganisms.

For example, methicillin-resistant *Staphylococcus aureus* (MRSA) strains persist for months in the event of nasal colonization, and have a high environmental resistance. Therefore, nasal decolonization, i.e. removal of the microorganisms, generally also reduces colonization in other parts of the body.

The present invention further relates to a pharmaceutical composition comprising at least one inventive 10H-benzo[g]pteridine-2,4-dione derivative of the formula (1) or a pharmacologically acceptable salt and/or ester and/or complex thereof.

The pharmaceutical composition is preferably produced by mixing at least one compound of the formula (1) or a pharmacologically acceptable salt and/or ester and/or complex thereof with one or more physiologically acceptable excipient(s) and converted to a suitable administration form.

A suitable administration form of the inventive pharmaceutical composition is preferably selected from the group consisting of ointment, cream, gel, lotion, shake lotion, solution, for example in droplet or spray form, powder, microcapsule and paste.

The inventive pharmaceutical formulation can be applied topically, preferably nasally, orally, anally, vaginally or dermally.

Useful physiologically acceptable excipients include the pharmaceutically customary liquid or solid fillers and extenders, solvents, emulsifiers, glidants, flavor correctors, dyes and/or buffer substances.

In a further preferred embodiment, the pharmaceutical composition comprises an effective amount of at least one inventive 10H-benzo[g]pteridine-2,4-dione derivative of the formula (1) or of a pharmacologically acceptable salt and/or ester and/or complex thereof, the effective amount being from 0.01 µg to 1000 µg per gram of the composition, preferably from 0.1 µg to 500 µg per gram of the composition.

In a preferred embodiment of the invention, the pharmaceutical composition comprises at least one inventive 10H-benzo[g]pteridine-2,4-dione derivative of the formula (1) or a pharmacologically acceptable salt and/or ester and/or complex thereof and at least one further pharmaceutically active constituent.

Preferably, the at least one further pharmaceutically active constituent is selected from the group consisting of antibiotics, antimycotics, virustatics, antihistamines, sympathomimetics, antihemorrhagics, emollients and skin protection agents, analgesics, disinfectants, immunosera and immunoglobulins, antiparasitic substances, insecticides, repellents and corticosteroids.

In a further preferred embodiment, at least one inventive 10H-benzo[g]pteridine-2,4-dione derivative of the formula (1) or a pharmacologically acceptable salt and/or ester and/or complex thereof, or a pharmaceutical formulation comprising at least one inventive 10H-benzo[g]pteridine-2,4-dione derivative of the formula (1) or a pharmacologically acceptable salt and/or ester and/or complex thereof, is applied by the user him/herself and, optionally, irradiated subsequently with a suitable radiation source which generates electromagnetic radiation of suitable wavelength and energy density.

In a further preferred embodiment, at least one inventive 10H-benzo[g]pteridine-2,4-dione derivative of the formula (1) or a pharmacologically acceptable salt and/or ester and/or complex thereof, or a formulation comprising at least one inventive 10H-benzo[g]pteridine-2,4-dione derivative or a pharmacologically acceptable salt and/or ester and/or complex thereof, is used in the inactivation of microorganisms in medical blood products.

In a preferred embodiment, at least one inventive 10H-benzo[g]pteridine-2,4-dione derivative of the formula (1) or a pharmacologically acceptable salt and/or ester and/or complex thereof is used for inactivation of microorganisms on surfaces of all kinds. Further preferably, the inventive 10H-benzo[g]pteridine-2,4-dione derivative of the formula (1) or a pharmacologically acceptable salt and/or ester and/or complex thereof is used in surface cleaning and/or coating, preferably of medical products, food or drink packaging or hygiene articles.

Further preferably, at least one inventive 10H-benzo[g]pteridine-2,4-dione derivative of the formula (1) or a pharmacologically acceptable salt and/or ester and/or complex thereof is applied to and/or introduced onto surfaces and, optionally, subsequently irradiated with a suitable radiation source which generates electromagnetic irradiation of suitable wavelength and energy density. Preferably, the at least one inventive 10H-benzo[g]pteridine-2,4-dione derivative of the formula (1) or a pharmacologically acceptable salt and/or ester and/or complex thereof brings about "self-disinfection" of the surface during the irradiation.

The irradiation may directly follow the treatment of the surface with at least one inventive 10H-benzo[g]pteridine-2,4-dione derivative of the formula (1) or a pharmacologically acceptable salt and/or ester and/or complex thereof, preferably the application of the at least one inventive 10H-benzo[g]pteridine-2,4-dione derivative of the formula (1) or a pharmacologically acceptable salt and/or ester and/or complex thereof to the surface and/or introduction of the at least one inventive 10H-benzo[g]pteridine-2,4-dione derivative of the formula (1) or a pharmacologically acceptable salt and/or ester and/or complex thereof into the surface, and/or be effected at a later juncture.

Further preferably, articles having thermally limited shelf life are treated, for example articles made from thermoplastics, or articles which are attacked by disinfectants.

Articles having a thermally limited shelf life can, for example, be only inadequately sterilized, since they lose shape or become brittle at relatively high temperatures.

Furthermore, in the event of improper and/or excessive use of disinfectants, development of resistance can result from selection of robust microorganisms when, for example, the active ingredient concentration and contact time and hence the microbe-reducing effect is too low.

In a further-preferred embodiment, at least one inventive 10H-benzo[g]pteridine-2,4-dione derivative of the formula (1) or a pharmacologically acceptable salt and/or ester and/or complex thereof is used for inactivation of microorganisms on surfaces of medical products, preferably invasive medical implements, for example catheters, hollow probes, tubes or needles.

The medical products are preferably selected from wound dressings, bandages, catheters, hollow probes, tubes and needles.

Further preferably, medical products are also understood to mean dental impressions or dentures, for example prostheses, crowns or implants.

Preferably, a treatment of the surface of medical products with at least one 10H-benzo[g]pteridine-2,4-dione derivative of the formula (1) or a pharmacologically acceptable salt and/or ester and/or complex thereof according to the invention and/or coating and/or immobilization of at least one inventive 10H-benzo[g]pteridine-2,4-dione derivative of the formula (1) or a pharmacologically acceptable salt and/or ester and/or complex thereof on the surface of medical products and subsequent irradiation with electromagnetic radiation of suitable wavelength and energy density reduces, preferably prevents, the colonization of microorganisms on the surfaces treated.

The irradiation may directly follow the treatment of the surface with at least one inventive 10H-benzo[g]pteridine-2,4-dione derivative of the formula (1) or a pharmacologically acceptable salt and/or ester and/or complex thereof, preferably the application of the at least one inventive 10H-benzo[g]pteridine-2,4-dione derivative of the formula (1) or a pharmacologically acceptable salt and/or ester and/or complex thereof to the surface and/or introduction of the at least one inventive 10H-benzo[g]pteridine-2,4-dione derivative of the formula (1) or a pharmacologically acceptable salt and/or ester and/or complex thereof into the surface, and/or be effected at a later juncture, before or during the use of the treated medical product.

In a further-preferred use of the at least one inventive 10H-benzo[g]pteridine-2,4-dione derivative of the formula (1) or of a pharmacologically acceptable salt and/or ester and/or complex thereof in wound dressings and/or bandages, for example cotton gauze, irradiation with electromagnetic radiation of suitable wavelength and energy density can be effected during or after the application of a wound dressing and/or bandage comprising at least one inventive 10H-benzo[g]pteridine-2,4-dione derivative of the formula (1) or a pharmacologically acceptable salt and/or ester and/or complex thereof, as a result of which there is a subsequent reduction, preferably inactivation, of microorganisms in the wound region or treated parts of the skin.

In a further preferred embodiment, the wound dressing and/or bandage comprises, as well as at least one inventive 10H-benzo[g]pteridine-2,4-dione derivative of the formula (1) or a pharmacologically acceptable salt and/or ester and/or complex thereof, further constituents, preferably absorbents, for example calcium alginate or polyurethane foam, or further pharmaceutically active substances.

In a further preferred embodiment, at least one inventive 10H-benzo[g]pteridine-2,4-dione derivative of the formula (1) or a pharmacologically acceptable salt and/or ester and/or complex thereof is used for inactivation of microorganisms on surfaces of food and drink packaging.

In a further preferred embodiment, at least one inventive 10H-benzo[g]pteridine-2,4-dione derivative of the formula (1) or a pharmacologically acceptable salt and/or ester and/or complex thereof is used for inactivation of microorganisms in a liquid or a liquid, preferably aqueous, formulation, for example emulsion paint.

The liquid is preferably water.

In this case, at least one inventive 10H-benzo[g]pteridine-2,4-dione derivative of the formula (1) or a pharmacologically acceptable salt and/or ester and/or complex thereof can be used for treatment of water for the drinks and food industry, the pharmaceutical, chemical and cosmetics industry, the electrical industry. In addition, at least one inventive 10H-benzo[g]pteridine-2,4-dione derivative of the formula (1) or a pharmacologically acceptable salt and/or ester and/or complex thereof can be used in drinking water and rainwater treatment, the treatment of wastewater, or in the treatment of water for use in air conditioning.

In this preferred use of at least one inventive 10H-benzo[g]pteridine-2,4-dione derivative of the formula (1) or a pharmacologically acceptable salt and/or ester and/or complex thereof, the liquid or the liquid formulation can subsequently be irradiated with a suitable radiation source which generates electromagnetic radiation of suitable wavelength and energy density. Preferably, the inventive 10H-benzo[g]pteridine-2,4-dione derivative of the formula (1) or a pharmacologically acceptable salt and/or ester and/or complex thereof brings about "self-disinfection" of the liquid or of the liquid formulation during the irradiation.

In a further preferred use of the at least one inventive 10H-benzo[g]pteridine-2,4-dione derivative of the formula (1) or a pharmacologically acceptable salt and/or ester and/or complex thereof, the 10H-benzo[g]pteridine-2,4-dione derivative of the formula (1) or a pharmacologically acceptable salt and/or ester and/or complex thereof may be bound to a solid carrier and thus used as part of a solid matrix. More preferably, at least one inventive 10H-benzo[g]pteridine-2,4-dione derivative of the formula (1) bound to a solid carrier or a pharmacologically acceptable salt and/or ester and/or complex thereof is introduced into the liquid to be treated, preferably water or blood.

A particularly preferred carrier is a polymer which carries at least one inventive 10H-benzo[g]pteridine-2,4-dione derivative of the formula (1) or a pharmacologically acceptable salt and/or ester and/or complex thereof thereon in a covalently bonded manner. This composition, comprising the carrier and at least one inventive 10H-benzo[g]pteridine-2,4-dione derivative of the formula (1) or a pharmacologically acceptable salt and/or ester and/or complex thereof, develops antimicrobial activity as soon as it is exposed to electromagnetic radiation of suitable wavelength and energy density.

The present invention further relates to a coated article which comprises and/or has been coated with at least one inventive 10H-benzo[g]pteridine-2,4-dione derivative of the formula (1) or a pharmacologically acceptable salt and/or ester and/or complex thereof.

The surface of the coated article preferably comprises at least one inventive 10H-benzo[g]pteridine-2,4-dione derivative of the formula (1) or a pharmacologically acceptable salt and/or ester and/or complex thereof.

The coated article can subsequently be irradiated with a suitable radiation source which generates electromagnetic radiation of suitable wavelength and energy density. Preferably, the inventive 10H-benzo[g]pteridine-2,4-dione derivative of the formula (1) or a pharmacologically acceptable salt and/or ester and/or complex thereof brings about "self-disinfection" of the surface of the coated article during the irradiation.

The irradiation may directly follow the treatment of the coated article with at least one inventive 10H-benzo[g]pteridine-2,4-dione derivative of the formula (1) or a pharmacologically acceptable salt and/or ester and/or complex thereof, preferably the application of the at least one inventive 10H-benzo[g]pteridine-2,4-dione derivative of the formula (1) or a pharmacologically acceptable salt and/or ester and/or complex thereof to the surface of the coated article and/or introduction of the at least one inventive 10H-benzo[g]pteridine-2,4-dione derivative of the formula (1) or a pharmacologically acceptable salt and/or ester and/or complex thereof into the surface of the coated article, and/or be effected at a later juncture, preferably before or during the use of the coated article.

Suitable articles are preferably selected from the group consisting of medical products, food and drink packaging, and hygiene articles.

A further preferred embodiment of the coated article, concerns particles coated with at least one inventive 10H-benzo[g]pteridine-2,4-dione derivative of the formula (1) or a pharmacologically acceptable salt and/or ester and/or complex thereof, for example inorganic or organic particles.

Further preferably, the particles comprise at least one inventive 10H-benzo[g]pteridine-2,4-dione derivative of the formula (1) or a pharmacologically acceptable salt and/or ester and/or complex thereof, which is covalently bonded to the particles.

The invention is illustrated hereinafter by figures and examples, without being restricted thereto.

Example 1

Preparation of Various 10H-benzo[g]pteridine-2,4-dione Derivatives

Overview of the Syntheses:

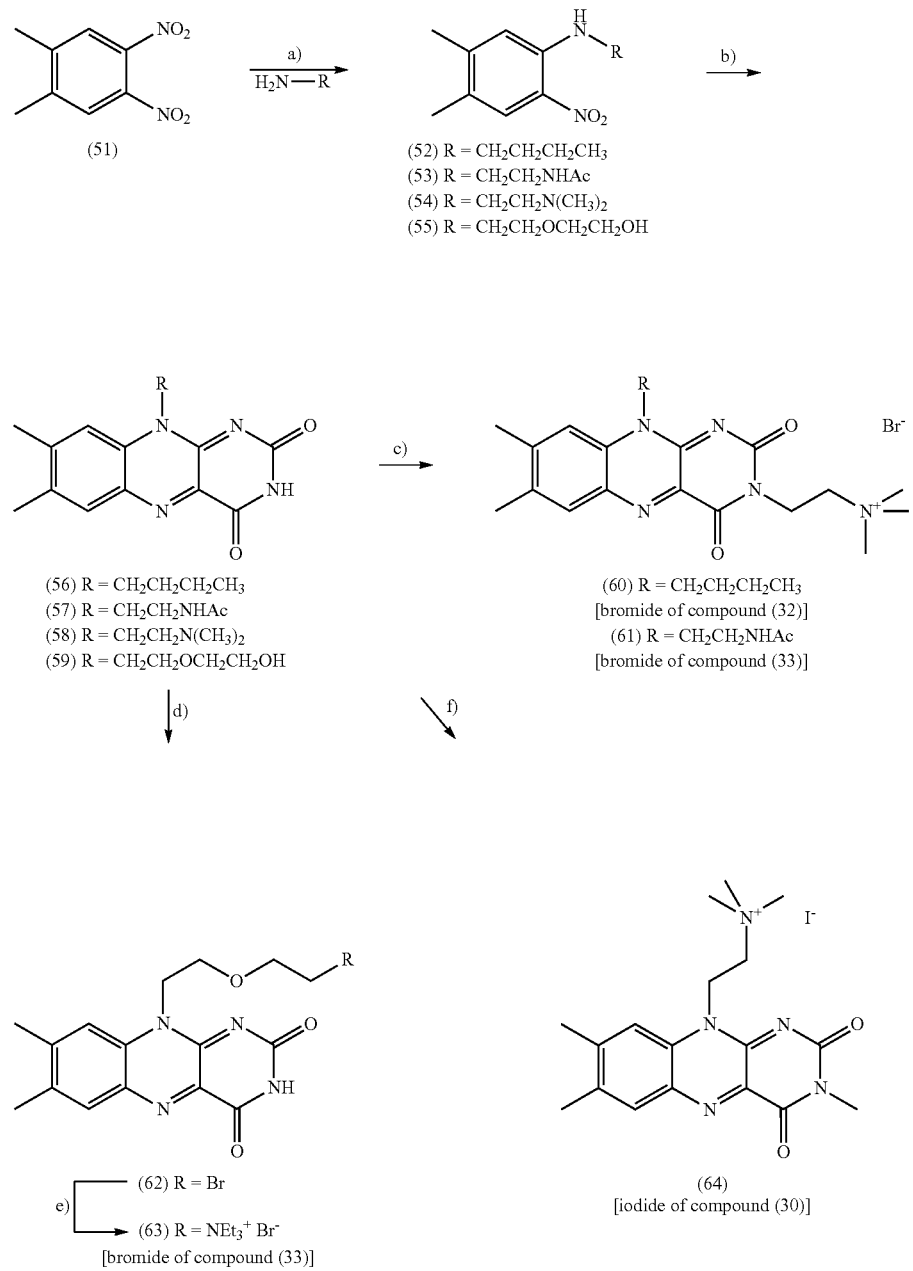

reaction conditions: a) EtOH, NEt₃, reflux, 2d; b) Pd/C, H₂, HOAc, 14 h, then alloxane monohydrate, H₃BO₃, HOAc, RT, 2d; c) bromocholine hydrobromide, Cs₂CO₃, DMF, RT, 2d; d) CBr₄, PPh₃, DMF, 10 h; e) NEt₃, DMF, 50° C., overnight; f) MeI, K₂CO₃, DMF, RT, 20 h;

Scheme 2: Synthesis of compounds (68), (69), (71) and (72);
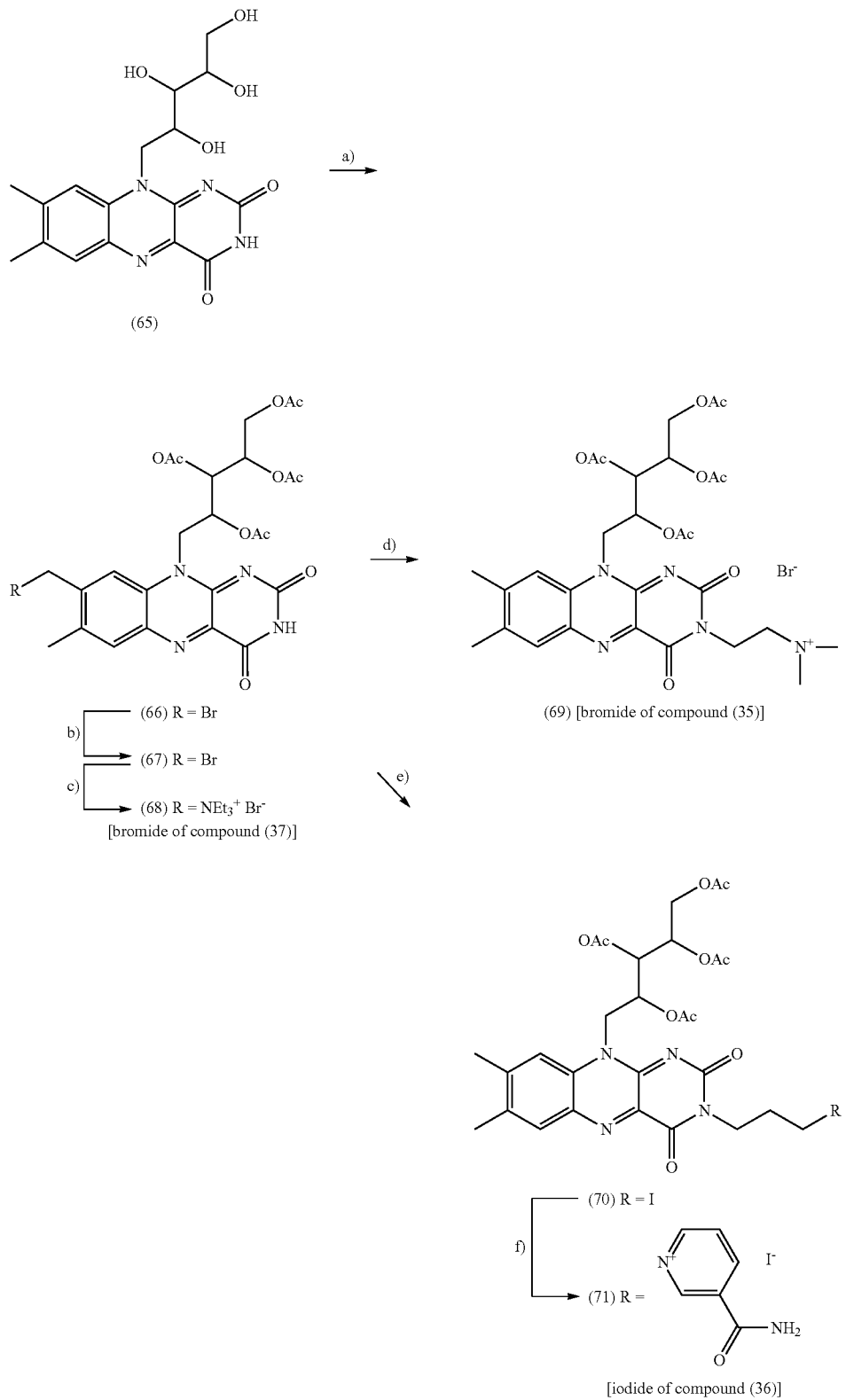
reaction conditions: a) HOAc, Ac$_2$O, HClO$_4$, 50° C., 2 h; b) Br$_2$, dioxane, benzoyl peroxide, 90° C., 1 h; c) NEt$_3$, DMF, 50° C., overnight; d) bromocholine hydrobromide, Cs$_2$CO$_3$, DMF, RT, 2d; e) 1,3-diiodopropane, K$_2$CO$_3$, DMF, RT, 2 h; f) nicotinamide, DMF, RT, 20h;

Scheme 3: Synthesis of compounds (73), (74), (75), (77) and (78);
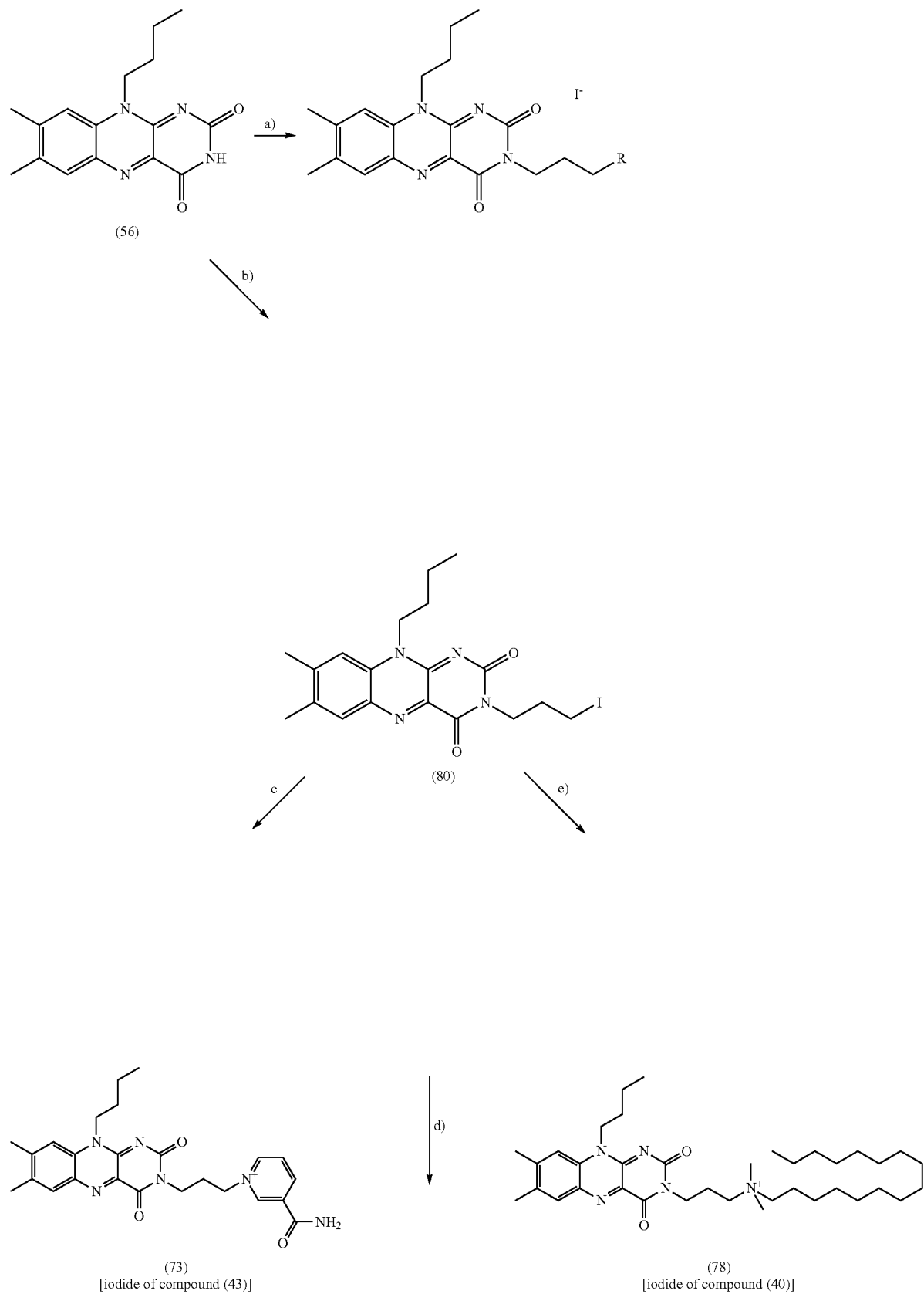

-continued

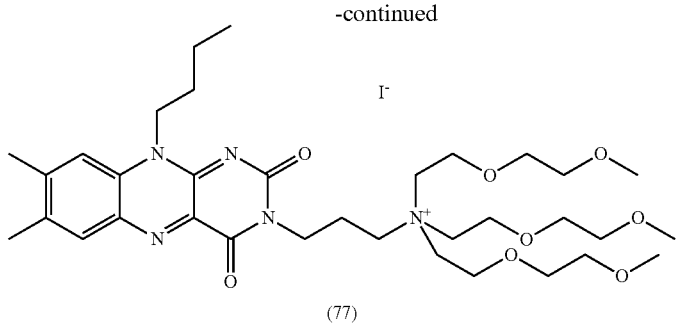

(77)
[iodide of compound (42)]

reaction conditions: a) 3-(N,N,N-triethylammonium)propyl 1-iodide iodide or 3-(pyridinium)-propyl 1-iodide iodide, K$_2$CO$_3$, DMF, RT, 2d; b) 1,3-diiodopropane, K$_2$CO$_3$, DMF, RT, 2 h; c) nicotinamide, DMF, RT, 20 h; d) tris(dioxa-3,6-heptyl)amine, DMF, RT, 20 h; e) N,N-dimethyl-N-hexadecylamine, DMF, RT 20 h;

(74) R = 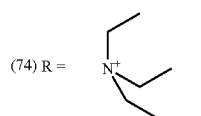

(iodide of compound of formula (39))

(75) R = 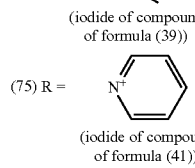

R =        (iodide of compound of formula (41))

Scheme 4: Synthesis of compounds (76);

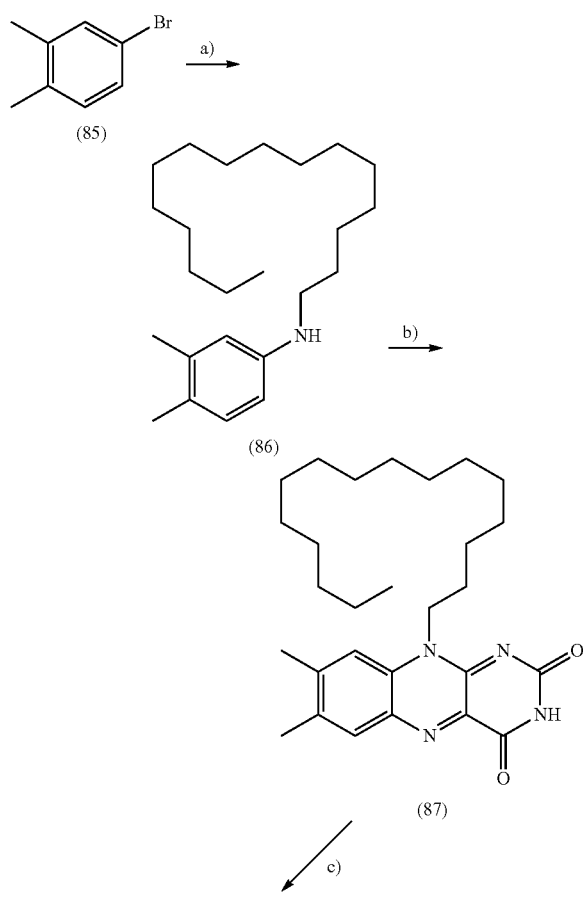

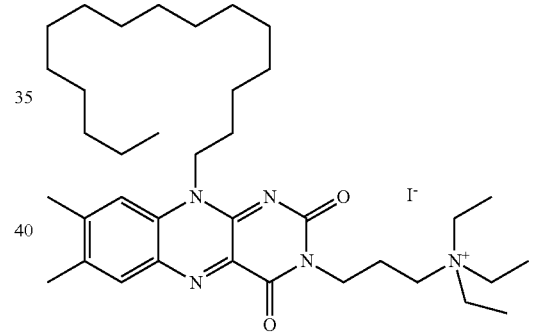

(76)
[iodide of compound (38)]

reaction conditions: a) Pd(OAc)$_2$, Na(O-tert-Bu), dioxane, n-hexadecylamine, tri(tert-Bu)phosphine in toluene, 80° C., 1d; b) violuric acid, HOAc, reflux, 2d; c) 3-(N,N,N-triethylammonium)propyl 1-iodide, K$_2$CO$_3$, DMF, RT, 2d;

All chemicals used were purchased commercially from the usual suppliers (TCI, ABCR, Acros, Merck and Fluka) and used without further purification. Solvents were distilled before use and, if required, dried in the customary manner. Dry DMF was purchased commercially from Fluka (Taufkirchen, Germany).

Thin-layer chromatography was conducted on thin aluminum foils coated with silica gel 60 F254, from Merck (Darmstadt, Germany). Preparative thin-layer chromatography was conducted on commercially available glass plates coated with silica gel 60 (20 cm×20 cm, Carl Roth GmbH & Co. KG, Karlsruhe, Germany). The compounds were detected by UV light ($\lambda$=254 nm, 333 nm) and some were detected with the naked eye or stained with ninhydrin. Chromatography was conducted with silica gel (0.060-0.200) from Acros (Waltham, USA).

NMR spectra were measured on a Bruker Avance 300 spectrometer (300 MHz [$^1$H NMR], 75 MHz [$^{13}$C NMR]) (Bruker Corporation, Billerica, USA).

All chemical shifts are reported in δ [ppm] relative to the external standard (tetramethylsilane, TMS). The coupling constants are each reported in Hz; characterization of the signals: s=singlet, d=doublet, t=triplet, m=multiplet, dd=doublet of doublets, br=broad. The integration determines the relative number of atoms. The signals in the carbon spectra were determined unambiguously by means of the DEPT method (pulse angle: 135°). Error limits: 0.01 ppm for $^1$H NMR, 0.1 ppm for $^{13}$C NMR and 0.1 Hz for coupling constants. The solvent used is stated for each spectrum.

The IR spectra were recorded on a Biorad Excalibur FTS 3000 spectrometer (Bio-Rad Laboratories GmbH, Munich, Germany).

ES-MS were measured with a ThermoQuest Finnigan TSQ 7000 spectrometer, all HR-MS were determined on a ThermoQuest Finnigan MAT 95 (each from Thermo Fisher Scientific Inc, Waltham, USA) spectrometer, and argon served as the ionizing gas for FAB.

Melting points were determined with the aid of the Bichi SMP-20 melting point measuring instrument (Büchi Labortechnik GmbH, Essen, Germany) using a glass capillary.

All UV/Vis spectra were recorded with a Varian Cary 50 Bio UV/VIS spectrometer, and fluorescence spectra with a Varian Cary Eclipse spectrometer.

The solvents for absorption and emission measurements were purchased in specific spectroscopic purity from Acros or Baker, and Uvasol from Merck. Millipore water (18 MΩ, Milli $Q_{Plus}$) was used for all measurements.

1-N-Acetylaminoethylamine[i], 1,2-dinitro-4,5-dimethyl-benzene (51)[ii], butyl(4,5-dimethyl-2-nitrophenyl)amine (52) and 10-butyl-7,8-dimethyl-10H-benzo[g]pteridine-2,4-dione (56)[iii], N-[2-({[(tert-butyl)oxy]carbonyl}amino) ethyl]-4,5-dimethyl-2-nitro-aniline[iv], N-(3'-oxabut-1'-yl)-4,5-dimethyl-2-nitroaniline and 10-(2'-methoxyethyl)-7,8-dimethyl-10H-benzo[g]pteridine-2,4-dione (65)[v], 2,3,4-triacetoxy-1-[3-(3-iodopropyl)-7,8-dimethyl-2,4-dioxo-3,4-dihydro-2H-benzo[g]pteridin-10-ylmethyl]butyl acetate (70)[vi], riboflavin tetraacetate (66)[vii] and 8α-bromotetraacetylriboflavin (17)[viii] were prepared by literature methods:

[i] M. Jasinski, G. Mloston, P. Mucha, A. Linden, H. Heimgartner, Helv. Chim. Acta 2007, 90, 1765-1779

[ii] a) A. Monge, J. A. Palop, A. López de Cerá in, V. Senador, F. J. Martinez-Crespo, Y. Sainz, S. Narro, E. Garcia, C. de Miguel, M. González, E. Hamilton, A. J. Barker, E. D. Clarke, D. T. Greenhow, J. Med. Chem. 1995, 38, 1786-1792; b) T. Sugaya, K. Nobuyuki, A. Sakaguchi, S. Tomioka, Synthesis 1995, 1257-1262; c) R. R. Holmes, R. P. Bayer, J. Am. Chem. Soc. 1960, 82, 3454-3456.

[iii] O. Wiest, Ch. B. Harrison, N. J. Saettel, R. Cibulka, M. Sax, B. König, J. Org. Chem. 2004, 69, 8183-8185

[iv] J. Butenandt, R. Epple, E.- U. Wallenborn, A. P. M. Eker, V. Gramlich, T. Carell, Chem. Eur. J. 2000, 6, No. 1, 62-72

[v] R. Epple, E.- U. Wallenborn, T. Carell, J. Am. Chem. Soc. 1997, 119, 7440-7451.

[vi] A. Barthel, L. Trieschmann, D. Ströhl, R. Kluge, G. Böhm, Rene Csuk, Arch. Pharm. Chem. Life Sci. 2009, 342, 445-452.

[vii] McCormick, D. B. J. Heterocycl. Chem. 1970, 7, 447-450.

[viii] M. C. Falk, P. G. Johnson, D. B. McCormick, Biochemistry, 1976, 15(3), 639-645

Bromocholine hydrobromide is commercially available with a purity of >98% (TCI Deutschland GmbH, Eschborn, Germany) and was used without further purification.

General Method I): Conversion of 1,2-dinitro-4,5-dimethylbenzene to Substituted 4,5-dimethyl-2-nitroanilines 1,2-Dinitro-4,5-dimethylbenzene (51) (3.92 g, 20 mmol) and the appropriate primary amine (100 mmol) were refluxed in dry ethanol (100 mL) and freshly distilled triethylamine (50 mL) at oil bath temperature 90° C. under nitrogen for 2 days. After cooling to room temperature, the solvent mixture was drawn off under reduced pressure and the residue was dried

TABLE 1

| | Amines used | |
|---|---|---|
| Example | Target compound | Primary amine |
| | (52) | $H_2NCH_2CH_2CH_2CH_3$ |
| Ia) | (53) | $H_2NCH_2CH_2NHAc$ |
| Ib) | (54) | $H_2NCH_2CH_2N(CH_3)_2$ |
| Ic) | (55) | $H_2NCH_2CH_2OCH_2CH_2OH$ |

Ia) N'-(4,5-dimethyl-2-nitrophenyl)-N,N-acetyle-thane-1,2-diamine (53)

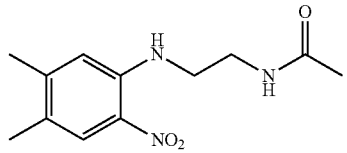 [SMILES: CC(=O)NCCNc1cc(C)c(C)cc1[N+](=O)[O-]]

The crude product was recrystallized from ethanol and 3.54 g of red/orange crystal needles were obtained (71% of theory, 141 mmol).

$^1$H NMR (300 MHz, CDCl$_3$): δ [ppm]=2.03 (s, 3H), 2.15 (s, 3H), 2.25 (s, 3H), 3.18 (t, 2H, J=6.0 Hz), 3.39 (t, 2H, J=5.8 Hz), 6.94 (s, 1H), 7.02 (m, 1H), 7.84 (s, 1H), 8.08 (bs, 1H); -MS (ESI-MS, H$_2$O/MeOH+0.1% TFA): m/z (%)=252.1 (100, (MH$^+$)); -MW=251.29 g/mol -MF=C$_{12}$H$_{17}$N$_3$O$_3$ Ib) N'-(4,5-dimethyl-2-nitrophenyl)-N,N-dimethyl-ethane-1,2-diamine (54)

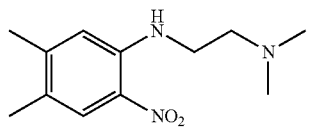

The crude product was recrystallized from ethanol. This gives 2.99 g of orange crystal needles (63% of theory, 126 mmol).

$^1$H NMR (300 MHz, CDCl$_3$): δ [ppm]=2.17 (s, 3H), 2.26 (s, 3H), 2.32 (s, 6H), 2.71 (t, 2H, J=544 Hz), 3.32 (m, 2H), 6.61 (s, 1H), 7.91 (s, 1H), 8.19 (bs, 1H); -MS (CI-MS, NH$_3$): m/z (%)=238.1 (100, (MH$^+$)); -MW=237.30 g/mol -MF=C$_{12}$H$_{19}$N$_3$O$_2$ Ic) 2-[2-(4,5-dimethyl-2-nitrophenylamino)ethoxy]ethanol (55)

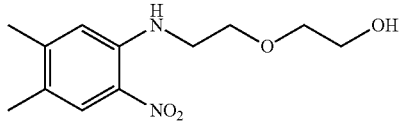 [SMILES: Cc1cc(NCCOCCO)c([N+](=O)[O-])cc1C]

The crude product was purified by column chromatography on silica gel with ethyl acetate/petroleum ether 1:1 to obtain a red oil which, after being left to stand for a prolonged period, solidified to give an orange solid (4.31 g, 86% of theory, 16.9 mmol).

$^1$H NMR (300 MHz, CDCl$_3$): δ [ppm]=2.02 (s, 3H), 2.11 (s, 3H), 2.98 (bs, 1H), 3.37 (t, 2H, J=5.4 Hz), 3.54 (t, 2H, J=5.4 Hz), 3.69 (m, 4H), 6.49 (s, 1H), 7.70 (s, 1H), 8.01 (m, 1H); -MS (ESI-MS, H$_2$O/MeOH+0.1% TFA): m/z (%)=255.1 (58, (MH$^+$)), 509.3 (100, (2 MH$^+$)); -MW=254.29 g/mol -MF=C$_{12}$H$_{18}$N$_2$O$_4$ General Method II): Conversion of Substituted 2-nitroanilines to the Corresponding Monosubstituted 10H-benzo[g]pteridine-2,4-dione Derivatives The respective 2-nitroaniline (53) to (55) obtained above in Ia) to Ic) (10 mmol) was dissolved in acetic acid (100 mL). Palladium on activated carbon (100 mg, 10% Pd) was added and the mixture was stirred in a hydrogen atmosphere at 20 bar in an autoclave at room temperature for 14 h. The colorless solution was filtered into a Schlenk flask with a nitrogen atmosphere, and alloxane monohydrate (4.00 g, 25 mmol) and boric acid (15.50 g, 250 mmol) were added. The flask was wrapped in aluminum foil and the mixture was stirred in the dark under nitrogen at room temperature for 2 days. The orange/yellow suspension was diluted with water (200 mL) and extracted four times with dichloromethane (150 mL each time). The combined organic phases were washed with water (100 mL), dried over magnesium sulfate and concentrated by rotary evaporation.

IIa) 10-(2-N-acetylaminoethyl)-7,8-dimethyl-10H-benzo[g]pteridine-2,4-dione (57)

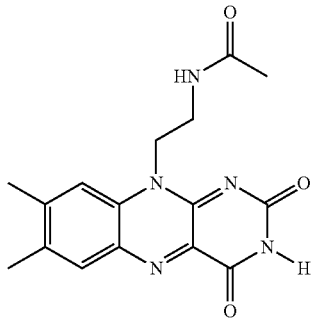 [SMILES: CC(=O)NCCn1c2nc(=O)[nH]c(=O)c-2nc2cc(C)c(C)cc21]

The residue was recrystallized from acetic acid and water (1:1). The product is obtained as an orange solid (2.56 g, 7.82 mmol, 78% of theory).

$^1$H NMR (300 MHz, DMSO-d6): δ [ppm]=2.03 (s, 3H), 2.41 (s, 3H), 2.54 (s, 3H), 3.32 (t, 2H, J=5.4 Hz), 3.46 (t, 2H, J=5.4 Hz), 7.79-7.83 (s, 1H), 11.32 (s, 1H); -MS (ESI-MS, H$_2$O/MeOH+0.1% TFA): m/z (%)=328.0 (100, (MH$^+$)); -MW=327.35 g/mol -MF=C$_{16}$H$_{17}$N$_5$O$_3$ IIb) 10-(2-dimethylaminoethyl)-7,8-dimethyl-10H-benzo[q]pteridine-2,4-dione (58)

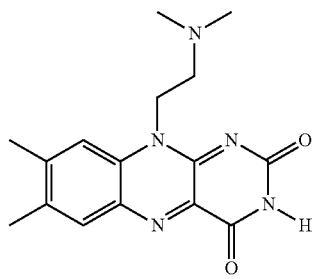 [SMILES: Cc1cc2nc3c(=O)[nH]c(=O)nc-3n(CCN(C)C)c2cc1C]

The residue was purified by column chromatography on silica gel with ethyl acetate/methanol 20:1→5:2 to obtain an orange solid (2.22 g, 7.07 mmol, 71% of theory).

$^1$H NMR (300 MHz, DMSO-d6): δ [ppm]=2.34 (s, 3H), 2.43 (s, 3H), 2.91 (s, 6H), 3.39 (m, 2H), 4.61 (m, 2H), 7.52 (s, 1H), 7.78 (s, 1H), 11.38 (s, 1H); -MS (ESI-MS, H$_2$O/MeOH+0.1% TFA): m/z (%)=314.0 (100, (MH$^+$)); -MW=313.36 g/mol -MF=C$_{16}$H$_{19}$N$_5$O$_2$ IIc) 10-[2-(2-hydroxyethoxy)ethyl]-7,8-dimethyl-10H-benzo[q]pteridine-2,4-dione (59)

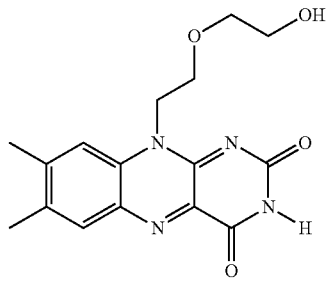 [SMILES: Cc1cc2nc3c(=O)[nH]c(=O)nc-3n(CCOCCO)c2cc1C]

The residue was purified by column chromatography on silica gel with ethyl acetate/methanol 20:1→5:2. This gives 1.98 g of orange solid (6.0 mmol, 60% of theory).

$^1$H NMR (300 MHz, DMSO-d6): δ [ppm]=2.42 (s, 3H), 2.53 (s, 3H), 3.28 (t, 2H, J=5.4 Hz), 3.49 (t, 2H, J=5.4 Hz), 3.66 (m, 4H), 7.76 (s, 1H), 7.88 (s, 1H), 11.33 (s, 1H); -MS (ESI-MS, H$_2$O/MeOH+0.1% TFA): m/z (%)=331.1 (100, (MH$^+$)); 661.4 (61, (2MH$^+$)); -MW=330.35 g/mol -MF=C$_{16}$H$_{18}$N$_4$O$_4$ III) 10-[2-(2-bromoethoxy)ethyl]-7,8-dimethyl-10H-benzo[q]pteridine-2,4-dione (62)

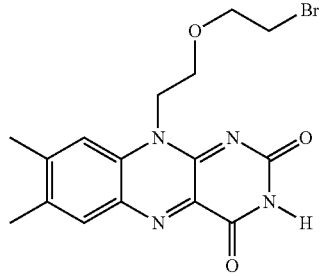 [SMILES: Cc1cc2nc3c(=O)[nH]c(=O)nc-3n(CCOCCBr)c2cc1C]

The 10-[2-(2-hydroxyethoxy)ethyl]-7,8-dimethyl-10H-benzo[g]pteridine-2,4-dione (59) obtained in IIc) (80 mg, 0.25 mmol) together with tetrabromomethane (100 mg, 0.3 mmol) was dissolved in dry DMF (5 mL). Triphenylphosphine (168 mg, 0.5 mmol) was added at 0° C. in several small portions. The mixture was stirred at room temperature overnight and then the solvent was drawn off under reduced pressure. The residue was purified by preparative thin-layer chromatography with ethyl acetate/methanol 25:1. This gave 72 mg of a yellow solid (0.186 mmol, 73% of theory).

$^1$H NMR (300 MHz, DMSO-d6): δ [ppm]=2.40 (s, 3H), 2.51 (s, 3H), 3.23 (t, 2H, J=5.4 Hz), 3.56 (t, 2H, J=5.4 Hz), 3.61 (m, 2H), 3.87 (m, 2H), 7.78 (s, 1H), 7.93 (s, 1H), 11.30 (s, 1H); -MS (ESI-MS, H$_2$O/MeOH+0.1% TFA): m/z (%)=393.1 & 395.1 (100, (MH$^+$)); -MF: C$_{16}$H$_{17}$BrN$_4$O$_3$ -FW: 393.24 g/mol;

IV) trimethyl[2-(3,7,8-trimethyl-2,4-dioxo-3,4-dihydro-2H-benzo[g]pteridin-10-yl)ethyl]ammonium iodide (64)

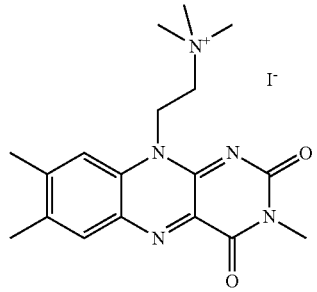

The flavin (58) obtained in IIb) (331 mg, 1.0 mmol) was dissolved in dry DMF (20 mL), cesium carbonate (488 mg, 1.5 mmol) and methyl iodide (1.42 g, 10.0 mmol) were added, and the mixture was stirred at room temperature in the dark for 20 h. The suspension was diluted with chloroform (100 mL) and washed with water (30 mL). The organic phase was dried over magnesium sulfate and the solvents were drawn off under reduced pressure. The crude product was purified by preparative thin-layer chromatography on silica gel (CHCl$_3$/MeOH—4:1).

Yield: 263 mg of an orange solid (0.56 mmol, 56% of theory)

R$_f$=0.1 (CHCl$_3$:MeOH—4:1)

$^1$H NMR (300 MHz, DMSO-d6): δ [ppm]=2.36 (s, 3H), 2.42 (s, 3H), 3.17 (bs, 9H), 3.41 (m, 2H), 3.48 (s, 3H), 4.36 (m, 2H), 7.56 (s, 1H), 7.79 (s, 1H); -MS (ESI-MS, H$_2$O/MeOH+0.1% TFA): m/z (%)=342.1 (100, (M$^+$)); -MW=342.42+126.90 g/mol -MF=C$_{18}$H$_{24}$N$_5$O$_2$I V) {2-[2-(7,8-dimethyl-2,4-dioxo-3,4-dihydro-2H-benzo[g]pteridin-10-yl)-ethoxy]ethyl}triethylammonium bromide (63)

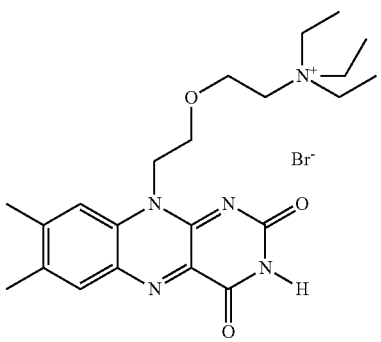 [SMILES: CC[N+](CC)(CC)CCOCCn1c2nc(=O)[nH]c(=O)c-2nc2cc(C)c(C)cc21 ; [Br-]]

The flavin (62) obtained in III) (393 mg, 1.0 mmol) was dissolved in dry DMF (20 mL), triethylamine (1.01 g, 10.0 mmol) was added and the mixture was stirred at 50° C. in the dark overnight. The suspension was diluted with chloroform (100 mL) and washed with water (30 mL). The organic phase was dried over magnesium sulfate and the solvents were drawn off under reduced pressure. The crude product was purified by preparative thin-layer chromatography on silica gel (CHCl$_3$/MeOH—4:1).

Yield: 141 mg of microcrystalline orange solid (0.284 mmol, 28% of theory)

R$_f$=0.1 (CHCl$_3$:MeOH—4:1)

$^1$H NMR (300 MHz, DMSO-d6): δ [ppm]=1.26 (t, 9H, J=7.4 Hz), 2.42 (s, 3H), 2.53 (s, 3H), 3.22-3.37 (m, 8H), 3.46 (t, 2H, J=5.4 Hz), 3.68 (m, 4H), 7.78 (s, 1H), 7.91 (s, 1H), 11.31 (s, 1H); -MS (ESI-MS, H$_2$O/MeOH+0.1% TFA): m/z (%)=414.1 (100, (M$^+$)); -MW=414.53+79.90 g/mol -MF=C$_{22}$H$_{32}$N$_5$O$_3$Br General Method VI): Functionalization of Flavins in Position 3 by Means of Bromocholine Hydrobromide The respective flavin specified (1.0 mmol) was dissolved in dry DMF (20 mL), cesium carbonate (1.63 g, 5 mmol) and bromocholine hydrobromide (0.5 g, 2.0 mmol) were added, and the mixture was stirred at room temperature in the dark for 1 d. Bromocholine hydrobromide (0.5 g, 2.0 mmol) was again added and the mixture was stirred at room temperature in the dark for a further day. The DMF was drawn off and the residue was suspended in chloroform/methanol 6:1 (50 mL). The suspension was filtered and the filtrate was concentrated to dryness. The crude product was purified by preparative thin-layer chromatography on silica gel (CHCl₃/MeOH—4:1) and by recrystallization from water.

VIa) [2-(10-butyl-7,8-dimethyl-2,4-dioxo-4,10-dihydro-2H-benzo[g]pteridin-3-yl)-ethyl]trimethylammonium bromide (60)

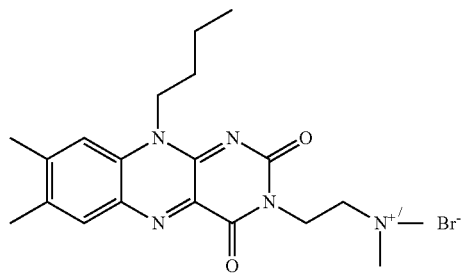

Obtained from 10-butyl-7,8-dimethyl-10H-benzo[g]pteridine-2,4-dione (56) (310 mg, 1.0 mmol) by conversion according to general method VI), as an orange solid in a yield of 161 mg (0.347 mmol, 35% of theory).

$R_f$=0.1 (CHCl₃:MeOH—4:1)

¹H NMR (300 MHz, DMSO-d6): δ [ppm]=0.97 (t, 3H, J=7.3 Hz), 1.48 (m, 2H), 1.70 (m, 2H), 2.41 (s, 3H), 2.51 (s, 3H), 3.14-3.35 (m, 8H), 3.95 (t, 2H, J=6 Hz), 4.56 (t, 2H, J=7.8 Hz), 7.77 (s, 1H), 7.89 (s, 1H); -MS (ESI-MS, H₂O/MeOH+0.1% TFA): m/z (%)=384.1 (100, (M⁺)); -MW=384.51+79.90 g/mol -MF=C₂₁H₃₀N₅O₂Br VIb) {2-[10-(2-acetylaminoethyl)-7,8-dimethyl-2,4-dioxo-4,10-dihydro-2H-benzo[g]pteridin-3-yl]ethyl}thrimethylammonium bromide (61)

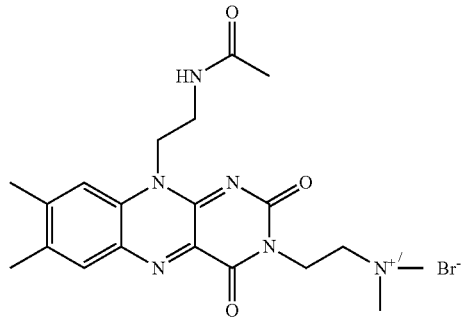

The flavin (57) obtained in IIa) (330 mg, 1.0 mmol), when converted by general method IV), gave 178 mg of an orange solid (0.361 mmol, 36% of theory)

$R_f$=0.1 (CHCl₃:MeOH—4:1)

¹H NMR (300 MHz, DMSO-d6): δ [ppm]=2.03 (s, 3H), 2.41 (s, 3H), 2.51 (s, 3H), 3.16-3.32 (m, 8H), 3.46 (t, 2H, J=5.6 Hz), 4.66 (t, 2H, J=5.6 Hz), 3.96 (t, 2H, J=6 Hz), 6.81 (m, 1H), 7.75 (s, 1H), 7.88 (s, 1H); -MS (ESI-MS, H₂O/MeOH+0.1% TFA): m/z (%)=413.1 (100, (M⁺)); -MW=413.50+79.90 g/mol -MF=C₂₁H₂₉N₆O₃Br VII) {2-[7,8-dimethyl-2,4-dioxo-10-(2,3,4,5-tetraacetoxypentyl)-4,10-dihydro-2H-benzo[g]pteridin-3-yl]ethyl}trimethylammonium bromide (69)

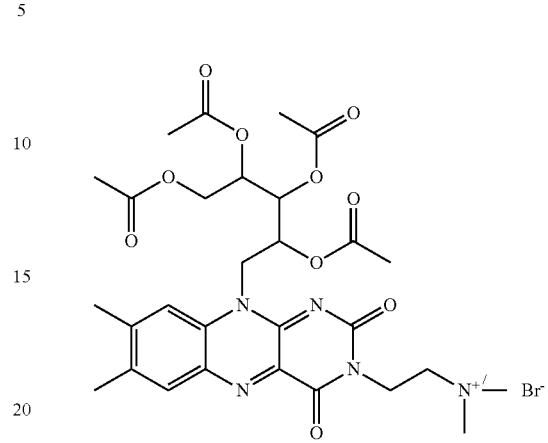

Riboflavin tetraacetate (66) (540 mg, 1.0 mmol), when converted by general method IV), gave 191 mg of a light brown solid (0.268 mmol, 27% of theory).

$R_f$=0.1 (CHCl₃:MeOH—4:1)

¹H NMR (300 MHz, MeOD): δ [ppm]=1.71 (s, 3H), 2.02 (s, 3H), 2.21 (s, 3H), 2.29 (s, 3H), 2.42 (s, 3H), 2.52 (s, 3H), 3.12-3.27 (m, 8H), 3.94 (t, 2H, J=5.8 Hz), 4.20-4.28 (m, 1H), 4.52 (m, 1H), 5.18 (m, 2H), 5.44 (m, 1H), 5.54 (m, 1H), 5.68 (m, 1H), 7.89 (s, 1H), 7.93 (s, 1H); -MS (ESI-MS, H₂O/MeOH+0.1% TFA): m/z (%)=630.1 (100, (M⁺)); -MW=630.68+79.90 g/mol -MF=C₃₀H₄₀N₅O₁₀Br VIII) triethyl-[7-methyl-2,4-dioxo-10-(2,3,4,5-tetraacetoxypentyl)-2,3,4,10-tetrahydrobenzo[g]pteridin-8-ylmethyl]ammonium bromide (68)

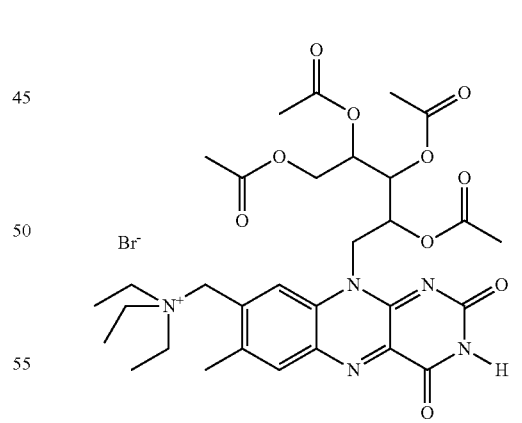

8α-Bromotetraacetyriboflavin (67) (0.78 g, 1.25 mmol) was dissolved in DMF (10 mL), the solution was degassed and triethylamine (0.60 g, 0.76 mL, 6.0 mmol) was added dropwise over the course of 5 min. The mixture was stirred in the dark at 50° C. under N₂ overnight. After cooling to room temperature, the reaction mixture was added dropwise to 200 mL of ice-cold diethyl ether, and the product was filtered off, washed with diethyl ether and dried under reduced pressure.

The residue was dissolved in chloroform, precipitated with diethyl ether, centrifuged off and dried. For further purification, the product was recrystallized from water. Light brown solid (0.31 g, 0.43 mmol, 34% of theory).

$^1$H NMR (300 MHz, MeOD): δ [ppm]=1.25 (t, 9H, J=7.3 Hz), 1.71 (s, 3H), 2.02 (s, 3H), 2.21 (s, 3H), 2.29 (s, 3H), 2.42 (s, 3H), 2.59 (m, 2H), 3.15-3.30 (m, 6H), 4.20-4.28 (m, 1H), 4.52 (m, 1H), 5.18 (m, 2H), 5.44 (m, 1H), 5.54 (min, 1H), 5.68 (m, 1H), 7.89 (s, 1H), 7.93 (s, 1H), 11.32 (s, 1H); -MS (ESI-MS, H$_2$O/MeOH+0.1% TFA): m/z (%)=644.1 (100, (M$^+$)); -MW=644.71+79.90 -MF=C$_{31}$H$_{42}$N$_5$O$_{10}$Br

IX) 2-carbamoyl-1-{3-[7,8-dimethyl-2,4-dioxo-10-(2,3,4,5-tetraacetoxypentyl)-4,10-dihydro-2H-benzo[g]pteridin-3-yl]propyl}pyridinium iodide (72)

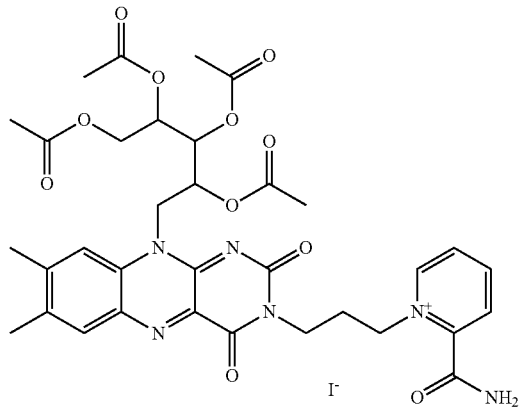 [SMILES: CC(=O)OCC(OC(C)=O)C(OC(C)=O)C(Cn1c2nc(=O)n(CCC[n+]3ccccc3C(N)=O)c(=O)c-2nc2cc(C)c(C)cc21)OC(C)=O ; [I-]]

2,3,4-Triacetoxy-1-[3-(3-iodopropyl)-7,8-dimethyl-2,4-dioxo-3,4-dihydro-2H-benzo[g]pteridin-10-ylmethyl]butyl acetate (70) (0.75 g, 1.05 mmol) was stirred with nicotinamide (146 mg, 1.2 mmol) and NaHCO$_3$ (0.1 g, 1.2 mmol) in DMF (10 mL) in a nitrogen atmosphere in the dark at 50° C. for 24 h. The solvent was drawn off under reduced pressure and the residue was purified by preparative thin-layer chromatography (CHCl$_3$/MeOH 6:1).

277 mg of light brown solid (0.33 mmol, 32% of theory) were obtained.

$^1$H NMR (300 MHz, MeOD): δ [ppm]=1.70 (s, 3H), 2.03 (s, 3H), 2.20 (s, 3H), 2.28 (s, 3H), 2.42 (s, 3H), 2.48 (m, 2H), 2.52 (s, 3H), 4.18-4.31 (m, 3H), 4.51 (m, 1H), 4.88 (m, 2H), 5.17 (m, 2H), 5.45 (m, 1H), 5.52 (m, 1H), 5.67 (m, 1H), 7.86 (s, 1H), 7.92 (s, 1H), 8.70-8.78 (m, 2H), 9.23 (d, J=5.6 Hz, 1H), 9.38 (d, J=5.6 Hz, 1H); -MS (ESI-MS, H$_2$O/MeOH+ 0.1% TFA): m/z (%)=707.1 (100, (M$^+$)); -MW=707.72+ 126.90 -MF=C$_{34}$H$_{39}$N$_6$O$_{11}$I

X) 3-(10-butyl-7,8-dimethyl-2,4-dioxo-4,10-dihydro-2H-benzo[g]pteridin-3-yl)propyl iodide (80)

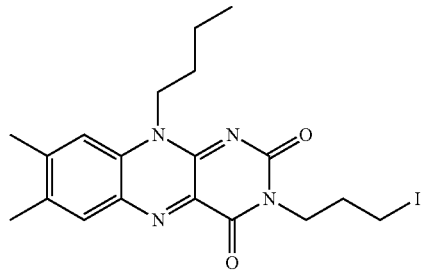 [SMILES: CCCCn1c2nc(=O)n(CCCI)c(=O)c-2nc2cc(C)c(C)cc21]

Compound (56) (0.6 g, 2.0 mmol) and Cs$_2$CO$_3$ (1.8 g, 6 mmol) were initially charged in dry DMF (40 mL). 1,3-Diiodopropane (1.5 g, 5.0 mmol) was added and the mixture was stirred in the dark under N$_2$ at room temperature for 2 h. The solvent was drawn off under reduced pressure, and the residue was dissolved in ethyl acetate (200 mL) and washed with H$_2$O (2×100 mL). After drying the organic phase over MgSO$_4$, the solvent was drawn off under reduced pressure. After purification by column chromatography (silica gel, CHCl$_3$/MeOH, 98:2), the target compound (0.82 g, 1.76 mmol, 88%) was obtained as a yellow solid.

$^1$H NMR (300 MHz, CDCl$_3$): δ [ppm]=0.97 (t, J=7.4 Hz, 3H), 1.48 (m, 2H), 1.72 (m, 2H), 2.23-2.36 (m, 2H), 2.41 (s, 3H), 2.50 (s, 3H), 3.24 (t, J=7.4 Hz, 2H), 4.15-4.26 (m, 2H), 4.56 (t, J=7.8 Hz, 2H), 7.77 (s, 1H), 7.89 (s, 1H); -MS (ESI-MS, H$_2$O/MeOH+0.1% TFA): m/z (%)=467.1 (100, (MH$^+$)); -MW=466.33 g/mol -MF=C$_{19}$H$_{23}$N$_4$O$_2$I

XI) 2-carbamoyl-1-{3-[7,8-dimethyl-2,4-dioxo-10-butyl-4,10-dihydro-2H-benzo[g]pteridin-3-yl]propyl}pyridinium iodide (73)

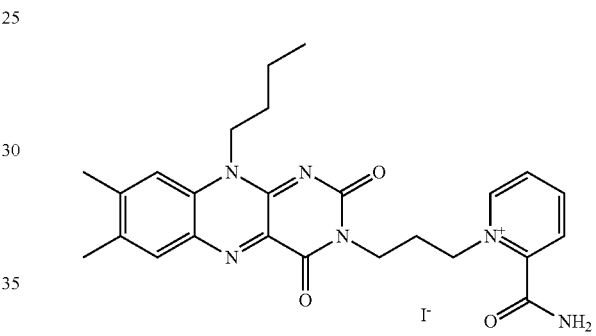

3-(10-Butyl-7,8-dimethyl-2,4-dioxo-4,10-dihydro-2H-benzo[g]pteridin-3-yl)propyl iodide (80) (0.51 g, 1.05 mmol) was stirred with nicotinamide (146 mg, 1.2 mmol) and NaHCO$_3$ (0.1 g, 1.2 mmol) in DMF (10 mL) in a nitrogen atmosphere in the dark at 50° C. for 24 h. The solvent was drawn off under reduced pressure and the residue was purified by preparative thin-layer chromatography (CHCl$_3$/MeOH 6:1). 276 mg of orange solid (0.47 mmol, 46% of theory) were obtained.

$^1$H NMR (300 MHz, DMSO): δ [ppm]=0.91 (t, 3H), 1.43 (m, 2H), 1.72 (m, 2H), 2.31 (m, 2H), 2.41 (s, 3H), 2.58 (s, 3H), 4.02 (m, 2H), 4.63 (m, 2H), 4.71 (m, 2H), 5.31 (s, 2H), 7.86 (s, 1H), 7.95 (m, 1H), 8.18 (s, 1H), 8.51 (s, 1H), 8.94 (d, J=5.6 Hz, 1H), 9.23 (d, J=5.6 Hz, 1H), 9.52 (m, 1H); -MS (ESI-MS, H$_2$O/MeOH+0.1% TFA): m/z (%)=461.1 (100, (M$^+$)); -MW=461.55+126.90 -MF=C$_{25}$H$_{29}$N$_6$O$_3$I

XII) 10-hexadecyl-7,8-dimethyl-10H-benzo[g]pteridine-2,4-dione (87)

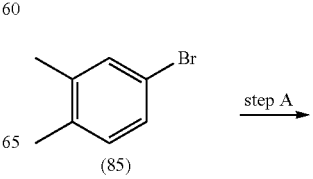

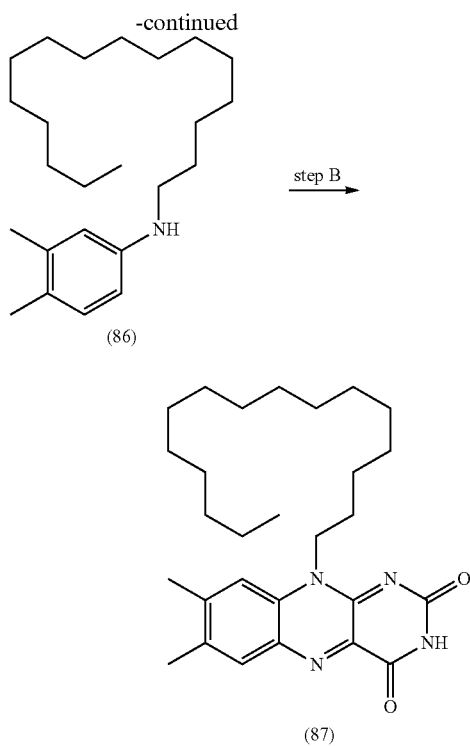

(86)

(87)

Step A, Synthesis of the Amine (86)

3,4-Dimethyl-1-bromobenzene (85) (0.37 g, 2 mmol) was added to a suspension of palladium(II) acetate (22 mg, 0.1 mmol) and sodium tert-butoxide (224 mg, 2.3 mmol) in dry dioxane (5 mL) under argon in a dry Schlenk tube. After adding hexadecylamine (0.72 g, 3 mmol) and tri(tert-butyl) phosphine in toluene (0.3 mL), the mixture was stirred at 80° C. overnight. After cooling to room temperature, the reaction mixture was diluted with dichloromethane (30 mL) and washed with $H_2O$ (2×10 mL). After drying the organic phase over $MgSO_4$, the solvent was drawn off under reduced pressure. After purification by column chromatography (silica gel, ethyl acetate/EtOH, 9:1), the target compound (86) (0.62 g, 1.79 mmol, 90%) was obtained as a colorless solid.

Step B, Synthesis of the Flavin (87)

The amine (86) from the previous step (0.62 g, 1.79 mmol) was refluxed with violuric acid (320 mg, 2 mmol) in glacial acetic acid (10 mL) in a nitrogen atmosphere in the dark for 24 h. Violuric acid (320 mg, 2 mmol) was added and the mixture was kept under the same conditions for a further 24 h. The solvent was drawn off under reduced pressure and the residue was purified by preparative thin-layer chromatography ($CH_2Cl_2$/EtOH 20:1). 254 mg of orange solid (0.54 mmol, 30% of theory) were obtained.

$^1$H NMR (300 MHz, DMSO-d6): δ [ppm]=1.02 (t, 3H), 1.20-1.37 (m, 26H), 1.73 (m, 4H), 2.43 (s, 3H), 2.56 (s, 3H), 7.48 (s, 1H), 8.04 (s, 1H), 11.30 (bs, 1H); -MS (ESI-MS, $H_2O$/MeOH+0.1% TFA): m/z (%)=467.1 (100, (M$^+$)); -MW=466.67 -MF=$C_{28}H_{42}N_4O_2$ General Method XIII): Functionalization of Flavins in Position 3 by 3-(N,N,N-triethylammonium)propyl 1-iodide iodide or 3-(pyridinium)propyl 1-iodide iodide

TABLE 2

| | Flavins and used | |
|---|---|---|
| Example | Target compound | Flavin |
| XIa) | (74) | (56) |
| XIb) | (75) | (56) |
| XIc) | (76) | (87) |

The respective flavin specified in table 2 (1.0 mmol) was dissolved in dry DMF (20 mL), potassium carbonate (0.69 g, 5 mmol) and 3-(N,N,N-triethylammonium)propyl 1-iodide iodide or 3-(pyridinium)propyl 1-iodide iodide (0.8 g or 0.76 g, 2.0 mmol) were added and the mixture was stirred at room temperature in the dark for 1 d. 3-(N,N,N-Triethylammonium)propyl 1-iodide iodide or 3-(pyridinium)propyl 1-iodide iodide (0.8 g or 0.76 g, 2.0 mmol) was again added and the mixture was stirred at room temperature in the dark for a further day. The DMF was drawn off. The crude product was purified by column chromatography on silica gel ($CHCl_3$/MeOH—20:1→6:1).

XIIIa) [3-(10-butyl-7,8-dimethyl-2,4-dioxo-4,10-dihydro-2H-benzo[g]pteridin-3-yl)-propyl]triethylammonium iodide (74)

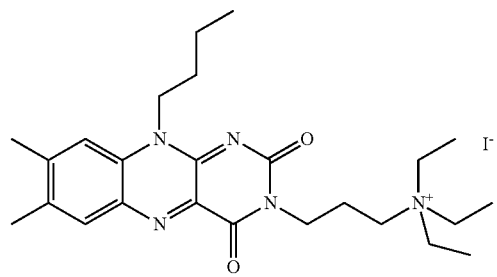 [SMILES: CCCCn1c2nc(=O)n(CCC[N+](CC)(CC)CC)c(=O)c-2nc2cc(C)c(C)cc21 ; [I-]]

Obtained from 10-butyl-7,8-dimethyl-10H-benzo[g]pteridine-2,4-dione (56) (310 mg, 1.0 mmol) and 3-(N,N,N-triethylammonium)propyl 1-iodide iodide, by conversion according to general method XII) as an orange solid in a yield of 188 mg (0.331 mmol, 33% of theory).

$R_f$=0.05 ($CHCl_3$:MeOH—6:1)

$^1$H NMR (300 MHz, DMSO): δ [ppm]=0.92 (t, 3H), 1.18 (m, 9H), 1.45 (m, 2H), 1.68 (m, 2H), 1.97 (m, 2H), 2.39 (s, 3H), 2.52 (s, 3H), 3.21 (m, 8H), 3.31 (s, 6H), 3.97 (m, 2H), 4.01 (m, 2H), 7.86 (s, 1H), 7.98 (s, 1H); -MS (ESI-MS, $H_2O$/MeOH+0.1% TFA): m/z (%)=440.2 (100, (M$^+$)); -MW=440.61+126.90 g/mol -MF=$C_{25}H_{38}N_5O_2I$

XIIIb) [3-(10-butyl-7,8-dimethyl-2,4-dioxo-4,10-dihydro-2H-benzo[g]pteridin-3-yl)-propyl]pyridinium iodide (75)

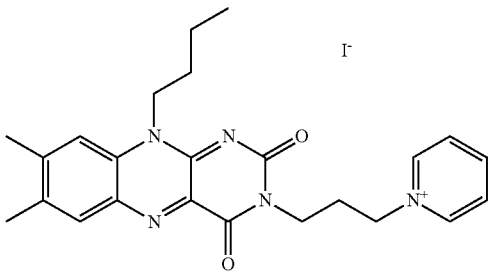 [SMILES: CCCCn1c2nc(=O)n(CCC[n+]3ccccc3)c(=O)c-2nc2cc(C)c(C)cc21 ; [I-]]

Obtained from 10-butyl-7,8-dimethyl-10H-benzo[g]pteridine-2,4-dione (56) (310 mg, 1.0 mmol) and 3-(pyridinium) propyl 1-iodide iodide, by conversion according to general method XIII) as an orange solid in a yield of 196 mg (0.36 mmol, 36% of theory).

$R_f$=0.05 (CHCl$_3$:MeOH—6:1)

$^1$H NMR (300 MHz, DMSO): δ [ppm]=0.93 (t, 3H), 1.48 (m, 2H), 1.71 (m, 2H), 2.30 (m, 2H), 2.46 (s, 3H), 2.54 (s, 3H), 3.98 (m, 2H), 4.61 (m, 2H), 4.72 (m, 2H), 5.31 (s, 2H), 7.82 (s, 1H), 7.92 (s, 1H), 8.19 (m, 2H), 8.61 (m, 1H), 9.22 (d, J=5.6 Hz, 1H); -MS (ESI-MS, H$_2$O/MeOH+0.1% TFA): m/z (%)=418.1 (100, (M$^+$)); -MS (ESI-MS, H$_2$O/MeOH+0.1% TFA): m/z (%)=418.2 (100, (M$^+$)); -MW=418.51+126.90 g/mol -MF=C$_{24}$H$_{28}$N$_5$O$_2$I

XIIIc) [3-(10-hexadecyl-7,8-dimethyl-2,4-dioxo-4,10-dihydro-2H-benzo[g]pteridin-3-yl)propyl]triethylammonium iodide (76)

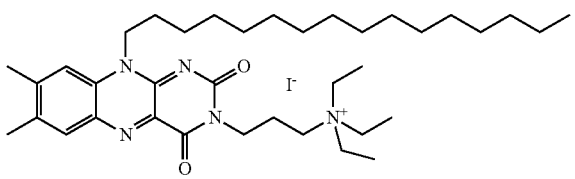 [SMILES: CCCCCCCCCCCCCCCCn1c2nc(=O)n(CCC[N+](CC)(CC)CC)c(=O)c-2nc2cc(C)c(C)cc21 ; [I-]]

The flavin (87) obtained in XII) (466 mg, 1.0 mmol), when reacted by general method XIII) with 3-(N,N,N-triethylammonium)propyl 1-iodide iodide, gave 131 mg of an orange solid (0.178 mmol, 18% of theory)

$R_f$=0.1 (CHCl$_3$:MeOH—6:1)

$^1$H NMR (300 MHz, DMSO): δ [ppm]=0.85 (t, 3H), 1.17 (m, 9H), 1.03 (t, 3H), 1.20-1.39 (m, 26H), 1.52 (m, 2H), 1.73 (m, 4H), 1.81 (m, 2H), 2.26 (m, 2H), 2.42 (s, 3H), 2.53 (s, 3H), 3.28 (s, 6H), 3.74 (m, 2H), 3.46 (m, 2H), 4.30 (m, 2H), 4.72 (m, 2H), 7.48 (s, 1H), 8.05 (s, 1H); -MS (ESI-MS, H$_2$O/MeOH+0.1% TFA): m/z (%)=608.2 (100, (M$^+$)); -MW=608.90+126.90 g/mol -MF=C$_{37}$H$_{62}$N$_5$O$_2$I

XIV) [3-(10-butyl-7,8-dimethyl-2,4-dioxo-4,10-dihydro-2H-benzo[g]pteridin-3-yl)-propyl]tri(dioxa-3,6-heptyl)ammonium iodide (77)

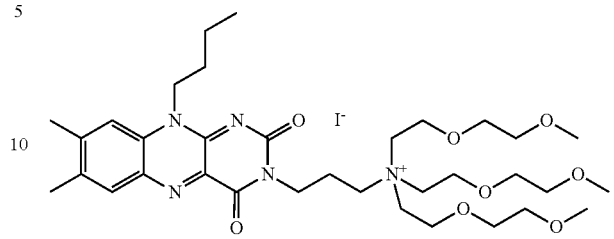

3-(10-Butyl-7,8-dimethyl-2,4-dioxo-4,10-dihydro-2H-benzo[g]pteridin-3-yl)propyl iodide (80) (0.51 g, 1.05 mmol) was stirred with tris(dioxa-3,6-heptyl)amine (646 mg, 2 mmol) and NaHCO$_3$ (0.1 g, 1.2 mmol) in DMF (4 mL) in a nitrogen atmosphere in the dark at 50° C. for 24 h. The solvent was drawn off under reduced pressure and the residue was purified by preparative thin-layer chromatography (CHCl$_3$/MeOH 6:1). 103 mg of brown/red viscous oil (0.13 mmol, 12% of theory) were obtained.

MS (ESI-MS, H$_2$O/MeOH+0.1% TFA): m/z (%)=662.1 (100, (M$^+$)); -MW=662.55+126.90 -MF=C$_{34}$H$_{56}$N$_5$O$_8$I

XV) [3-(10-butyl-7,8-dimethyl-2,4-dioxo-4,10-dihydro-2H-benzo[g]pteridin-3-yl)-propyl]dimethylhexadecylammonium iodide (78)

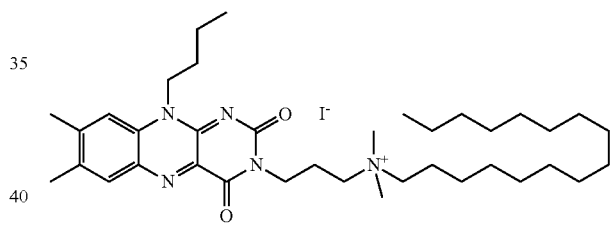

3-(10-Butyl-7,8-dimethyl-2,4-dioxo-4,10-dihydro-2H-benzo[g]pteridin-3-yl)propyl iodide (80) (0.51 g, 1.05 mmol) was stirred with N,N-dimethylhexadecylamine (540 mg, 2 mmol) and NaHCO$_3$ (0.1 g, 1.2 mmol) in DMF (4 mL) in a nitrogen atmosphere in the dark at 50° C. for 24 h. The solvent was drawn off under reduced pressure and the residue was purified by preparative thin-layer chromatography (CHCl$_3$/MeOH 6:1).

147 mg of light brown solid (0.20 mmol, 19% of theory) were obtained.

$^1$H NMR (300 MHz, CDCl$_3$): δ [ppm]=0.83 (t, 3H), 1.04 (t, 3H), 1.21-1.38 (m, 26H), 1.52 (m, 2H), 1.71 (m, 4H), 1.82 (m, 2H), 2.28 (m, 2H), 2.41 (s, 3H), 2.54 (s, 3H), 3.29 (s, 6H), 3.75 (m, 2H), 3.43 (m, 2H), 4.29 (m, 2H), 4.70 (m, 2H), 7.41 (s, 1H), 8.06 (s, 1H); -MS (ESI-MS, H$_2$O/MeOH+0.1% TFA): m/z (%)=608.1 (100, (M$^+$)); -MW=608.90+35.45 -MF=C$_{37}$H$_{62}$N$_5$O$_2$Cl

Example 2

Phototoxicity Experiments a) Production of the Test Plates and Bacterial Strains A sample of the bacterial strain *Staphylococcus aureus* (ATCC number: 25923) or *Escherichia coli* (ATCC number:

25922) was taken from a cryogenically frozen culture, isolated on Miller-Hinton agar plates and cultivated under aerobic conditions at 37° C. in an overnight culture. Thereafter, 5 ml of Müller-Hinton liquid medium were inoculated with a smear of the bacterial culture (single colony) and incubated at 37° C. overnight. The bacterial suspension thus obtained was centrifuged at 2500 rpm for 10 min and the bacterial pellet obtained was resuspended in 5 ml of sterile PBS. The optical density of the bacterial suspensions for the phototoxicity tests was $OD_{600nm}$=0.6, which corresponds to a bacteria count of ~1-8×10$^{8-12}$ bacteria per ml. The biochemical analysis and resistance determination of the bacteria were conducted with the VITEK2 system according to the M100-S14 guidelines from the NCCLS (2004).

To check sensitivity of medically significant pathogens against antibiotics and sulfonamides, in accordance with the NCCLS guidelines, Müller-Hinton media were used (Deutsche Gesellschaft für Hygiene und Mikrobiologie (DGHM), Institute of Hygiene and Microbiology, University of Bonn, Germany):
a) Müller-Hinton broth (Oxoid, Wesel, Germany)
2.0 g/l beef, dried infusion from 300 g, 17.5 g/l casein hydrolyzate,
1.5 g/l starch, pH: 7.4+0.2
b) Müller-Hinton agar (Oxoid, Wesel, Germany)
2.0 g/l beef, dried infusion from 300 g, 17.5 g/l casein hydrolyzate,
1.5 g/l starch, pH: 7.4+0.2
13 g/l agar-agar
b) Procedure for the Phototoxicity Test:

200 µl of a bacterial suspension (bacterial density: $10^8$-$10^{12}$/ml) were incubated with 200 µl of each of various concentrations of the photosensitizers to be tested at room temperature for 10 min or 30 min. Thereafter, the bacteria were washed twice with distilled water and resuspended in 200 µl of distilled water, and the entire volume was transferred to a 96-well microtiter plate and then irradiated. The photosensitizers used were dissolved in distilled water and various dilution series were prepared (0 µM, 1 µM, 10 µM, 100 µM).

For sensitization, the Omnicure Series 2000 lamp (Photonics Solutions Inc., Edinburgh, UK) was used, which emits light from a range from 390 nm to 500 nm and has emission maxima $E_{max}$ at 405 nm and 436 nm. The power applied in each case was 50 mW/cm$^2$.

Irradiated and unirradiated samples were used as controls. Likewise run were bacterial suspensions incubated only with photosensitizer (dark control).

The determination of the colony-forming units (CFU) per ml was conducted by the method published by Miles and Misra (Miles, A A; Misra, S S, Irwin, J O (1938 November). "The estimation of the bactericidal power of the blood.". *The Journal of hygiene* 38 (6): 732-49). For this purpose, serial dilutions from $10^{-2}$ to $10^{-9}$ of the corresponding bacterial suspension were prepared. 3×20 µl of each of the corresponding bacterial dilutions were then dripped onto Müller-Hinton plates and incubated at 37° C. for 24 h. Thereafter, the number of surviving colony-forming units (CFU) was determined. Each of the experiments was repeated three times.
c) Result of the Phototoxicity Experiments:

The results of the phototoxicity experiments are shown in FIGS. 1-7.

FIGS. 1-8 show the logarithmic decreases in the CFU/ml 24 h after irradiation and the corresponding controls (only irradiated bacteria; bacteria incubated with photosensitizer but not irradiated; untreated bacteria) for the respective photosensitizer specified.

Each of the colony-forming units (CFU) per ml reported is the median from three experiments.

FIG. 1 shows the effect of flavin FL-09 (iodide of the compound having the formula (36)) on *E. coli* and *S. aureus*.

Figure 1A:
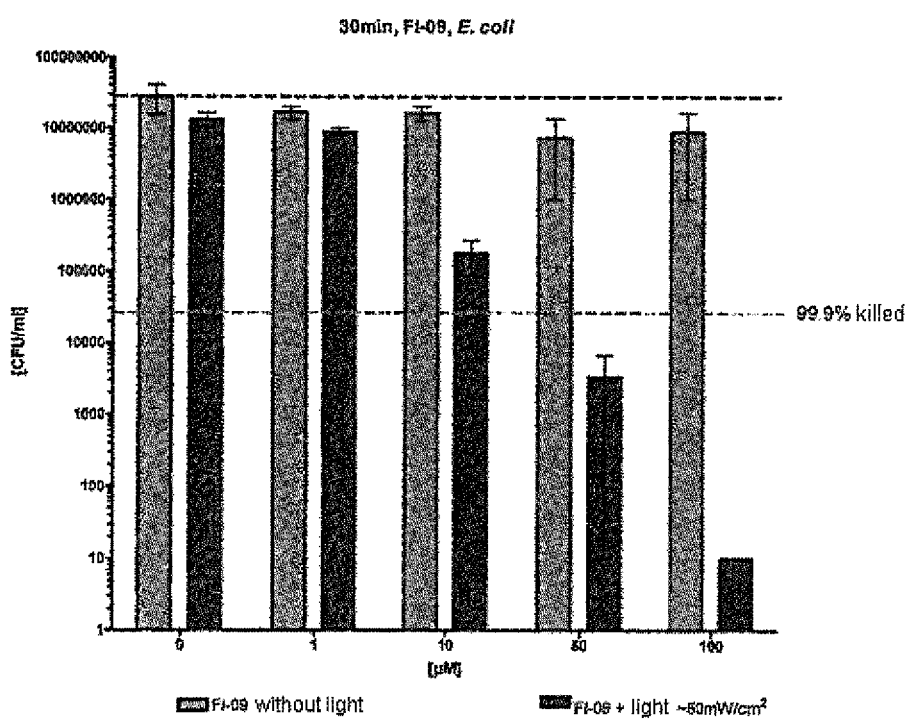
FIG. 1a) shows the results of incubation of *Escherichia coli* samples with FL-09 for 30 minutes.

FIG. 1*a*: *E. coli* samples were incubated with various concentrations (0 µM, 1 µM, 10 µM, 50 µM, 100 µM) of flavin FL-09 for 30 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 µM flavin FL-09, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 1B:
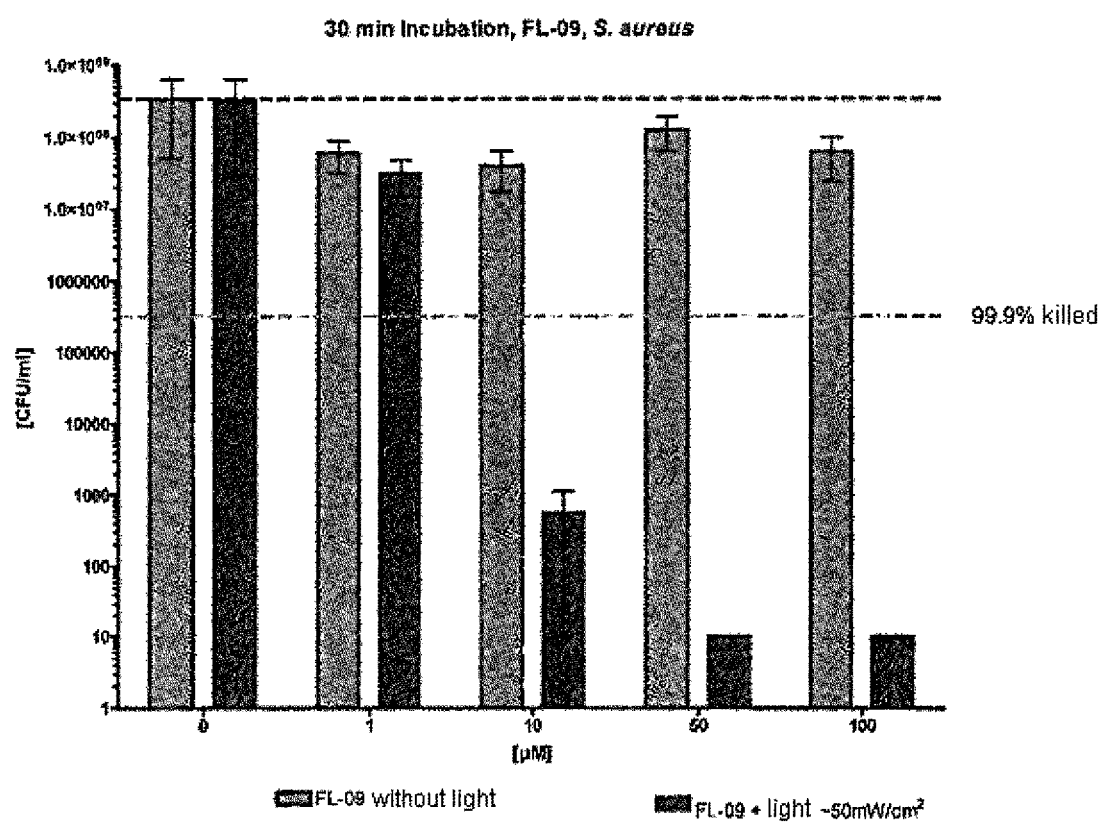
FIG. 1b) shows the results of incubation of *Staphylococcus aureus* samples with FL-09 for 30 minutes.

FIG. 1*b*: *S. aureus* samples were incubated with various concentrations (0 µM, 1 µM, 10 µM, 50 µM, 100 µM) of flavin FL-09 for 30 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 µM flavin FL-09, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 2:
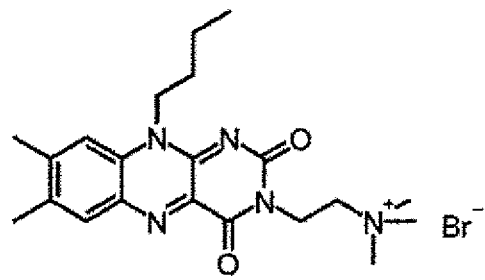
FIG. 2 shows the structural formula of Flavin FL-11.

FIG. 2 shows the effect of flavin FL-11 (bromide of the compound having the formula (32)) on *E. coli* and *S. aureus*.

Figure 2A:
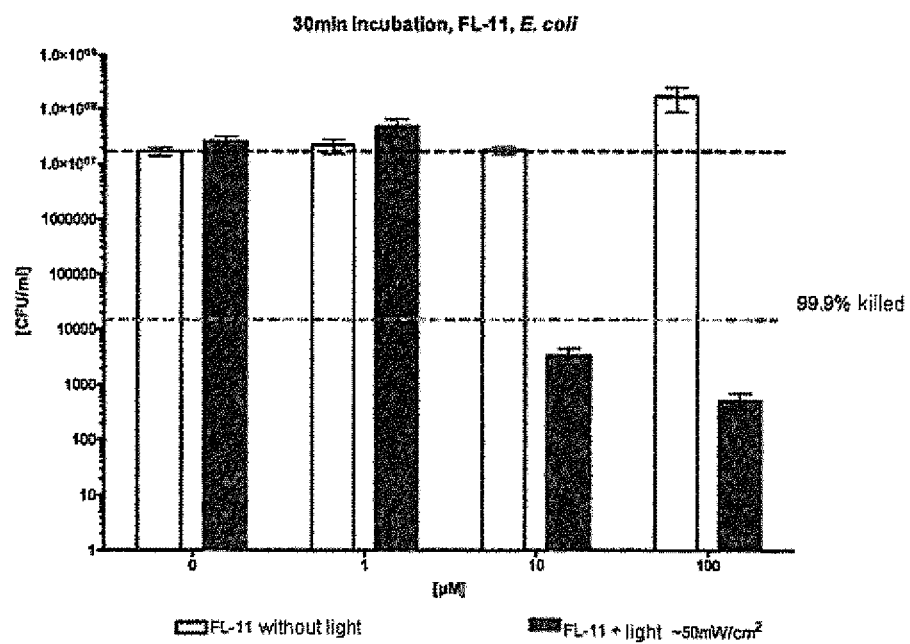
FIG. 2a) shows the results of incubation of *Escherichia coli* samples with FL-11 for 30 minutes.

FIG. 2*a*: *E. coli* samples were incubated with various concentrations (0 µM, 1 µM, 10 µM, 100 µM) of flavin FL-11 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-11, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

FIG. 2*b*: *S. aureus* samples were incubated with various concentrations (0 µM, 1 µM, 10 µM, 50 µM, 100 µM) of flavin FL-11 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-11, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 3:
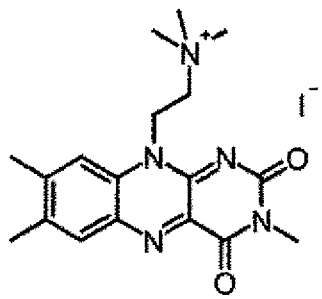
FIG. 3 shows the structural formula of Flavin FL-12.

FIG. 3 shows the effect of flavin FL-12 (iodide of the compound having the formula (30)) on *E. coli* and *S. aureus*.

Figure 3A:
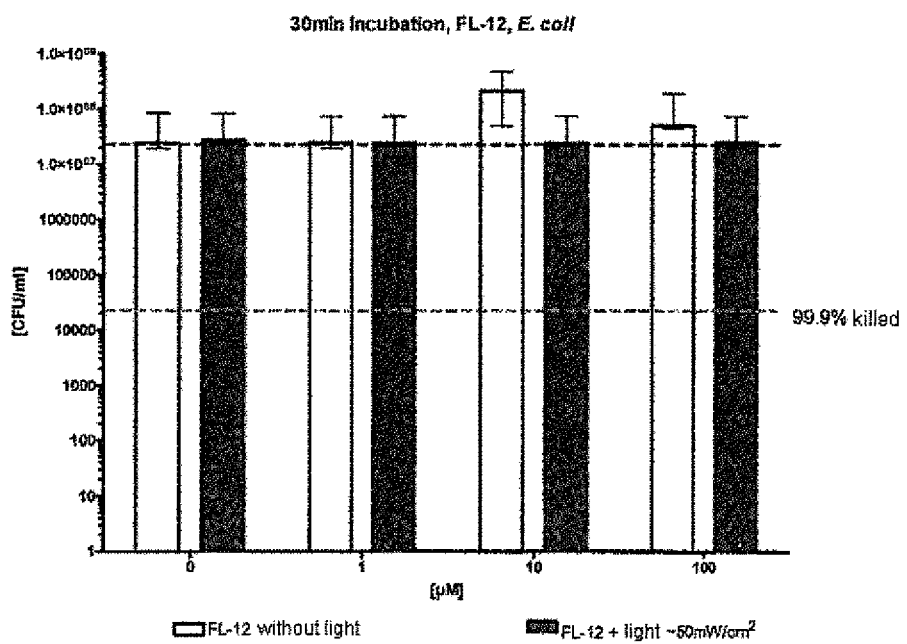
FIG. 3a) shows the results of incubation of *Escherichia coli* samples with FL-12 for 30 minutes.

FIG. 3*a*: *E. coli* samples were incubated with various concentrations (0 µM, 1 µM, 10 µM, 100 µM) of flavin FL-12 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-12, no light). The dotted line marked "99.9% killed" indicates a decrease in the CFU/ml by 3 log$_{10}$ stages; this corresponds to a decrease by 99.9% ("antibacterial action"). N=3; median CFU/ml+SEM.

FIG. 3*b*; *S. aureus* samples were incubated with various concentrations (0 µM, 1 µM, 10 µM, 50 µM, 100 µM) of flavin FL-12 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-12, no light). The dotted line marked "99.9% killed" indicates a decrease in the CFU/ ml by 3 $\log_{10}$ stages; this corresponds to a decrease by 99.9% ("antibacterial action"). N=3; median CFU/ml±SEM.

Figure 4:
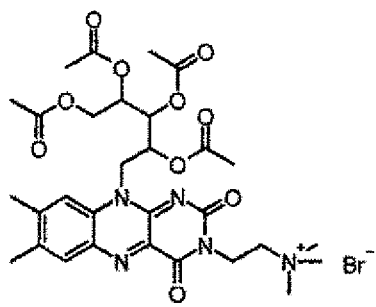
FIG. 4 shows the structural formula of Flavin FL-14.

FIG. 4 shows the effect of flavin FL-14 (bromide of the compound having the formula (35)) on *E. coli* and *S. aureus*.

Figure 4A:
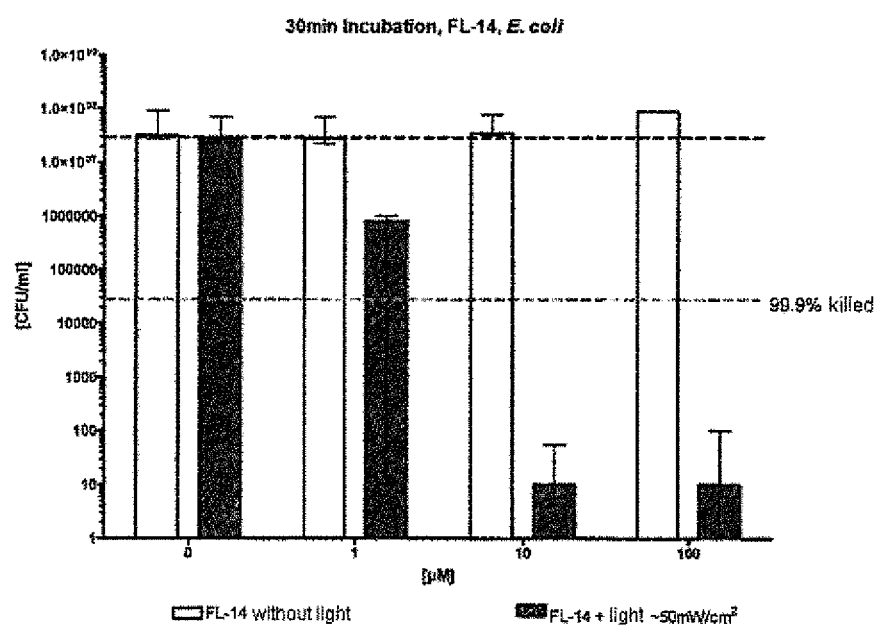
FIG. 4a) shows the results of incubation of *Escherichia coli* samples with FL-14 for 30 minutes.

FIG. 4a: *E. coli* samples were incubated with various concentrations (0 µM, 1 µM, 10 µM, 100 µM) of flavin FL-14 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-14, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 4B:
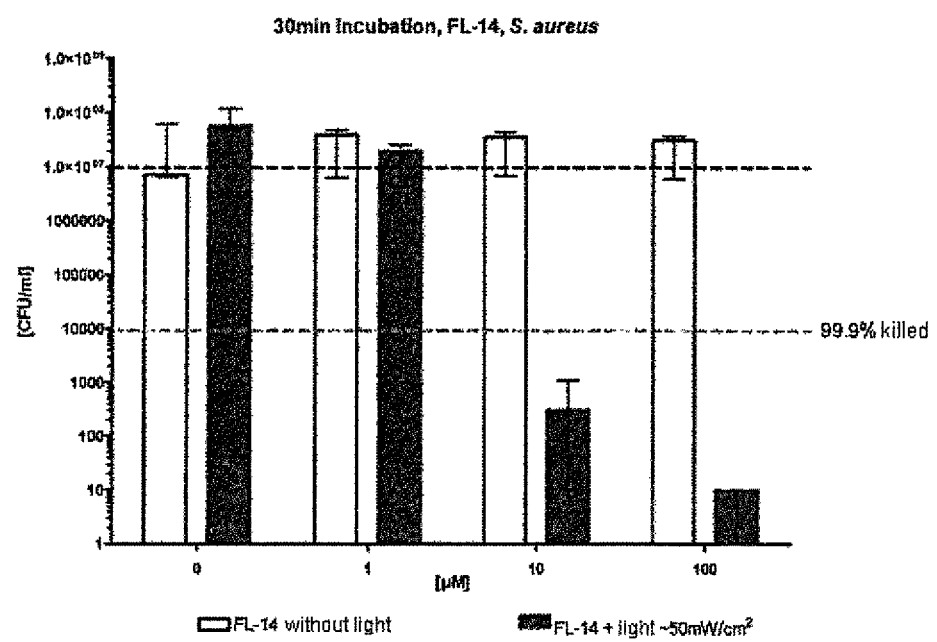
FIG. 4b) shows the results of incubation of *Staphylococcus aureus* samples with FL-14 for 30 minutes.

FIG. 4b: *S. aureus* samples were incubated with various concentrations (0 µM, 1 µM, 10 µM, 50 µM, 100 µM) of flavin FL-14 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-14, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 5:
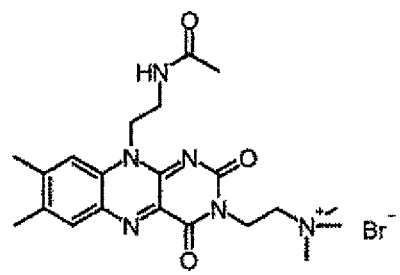
FIG. 5 shows the structural formula of Flavin FL-16.

FIG. 5 shows the effect of flavin FL-16 (bromide of the compound having the formula (33)) on *E. coli* and *S. aureus*.

Figure 5A:
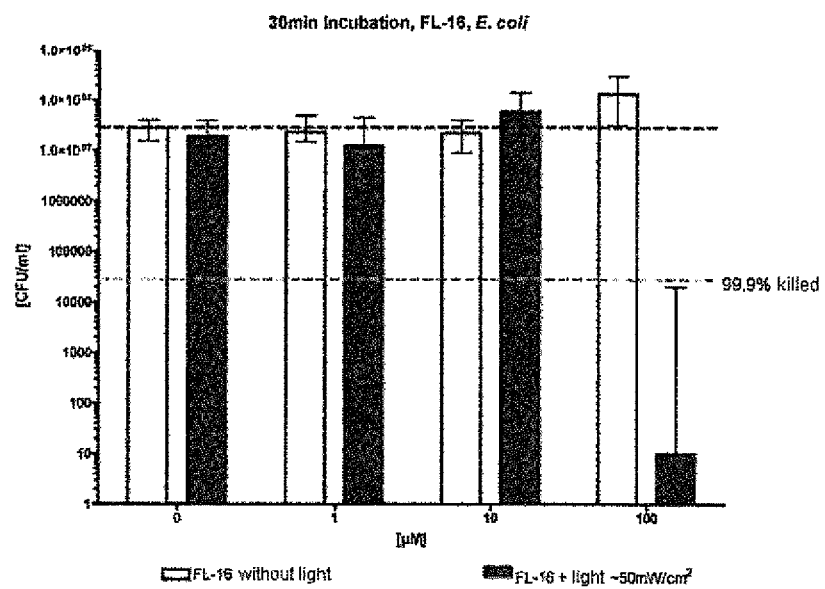
FIG. 5a) shows the results of incubation of *Escherichia coli* samples with FL-16 for 30 minutes.

FIG. 5a: *E. coli* samples were incubated with various concentrations (0 µM, 1 µM, 10 µM, 100 µM) of flavin FL-16 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-16, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 5B:
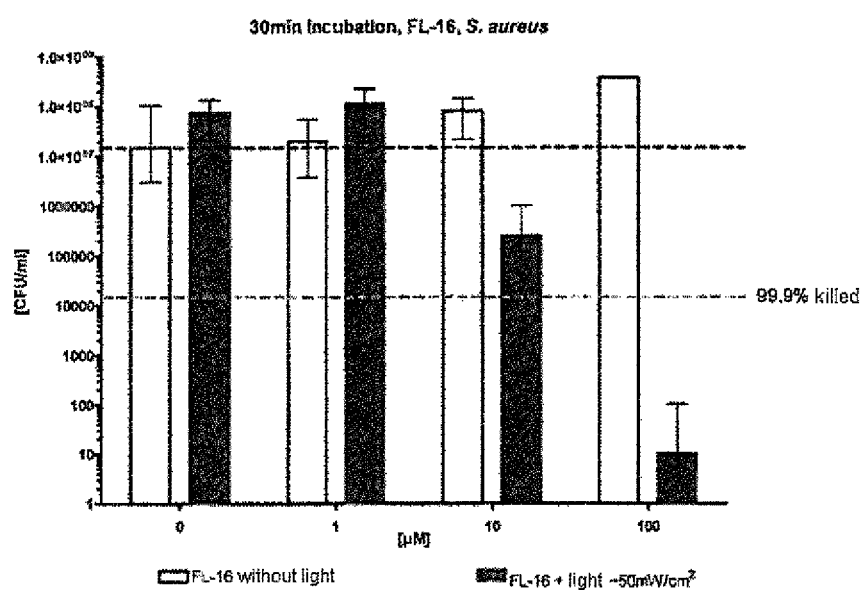
FIG. 5b) shows the results of incubation of *Staphylococcus aureus* samples with FL-16 for 30 minutes.

FIG. 5b: *S. aureus* samples were incubated with various concentrations (0 µM, 1 µM, 10 µM, 50 µM, 100 µM) of flavin FL-16 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-16, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 6:
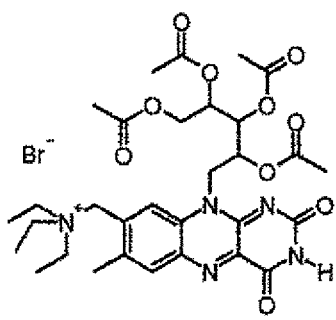
FIG. 6 shows the structural formula of Flavin FL-18.

FIG. 6 shows the effect of flavin FL-18 (bromide of the compound having the formula (37)) on *E. coli* and *S. aureus*.

Figure 6A:
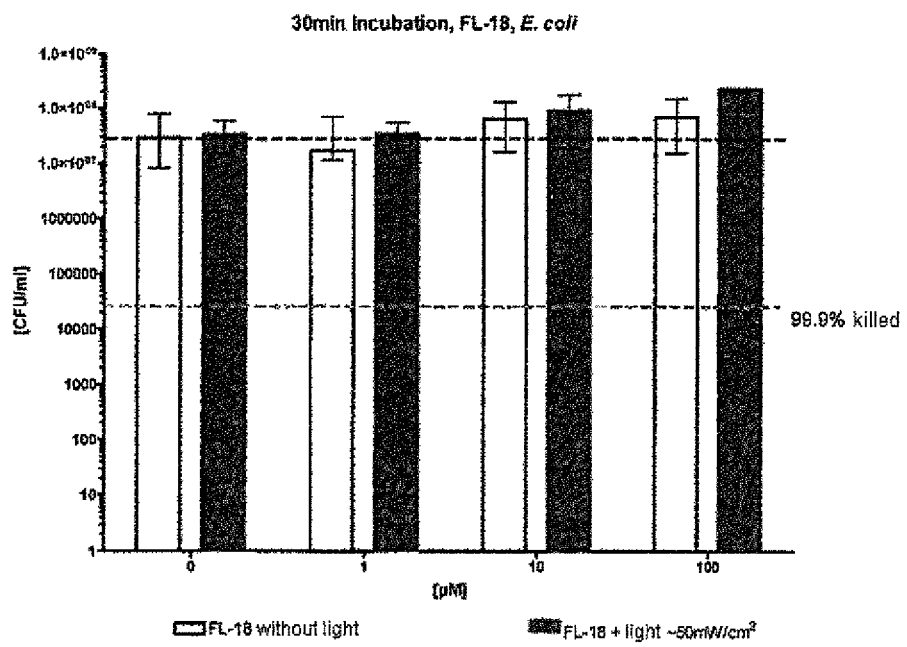
FIG. 6a) shows the results of incubation of *Escherichia coli* samples with FL-18 for 30 minutes.

FIG. 6a: *E. coli* samples were incubated with various concentrations (0 µM, 1 µM, 10 µM, 100 µM) of flavin FL-18 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-18, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 6B:
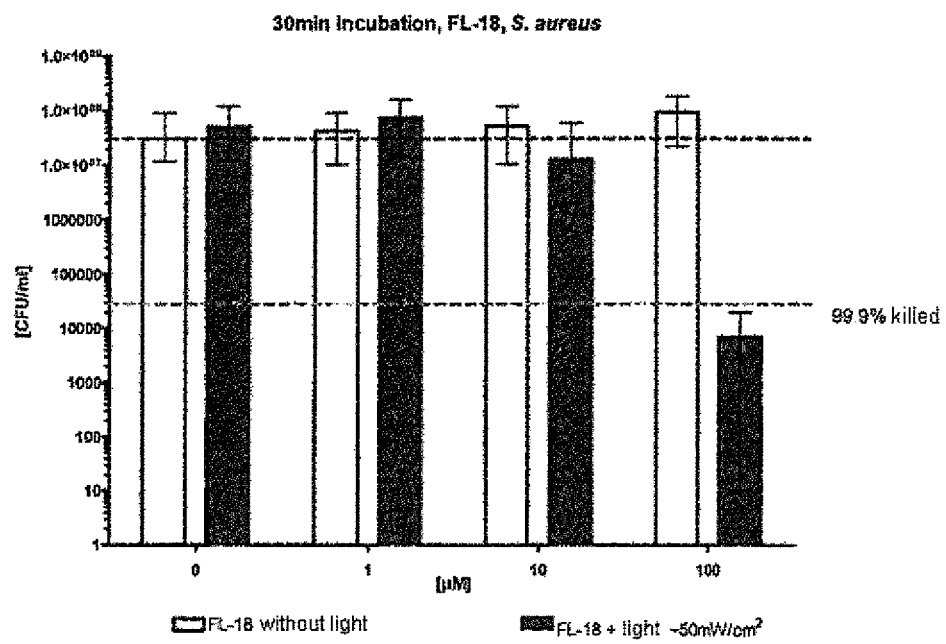
FIG. 6b) shows the results of incubation of *Staphylococcus aureus* samples with FL-18 for 30 minutes.

FIG. 6b: *S. aureus* samples were incubated with various concentrations (0 µM, 1 µM, 10 µM, 50 µM, 100 µM) of flavin FL-18 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-18, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 7:
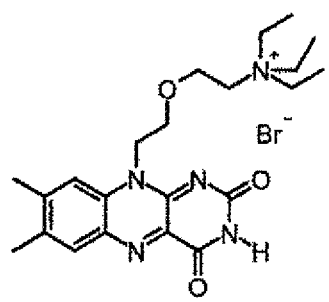
FIG. 7 shows the structural formula of Flavin FL-25.

FIG. 7 shows the effect of flavin FL-25 (bromide of the compound having the formula (31)) on *E. coli* and *S. aureus*.

Figure 7A:
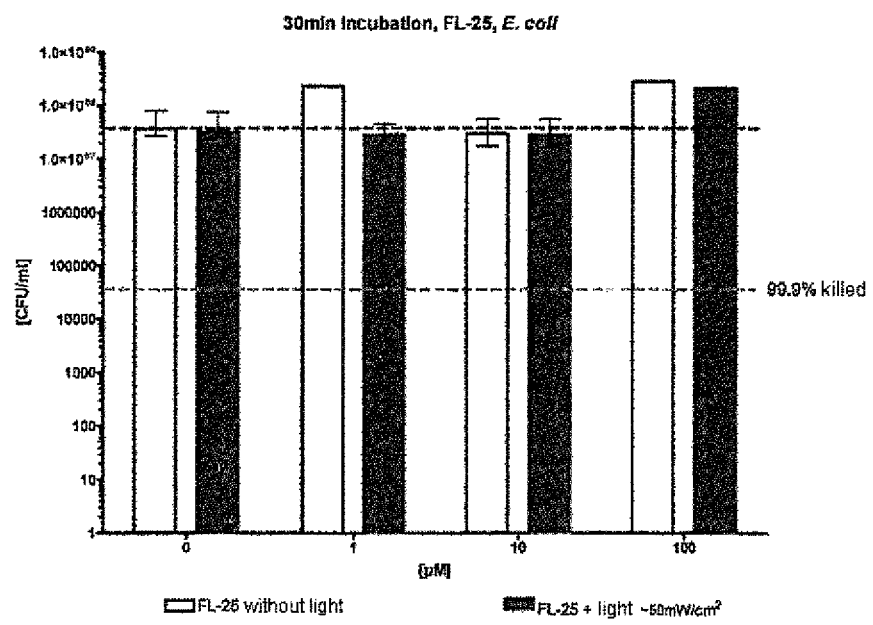
FIG. 7a) shows the results of incubation of *Escherichia coli* samples with FL-25 for 30 minutes,
FIG. 7b) shows the results of incubation of *Staphylococcus aureus* samples with FL-25 for 30 minutes.

FIG. 7a: *E. coli* samples were incubated with various concentrations (0 µM, 1 µM, 10 µM, 100 µM) of flavin FL-25 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-25, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 7B:
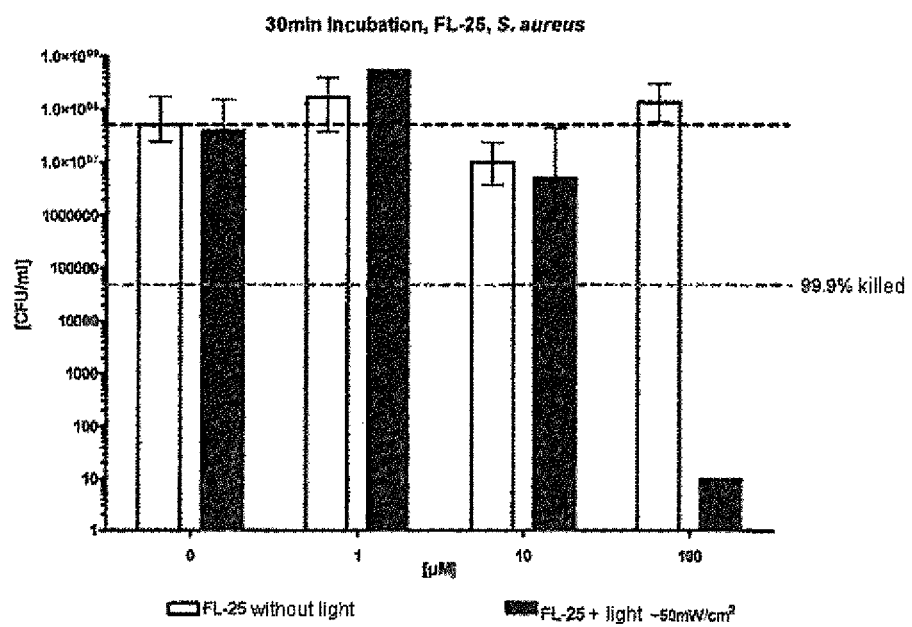

FIG. 7b: *S. aureus* samples were incubated with various concentrations (0 µM, 1 µM, 10 µM, 50 µM, 100 µM) of flavin FL-25 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 µM flavin FL-25, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

Figure 8:
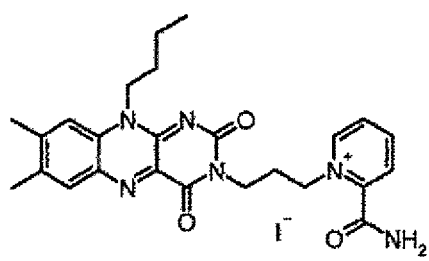
FIG. 8 shows the structural formula of Flavin FL-09b.

FIG. 8 shows the effect of flavin FL-9a (iodide of the compound having the formula (43)) on *E. coli* and *S. aureus*.

Figure 8A:
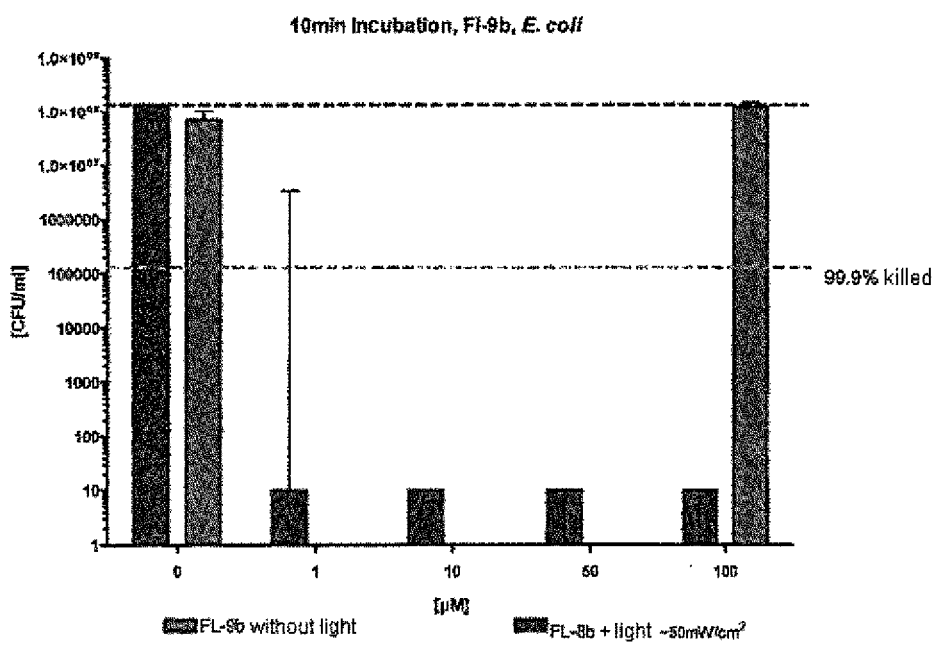
FIG. 8a) shows the results of incubation of *Escherichia coli* samples with FL-9b for 10 minutes.
Figure 8B:
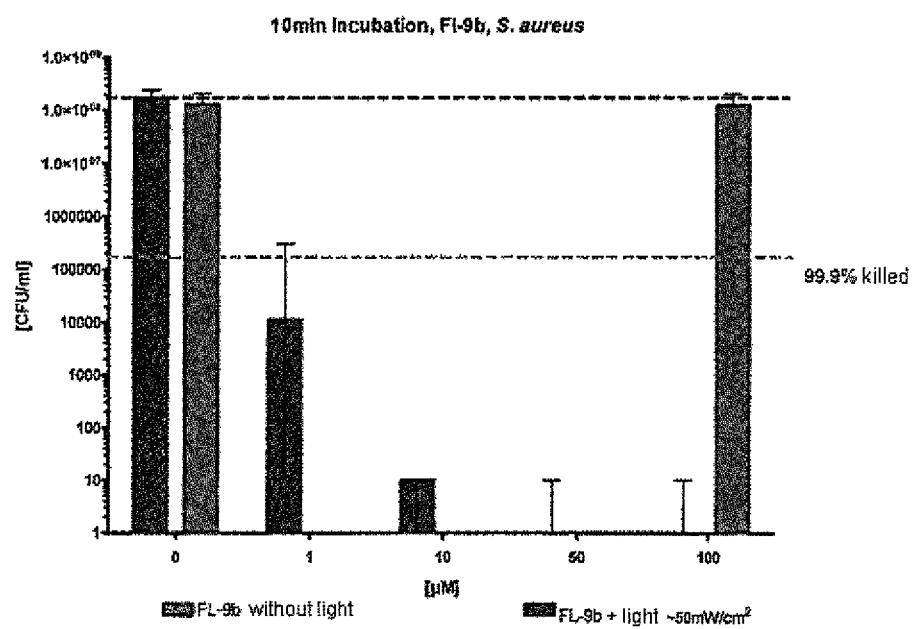
FIG. 8b) shows the results of incubation of *Staphylococcus aureus* samples with FI-9b for 10 minutes.

FIG. 8a: *E. coli* was incubated with various concentrations of FL-09b [µM] for 10 min, then the samples were irradiated at 50 mW/cm$^2$ (210 sec; 10.5 J/cm$^2$). 24 h later, the surviving colonies were counted (CFU/ml). Gray bar: dark control without light. Red bar: incubated with photosensitizer and irradiated. The black line indicates the dark control reference (no photosensitizer incubation, no light). The green line indicates a decrease in the CFU/ml by 3 log 10 stages; this corresponds to a decrease by 99.9% ("antibacterial action"). N=3; median CFU/ml±SEM.

FIG. 8a: *S. aureus* was incubated with various concentrations of FL-09b [µM] for 10 min, then the samples were irradiated at 50 mW/cm$^2$ (210 sec; 10.5 J/cm$^2$). 24 h later, the surviving colonies were counted (CFU/ml). Gray bar: dark control without light. Red bar: incubated with photosensitizer and irradiated. The black line indicates the dark control reference (no photosensitizer incubation, no light). The green line indicates a decrease in the CFU/ml by 3 log 10 stages; this corresponds to a decrease by 99.9% ("antibacterial action"). N=3; median CFU/ml±SEM.

As apparent from FIGS. 1-8, irradiation of the microorganisms used *Staphylococcus aureus* (*S. aureus*) and *Escherichia coli* (*E. coli*) at a light dose of 10.5 J/cm$^2$ with blue light (390 nm-500 nm) in the absence of a photosensitizer (0 µM of the respective flavin) has no influence on the number of surviving microorganisms in comparison to the unexposed control.

In addition, the results shown in FIGS. 1-8 show that the incubation (10 min or 30 min) of the respective photosensitizer with the microorganisms without subsequent exposure likewise has no influence on the number of surviving microorganisms.

As apparent from FIGS. 1-8, there is a decrease in the CFU/ml and hence inactivation of *E. coli* and *S. aureus* after incubation (10 min or 30 min) of the microorganisms as a function of the concentration used of the respective photosensitizers, and subsequent irradiation with a light dose of 10.5 J/cm$^2$.

The effectiveness of phototoxicity with respect to bacteria after irradiation was defined according to the following guidelines for hand hygiene in the health sector (Boyce, J. M., and D. Pittet. 2002. Guideline for Hand Hygiene in Health- Care Settings: recommendations of the Healthcare Infection Control Practices Advisory Committee and the HICPAC/SHEA/APIC/IDSA Hand Hygiene Task Force. Infect Control Hosp Epidemiol 23: p. 3-40):

reduction in the CFU/ml by 1 $\log_{10}$ stage $\hat{=}$ 90% effectiveness reduction in the CFU/ml by 3 $\log_{10}$ stages $\hat{=}$ 99.9% effectiveness reduction in the CFU/ml by 5 $\log_{10}$ stages $\hat{=}$ 99.999% effectiveness For effective inactivation, the decrease of ≥3 $\log_{10}$ stages can therefore be adopted, and S. aureus and E. coli were chosen as examples of representatives from the group of the Gram-positive and Gram-negative bacteria (see Boyce J. M and D. Pittet 2009).

The concentration required to achieve a reduction by ≥3 $\log_{10}$ stages is shown in table 2.

TABLE 2

Summary of photodynamic inactivation

| Photosensitizer | Required concentration [µM] to achieve a reduction by ≥3log₁₀ stages (decrease by 99.9%), irradiation at 10.5 J/cm² | |
|---|---|---|
| | E. coli | S. aureus |
| FL-09 | 50 | 10 |
| FL-09b | 1 | 1 |
| FL-11 | 10 | 10 |
| FL-12 | —(*) | 100 |
| FL-14 | 10 | 10 |
| FL-16 | 100 | 100 |
| FL-18 | —(*) | 100 |
| FL-25 | —(*) | 100 |

(*)reduction less than 1log₁₀ under the conditions examined so far

What is claimed is:

1. A compound having the formula (1):

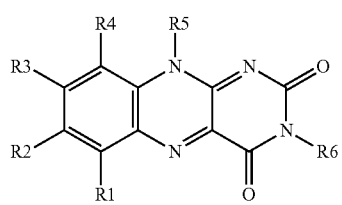

(1)

where A) only 1 R1, R2, R3 or R4 radical is an organic radical of the general formula -(C(D)(E))$_h$-X or -(C(D)(E))$_k$-aryl-(C(D)(E))$_l$-X, where h is an integer from 1 to 20 and k, l are each independently an integer from 0 to 6, where D and E are each independently hydrogen, halogen, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, and where X is an organic radical having only one quaternary nitrogen atom and aryl is a substituted or unsubstituted aromatic system or a substituted or unsubstituted heteroaromatic system which does not contain any nitrogen atom, and where the R1, R2, R3 or R4 radicals which are not -(C(D)(E))$_h$-X or -(C(D)(E))$_k$-aryl-(C(D)(E))$_l$-X may be the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where each of the R5 and R6 radicals is the same or different and is independently hydrogen, alkyl having 1 to 20 carbon atoms, alkenyl having 1 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms, or where B) only 1 R5 or R6 radical is an organic radical of the general formula -(C(D)(E))$_h$-X or -(C(D)(E))$_k$-aryl-(C(D)(E))$_l$-X, where h is an integer from 1 to 20 and k, l are each independently an integer from 0 to 6, where D and E are each independently hydrogen, halogen, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, and where X is an organic radical having only one quaternary nitrogen atom and aryl is a substituted or unsubstituted aromatic system or a substituted or unsubstituted heteroaromatic system which does not contain any nitrogen atom, and where the R5 or R6 radical which is not -(C(D)(E))$_h$-X or -(C(D)(E))$_k$-aryl-(C(D)(E))$_l$-X is hydrogen, alkyl having 1 to 20 carbon atoms, alkenyl having 2 to 20 carbon atoms, cycloalkyl having 3 to 20 carbon atoms, ether having 2 to 20 carbon atoms, thioether having 2 to 20 carbon atoms, cycloalkenyl having 3 to 20 carbon atoms, aryl having 5 to 20 carbon atoms or heteroaryl having 4 to 20 carbon atoms, which does not contain any nitrogen atoms, and where the R1 to R4 radicals may be the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl having 4 to 20 carbon atoms, which does not contain any nitrogen atoms.

2. A compound as claimed in claim 1, where the R1 and R4 radicals, which may be the same or different, are each independently hydrogen or methyl, and where only 1 R2, R3, R5 and R6 radical is an organic radical of the general formula -(C(D)(E))$_h$-X or -(C(D)(E))$_k$-aryl-(C(D)(E))$_l$-X.

3. A compound as claimed in claim 1, where X is a radical of the general formula (2):

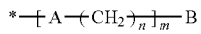
(2)

and where A is an oxygen or sulfur atom and where n is an integer from 1 to 8 and m is an integer from 0 to 100, and where B is a radical of the formula (3), (4a), (4b), (5a) or (5b):

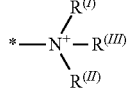
(3)

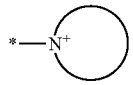
(4a)

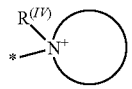
(4b)

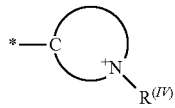
(5a)

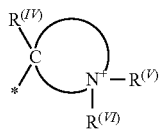
(5b)

and where each of the $R^{(I)}$, $R^{(II)}$, $R^{(III)}$, $R^{(IV)}$ and $R^{(V)}$ radicals is independently a C1-C20 aryl, a C1-C20 alkyl which may be straight-chain or branched, or a C1-C20 ether, and where the radical having the formula (4a) and the radical having the formula (5a):

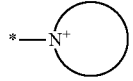
(4a)

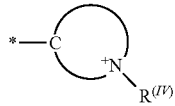
(5a)

is a substituted or unsubstituted heterocyclic radical having 5 to 7 ring atoms including at least one 1 carbon atom and 1 nitrogen atom and optionally 1 or 2 oxygen or sulfur atoms, where 1 nitrogen atom forms a double bond, and where the radical having the formula (4b) and the radical having the formula (5b):

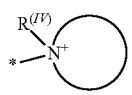
(4b)

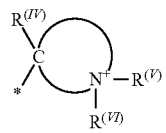
(5b)

is a substituted or unsubstituted heterocyclic radical having 5 to 7 ring atoms including at least one 1 carbon atom and 1 nitrogen atom and optionally 1 or 2 oxygen or sulfur atoms, where 1 nitrogen atom forms a single bond.

4. A compound as claimed in claim 1, where the 10H-benzo[g]pteridine-2,4-dione derivative of the formula (1) is selected from the group consisting of compounds having the formulae (30) to (43):

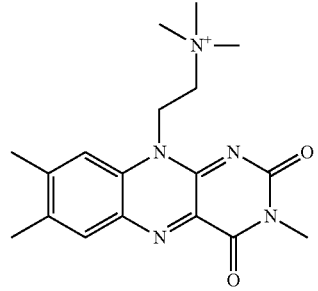
(30)

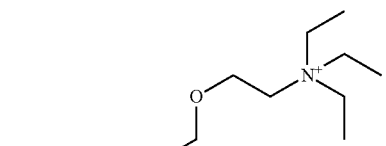
(31)

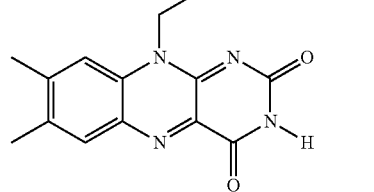
(32)

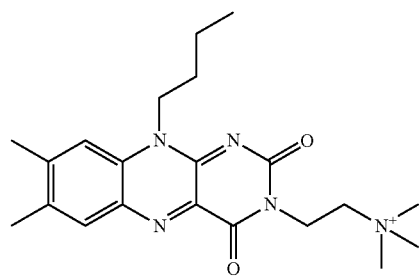
(33)

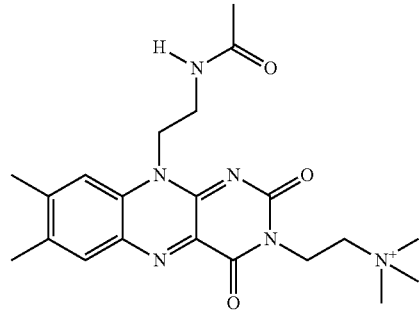

-continued
(34)
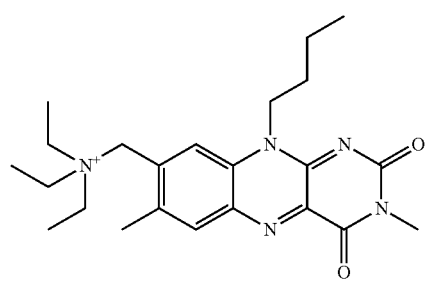
(35)
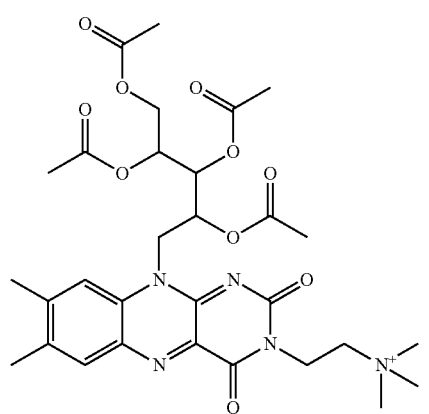
(36)
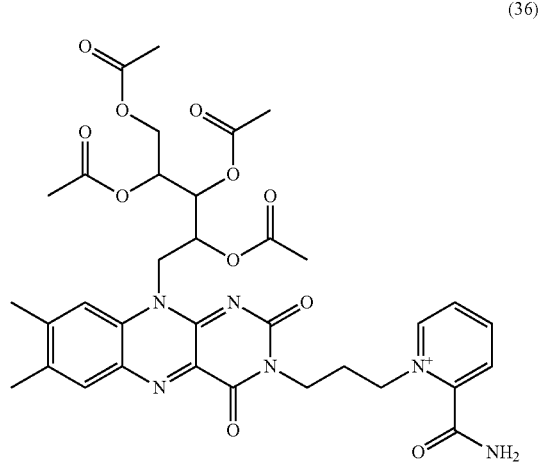
(37)
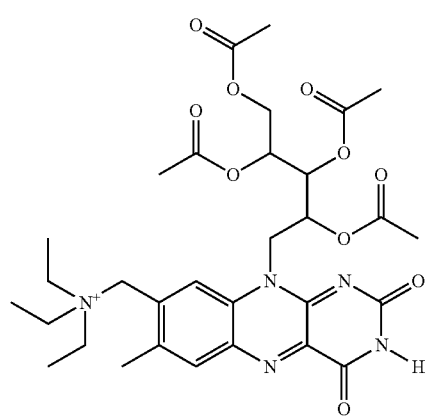
-continued
(38)
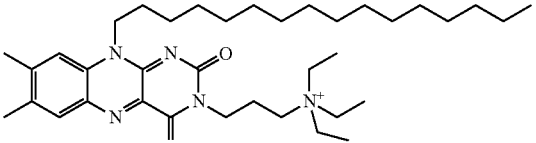
(39)
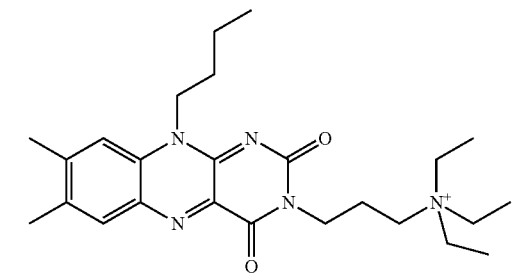
(40)
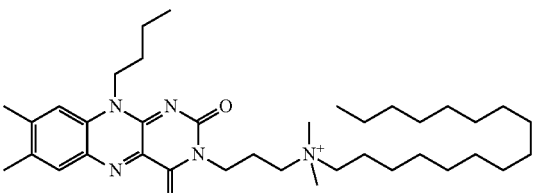
(41)
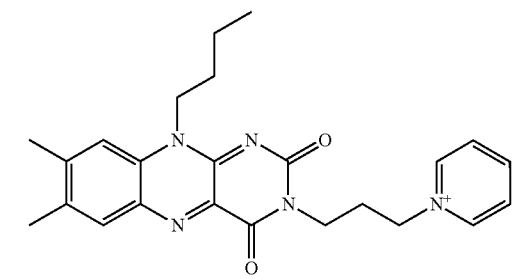
(42)
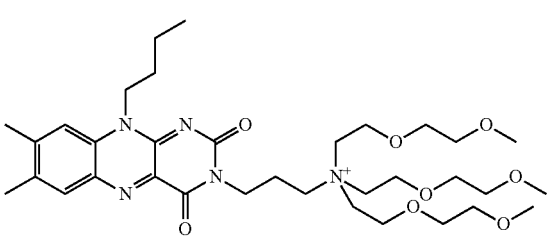
(43)
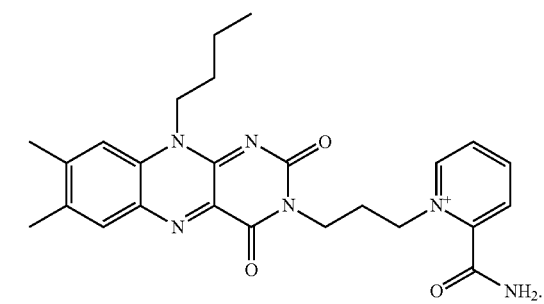

5. A process for inactivating microorganisms located on or within a subject in need of such inactivation, said process comprising applying upon said subject a compound as claimed in claim 1 as a photosensitizer for inactivation of microorganisms.

6. The process as claimed in claim 5, wherein said microorganisms are selected from the group consisting of viruses, archaea, bacteria, bacterial spores, fungi, fungal spores, protozoa, algae and blood-transmissible parasites.

7. The process as claimed in claim 5, wherein the photosensitizer is applied upon said subject in at least one selected from the group consisting of the cleaning of teeth, dentures, and dental braces, treatment of a disorder of at least one of dental tissue and of the periodontium.

8. The process as claimed in claim 5, wherein the photosensitizer is applied upon said subject for treatment of an infectious skin disease.

9. A process for inactivating microorganisms located on or within an object, said process comprising applying to an object during at least one of surface cleaning and coating of said object a compound as claimed in claim 1.

10. The process as claimed in claim 9, wherein the object is selected from the group consisting of medical products, food or drink packaging and hygiene articles.

11. A pharmaceutical composition comprising at least one selected from the group consisting of a compound as claimed in claim 1 and a pharmacologically acceptable salt, ester and complex thereof and at least one pharmacologically acceptable excipient.

12. A coated article, wherein a surface of the article is coated with at least one compound as claimed in claim 1.

13. A process for preparing the compound of claim 1, wherein the process comprises the following steps:

(A) reducing a substituted nitroaniline of the formula (22) to a substituted o-phenylenediamine of the formula (23)

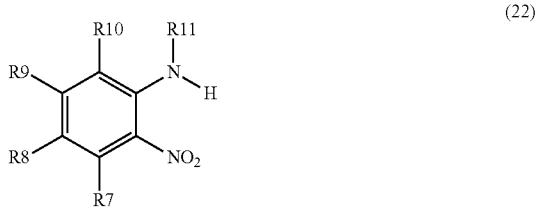

(22)

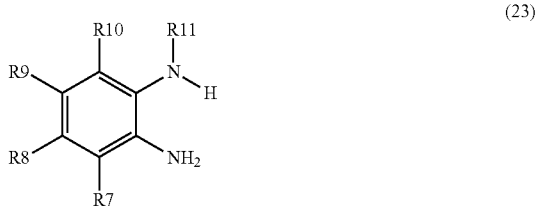

(23)

where each of the R7 to R10 radicals is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms, or an organic radical of the general formula -(C(D)(E))$_h$-OH, -(C(D)(E))$_k$-aryl-(C(D)(E))$_l$-OH, -(C(D)(E))$_h$-X or -(C(D)(E))$_k$-aryl-(C(D)(E))$_l$-X, and where the R11 radical is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl which does not contain any nitrogen atom and has 4 to 20 carbon atoms or an organic radical of the general formula -(C(D)(E))$_h$-OH or -(C(D)(E))$_k$-aryl-(C(D)(E))$_l$-OH, -(C(D)(E))$_h$-X or -(C(D)(E))$_k$-aryl-(C(D)(E))$_l$-X, (B) condensing the substituted o-phenylenediamine of the formula (23) obtained in step (A) with alloxane or the hydrate thereof to obtain a compound having the formula (24):

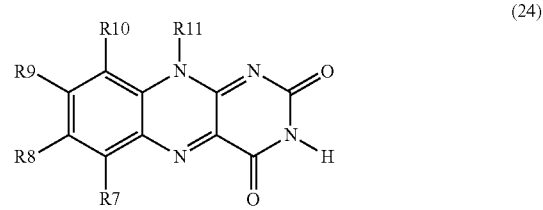

(24)

(C) optionally reacting the compound of the formula (24) obtained in step (B) with an alkylating agent of the general formula T-alkyl, T-alkenyl, T-cycloalkyl, T-cycloalkenyl, T-(C(D)(E))$_h$-OH, T-(C(D)(E))$_k$-aryl-(C(D)(E))$_l$-OH, T-aryl, T-(C(D)(E))$_h$-X or T-(C(D)(E))$_k$-aryl-(C(D)(E))$_l$-X, where the T radical is hydrogen, chlorine, bromine, iodine, p-toluenesulfonyl (OTs), methanesulfonyl (OMs), OH or R$_2$S$^+$, where each R may be the same or different to obtain a compound having the formula (25):

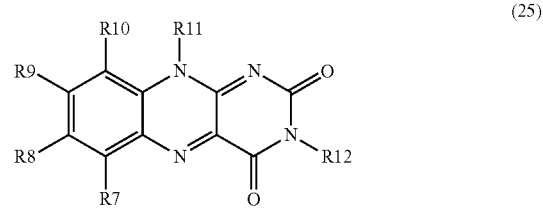

(25)

(D) optionally reacting the compound of the formula (24) obtained in step (B) or the compound of the formula (25) obtained in step (C) with tosyl chloride, mesyl chloride or iodine, optionally in the presence of a catalyst, and subsequently with an organic compound containing at least one tertiary nitrogen atom, when none of the R7 to R12 radicals is an organic radical of the general formula -(C(D)(E))$_h$-X or -(C(D)(E))$_k$-aryl-(C(D)(E))$_l$-X and when 1 R7 to R12 radical is an organic radical of the general formula -(C(D)(E))$_h$-OH or -(C(D)(E))$_k$-aryl-(C(D)(E))$_l$-OH, to obtain the 10H-benzo[g]pteridine-2,4-dione derivative of the formula (1), with the proviso that only 1 R1 to R6 radical is an organic radical of the general formula -(C(D)(E))$_h$-X or -(C(D)(E))$_k$-aryl-(C(D)(E))$_l$-X, and where each h is an integer from 1 to 20 and k, l are each independently an integer from 0 to 6, where D and E are each independently hydrogen, halogen, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, and where each X is an organic radical having at least one quaternary nitrogen atom and each aryl is a substituted or unsubstituted aromatic system having 5 to 20 carbon atoms or a substituted or unsubstituted heteroaromatic system which does not contain any nitrogen atom and has 4 to 20 carbon atoms.

14. A process for preparing the compound of claim 1, wherein the process comprises the following steps:

(A) condensing an amine having the formula R11-NH$_2$ with a chlorouracil derivative of the formula (26), optionally in the presence of a catalyst to obtain a compound having the formula (27):

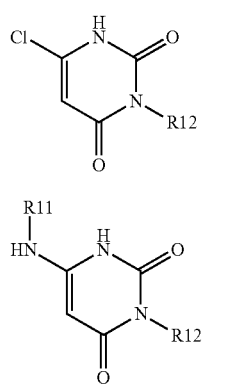

where each of the R11 or R12 radicals is the same or different and is independently hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atom, or an organic radical of the general formula -(C(D)(E))$_h$-OH or -(C(D)(E))$_k$-aryl-(C(D)(E))$_l$-OH, -(C(D)(E))$_h$-X or -(C(D)(E))$_k$-aryl-(C(D)(E))$_l$-X, (B) reacting the compound of the formula (27) obtained in step (A) with a nitroso compound of the formula (28) to obtain a compound of the formula (25):

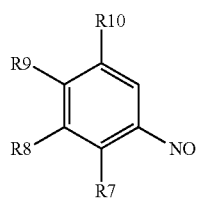

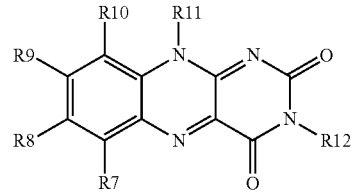

where each of the R7 to R10 radicals is the same or different and is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atom, or an organic radical of the general formula -(C(D)(E))$_h$-OH, -(C(D)(E))$_k$-aryl-(C(D)(E))$_l$-OH, -(C(D)(E))$_h$-X or -(C(D)(E))$_k$-aryl-(C(D)(E))$_l$-X, and (C) optionally reacting the compound of the formula (25) obtained in step (B) with tosyl chloride, mesyl chloride or iodine, optionally in the presence of a catalyst, and subsequently with an organic compound containing at least one tertiary nitrogen atom, when none of the R7 to R12 radicals is an organic radical of the general formula -(C(D)(E))$_h$-X or -(C(D)(E))$_k$-aryl-(C(D)(E))$_l$-X and when 1 R7 to R12 radical is an organic radical of the general formula -(C(D)(E))$_h$-OH or -(C(D)(E))$_k$-aryl-(C(D)(E))$_l$-OH, to obtain the 10H-benzo[g]pteridine-2,4-dione derivative of the formula (1), with the proviso that only 1 R1 to R6 radical is an organic radical of the general formula -(C(D)(E))$_h$-X or -(C(D)(E))$_k$-aryl-(C(D)(E))$_l$-X, and where each h is an integer from 1 to 20 and k, l are each independently an integer from 0 to 6, where D and E are each independently hydrogen, halogen, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, and where each X is an organic radical having only one quaternary nitrogen atom and each aryl is a substituted or unsubstituted aromatic system having 5 to 20 carbon atoms or a substituted or unsubstituted heteroaromatic system which does not contain any nitrogen atom and has 4 to 20 carbon atoms.

15. The process as claimed in claim 13, wherein the process comprises the following steps when none of the R7 to R12 radicals is an organic radical of the general formula -(C(D)(E))$_h$-X or -(C(D)(E))$_k$-aryl-(C(D)(E))$_l$-X and when 1 R7 to R10 radical is methyl:

(A) free-radically halogenating the compound (24) or (25) in the presence of a free-radical initiator to obtain a compound having the formula (24a-d) or (25a-d):

(24a) 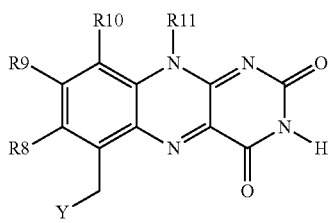

(24b) 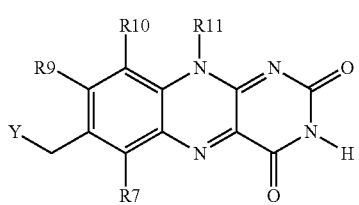

(24c) 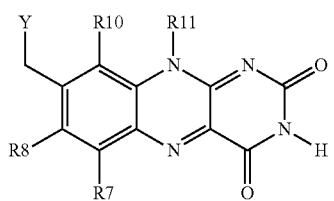

(24d) 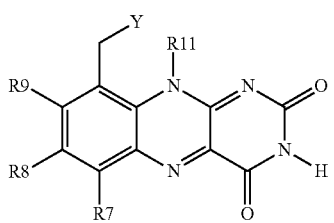

(25a) 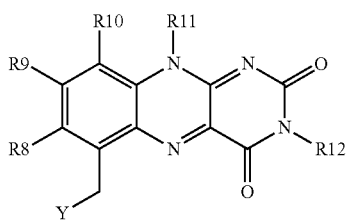

(25b) 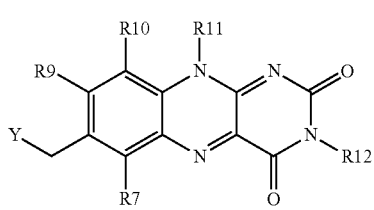

(25c) 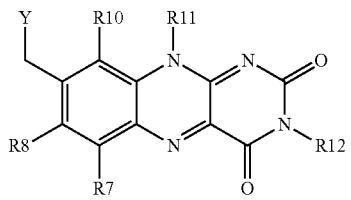

(25d) 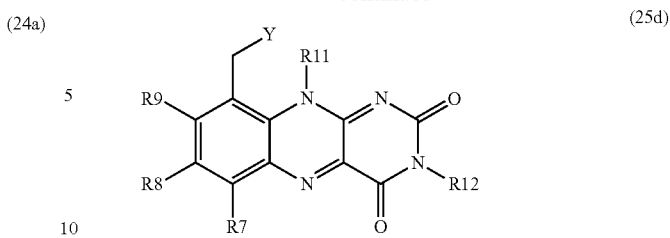

where the Y radical is Cl, Br or I, and

B) reacting the compound obtained in step (A) and having the formula (24a-24d) or (25a-25d) with an organic compound containing at least one tertiary nitrogen atom to obtain the 10H-benzo[g]pteridine-2,4-dione derivative of the formula (1).

16. A process for preparing a compound of claim 1, wherein the process comprises the following steps:

(A) preparing a substituted aniline having the formula (102a) or (102b) by (a) peptide coupling/reduction to an aniline having the formula (101) or (b) reductive amination of an aniline having the formula (101) with aldehydes or (c) Pd-catalyzed coupling of a halide of the formula (104) to an amine of the formula R11-NH$_2$ or (d) Pd-catalyzed coupling of an amine of the formula (100) to a halide of the formula R11-NH$_2$ a) 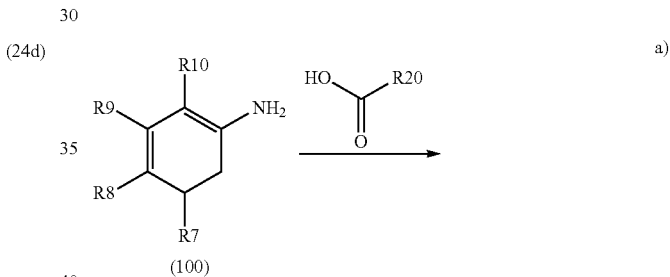

(100)

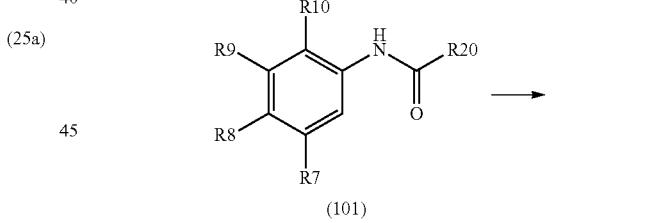

(101)

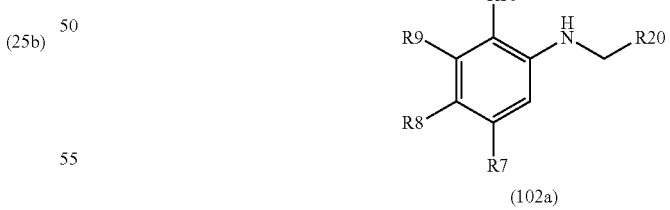

(102a)

b) 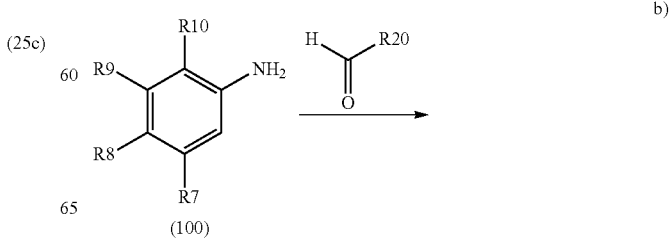

(100)

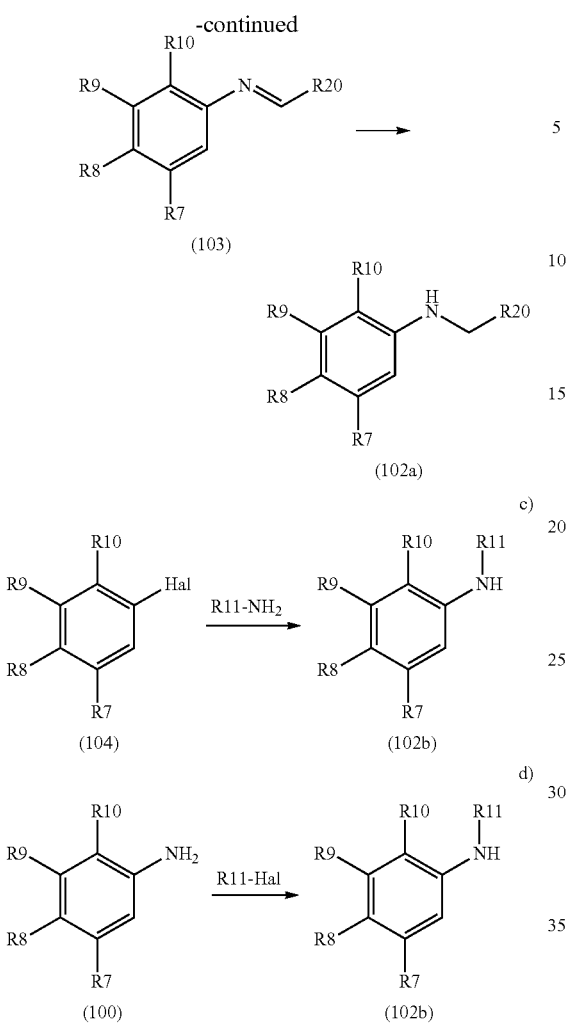

(103)

(102a)

c)

(104) → (102b)

d)

(100) → (102b)

where each of the R7 to R10 radicals, which may be the same or different, is independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula $-(C(D)(E))_h$-OH, $-(C(D)(E))_k$-aryl-$(C(D)(E))_l$-OH, $-(C(D)(E))_h$-X or $-(C(D)(E))_k$-aryl-$(C(D)(E))_l$-X, and where the R11 radical is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula $-(C(D)(E))_h$-OH or $-(C(D)(E))_k$-aryl-$(C(D)(E))_l$-OH, $-(C(D)(E))_h$-X or $-(C(D)(E))_k$-aryl-$(C(D)(E))_l$-X, and where the R20 radical is hydrogen, alkyl having 1 to 19 carbon atoms, alkenyl having 2 to 19 carbon atoms, ether having 1 to 19 carbon atoms, thioether having 1 to 19 carbon atoms, cycloalkyl having 3 to 19 carbon atoms, cycloalkenyl having 3 to 19 carbon atoms, aryl having 5 to 19 carbon atoms, heteroaryl having 4 to 19 carbon atoms, which does not contain any nitrogen atoms, or an organic radical of the general formula $-(C(D)(E))_{h-1}$-OH or $-(C(D)(E))_{k-1}$-aryl-$(C(D)(E))_{l-1}$-OH, $-(C(D)(E))_{h-1}$-X or $-(C(D)(E))_{k-1}$-aryl-$(C(D)(E))_{l-1}$-X, and where the Hal radical is fluorine, chlorine, bromine or iodine, (B) reacting the substituted aniline having the formula (102a) obtained in step (A) with violuric acid to obtain a compound of the formula (24z):

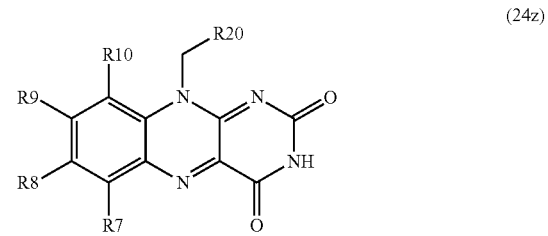

(24z)

or reacting the substituted aniline having the formula (102b) obtained in step (A) with violuric acid to obtain a compound of the formula (24):

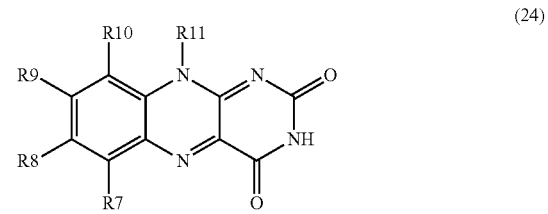

(24)

(C) optionally reacting the compound of the formula (24z) obtained in step (B) with an alkylating agent of the general formula T-alkyl, T-alkenyl, T-cycloalkyl, T-cycloalkenyl, T-$(C(D)(E))_h$-OH, T-$(C(D)(E))_k$-aryl-$(C(D)(E))_l$-OH, T-aryl, T-$(C(D)(E))_h$-X or T-$(C(D)(E))_k$-aryl-$(C(D)(E))_l$-X, where the T radical is hydrogen, chlorine, bromine, iodine, p-toluenesulfonyl (OTs), methanesulfonyl (OMs), OH or $R_2S^+$, where each R may be the same or different to obtain a compound having the formula (25z):

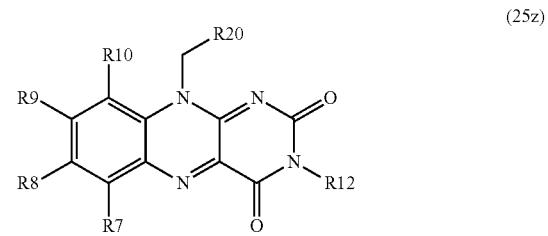

(25z)

or reacting the compound of the formula (24) obtained in step (B) with an alkylating agent of the general formula T-alkyl, T-alkenyl, T-cycloalkyl, T-cycloalkenyl, T-(C(D)(E))$_h$-OH, T-(C(D)(E))$_k$-aryl-(C(D)(E))$_l$-OH, T-aryl, T-(C(D)(E))$_h$-X or T-(C(D)(E))$_k$-aryl-(C(D)(E))$_l$-X, where the T radical is hydrogen, chlorine, bromine, iodine, p-toluenesulfonyl (OTs), methanesulfonyl (OMs), OH or R$_2$S$^+$, where each R may be the same or different to obtain a compound having the formula (25):

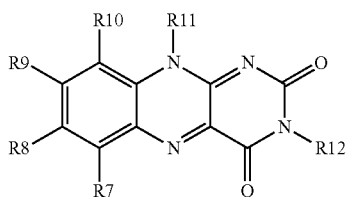

(25)

(D) optionally reacting the compound of the formula (24z) or (24) obtained in step (B) or the compound of the formula (25z) or (25) obtained in step (C) with tosyl chloride, mesyl chloride or iodine, optionally in the presence of a catalyst, and subsequently with an organic compound containing at least one tertiary nitrogen atom, when none of the R7 to R12 or R7 to R11 and R20 radicals is an organic radical of the general formula -(C(D)(E))$_h$-X or -(C(D)(E))$_k$-aryl-(C(D)(E))$_l$-X and when 1 R7 to R12 or R7 to R11 or R20 radical is an organic radical of the general formula -(C(D)(E))$_h$-OH or -(C(D)(E))$_k$-aryl-(C(D)(E))$_l$-OH, to obtain the 10H-benzo[g]pteridine-2,4-dione derivative of the formula (1), with the proviso that only 1 R1 to R6 radical is an organic radical of the general formula -(C(D)(E))$_h$-X or -(C(D)(E))$_k$-aryl-(C(D)(E))$_l$-X and where each h is an integer from 1 to 20 and k, l are each independently an integer from 0 to 6, where D and E are each independently hydrogen, halogen, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol and where each X is an organic radical having only one quaternary nitrogen atom and each aryl is a substituted or unsubstituted aromatic system having 5 to 20 carbon atoms or a substituted or unsubstituted heteroaromatic system which does not contain any nitrogen atom and has 4 to 20 carbon atoms.

17. The method as claimed in claim 5, wherein the inactivation of said microorganisms is a photodynamic inactivation.

18. The process as claimed in claim 13, wherein in step (C), each R in said R$_2$S$^+$ is independently selected from the group consisting of methyl, ethyl, propyl and butyl.

19. The process as claimed in claim 14, wherein the catalyst is a Lewis acid on a Brønsted acid.

20. The process as claimed in claim 15, wherein the free-radical initiator is a peroxide or an azo compound.

21. The process as claimed in claim 16, wherein in step (C), each R in said R$_2$S$^+$ is independently selected from the group consisting of methyl, ethyl, propyl and butyl.

22. The process as claimed in claim 16, wherein the halogen is selected from the group consisting of chlorine, bromine, iodine and fluorine.

23. The process as claimed in claim 16, wherein D and E are each independently hydrogen or hydroxyl.

\* \* \* \* \*